(12) United States Patent
Zou

(10) Patent No.: US 12,134,651 B2
(45) Date of Patent: *Nov. 5, 2024

(54) ANTI-RYK ANTIBODIES AND METHODS OF USING THE SAME

(71) Applicant: The Regents of the University of California, Oakland, CA (US)

(72) Inventor: Yimin Zou, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 576 days.

This patent is subject to a terminal disclaimer.

(21) Appl. No.: 17/127,913

(22) Filed: Dec. 18, 2020

(65) Prior Publication Data

US 2021/0198371 A1    Jul. 1, 2021

Related U.S. Application Data

(63) Continuation of application No. 16/086,958, filed as application No. PCT/US2017/024494 on Mar. 28, 2017, now Pat. No. 10,899,839.

(60) Provisional application No. 62/314,025, filed on Mar. 28, 2016.

(51) Int. Cl.
| | | |
|---|---|---|
| *C07K 16/00* | (2006.01) |
| *A01K 67/0276* | (2024.01) |
| *A61K 35/545* | (2015.01) |
| *A61K 39/00* | (2006.01) |
| *A61P 25/00* | (2006.01) |
| *A61P 25/28* | (2006.01) |
| *C07K 16/28* | (2006.01) |
| *G01N 33/50* | (2006.01) |

(52) U.S. Cl.
CPC ...... *C07K 16/2863* (2013.01); *A01K 67/0276* (2013.01); *A61K 35/545* (2013.01); *A61P 25/28* (2018.01); *C07K 16/00* (2013.01); *C07K 16/28* (2013.01); *G01N 33/5023* (2013.01); *A01K 2227/105* (2013.01); *A01K 2267/0318* (2013.01); *A01K 2267/0356* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 7,374,760 B2 * | 5/2008 | Zou ........................ | A61K 38/45 424/139.1 |
| 7,741,446 B2 | 6/2010 | Pardridge et al. | |
| 8,684,387 B1 | 3/2014 | Wu et al. | |
| 9,266,959 B2 | 2/2016 | Stagg et al. | |
| 2006/0228349 A1 | 10/2006 | Acton et al. | |
| 2008/0038257 A1 | 2/2008 | Han et al. | |
| 2014/0271629 A1 | 9/2014 | Corbit et al. | |
| 2015/0152181 A1 | 6/2015 | Sentman et al. | |
| 2015/0203579 A1 | 7/2015 | Papadopoulos et al. | |
| 2016/0053022 A1 | 2/2016 | Macheda et al. | |

FOREIGN PATENT DOCUMENTS

| | | |
|---|---|---|
| CN | 104768579 A | 7/2015 |
| WO | WO-2022/103705 A1 | 5/2022 |

OTHER PUBLICATIONS

Sano, (Curr Neurol Neurosc Rep 2: 392-399, 2002; abstract).*
Janeway et al., (Immunobiol: The Immune System in Health and Disease, 5th ed, pp. 1-6, 2001).*
Rudikoff et al (PNAS 79, 1979-1983, 1982; 1979).*
Vajdos et al. (J. Mol. Biol. 320, 415-428, 2002).*
Halliday et al (Clin Exp Pharmacol Physiol 27: 1-8, 2000).*
Steece-Collier et al., (PNAS USA 99(22): 13972-13974, 2002).*
Schmidt et al (Prog Neurobiol 88: 286-301, 2009).*
Ansar et al (Ind J Clin Med 4: 9-21, 2013).*
Wu et al. (J. Mol. Biol. 294, 151-162, 1999).*
Macheda et al. "The Wnt Receptor Ryk Plays a Role in Planar Cell Polarity Signaling," The Journal of Biological Chemistry, 2012, 287(35): 29312-29323.
Andre et al. "The Wnt coreceptor Ryk regulates Wnt/planar cell polarity by modulating the degradation of the core planar cell polarity component Vang12," The Journal of Biological Chemistry, 2012, 287(53): 44518-44525.
Romanelli et al. "p70 S6 kinase is regulated by protein kinase Czeta and participates in a phosphoinosifide 3-kinase-regulated signalling complex," Molecular and cellular biology, 1999, 19(4): 2921-2928.
Mairet-Coello et al. "The CAMKK2-AMPK kinase pathway mediates the synaptatoxic effects of Abeta oligomers through Tau phosphorylation," Neuron, 2013, 78(1): 94-108.
PCT/US2017/024494 International Search Report and Written Opinion mailed Sep. 8, 2017.
Saxena et al. "Mechanisms of axon degeneration: from development to disease," Progress in Neurobiology, 2007, 83: 174-191.
Wang et al. "Axon degeneration: molecular mechanisms of a self-destruction pathway," The Jounral of cell biology, 2012, 196(1): 7-18.
Yan et al. "Axon degeneration: Mechanisms and implications of a distinct program from cell death," Neurochemistry International, 2010, 56: 529-534.

(Continued)

*Primary Examiner* — Kimberly Ballard
*Assistant Examiner* — Aditi Dutt
(74) *Attorney, Agent, or Firm* — Foley & Lardner LLP

(57) ABSTRACT

Methods for inhibiting degeneration of a neuron, methods of treating a neurological/neurodegenerative disease, methods of modulating the directional growth of a neuron, and methods of interfering with the interaction of Wnt and Ryk are provided herein. Also provided are isolated anti-Ryk antibodies and antibody fragments that specifically bind to a binding domain of Wnt.

9 Claims, 45 Drawing Sheets

Specification includes a Sequence Listing.

(56) References Cited

OTHER PUBLICATIONS

Schmidt et al. "Axon guidance proteins: Novel therapeutic targets for ALS?" Progress in Neurobiology, 2009 88: 286-301.
Van Hoecke et al. "EPHA4 is a disease modifier of amyotrophic lateral sclerosis in animal models and in humans," Nature Medicine, 2012, 18(9): 1418-1424.
Tury et al. "Altered expression of alypical PKC and Ryk in the spinal cord of a mouse model of amyotrophic lateral sclerosis," Developmental Neurobiology, 2014, 74(8): 839-850.
Shi et al. "Hipoocampal neuronal polarity specififfied by the spatially localized mPar3/mPar6 and PI 3-kinase activity," Cell, 2003, 112: 63-75.
Nishimura et al. "Role of the PAR-3-KIF3 complex in the establishment of neuronal polarity," Nature cell biology, 2004, 6(4): 328-334.
Chen et al. "Microtubule affinity-regulating kinase 2 functions downstream of the PAR-3/PAR-6/atypical PKC complex in regulating hippocampal neuronal polarity," Proceedings of the National Academy of Sciences of the United States of America, 2006, 103(22): 8534-8539.
Parker et al. "Competing molecular interactions of aPKC isoforms regulate neuronal polarity," Proceedings of the National Academy of Sciences of the United States of America, 2013, 110(35): 14450-14455.
Zhang et al. "Dishevelled promotes axon differentiation by regulating atypical protein kinase C," Nature cell biology, 2007, 9(7): 743-759.
Mori et al. "An essential role of the aPKC-Aurora A-NDEL1 pathway in neunite elongation by modulation of microtubule dynamics," Nature cell biology, 2009, 11(9): 1057-1086.
Wolf et al. "Phosphatidylinositol-3-kinase-atypical protein kinase C signaling is required for Wnt attraction and anterior-posterior axon guidance," The Journal of neuroscience, 2008, 28(13): 3456-3407.
Onishi et al. "Antagonistic Functions of Dishevelleds Regulate Frizzled3 Endocytosis via Filopodia Tips in Wnt-Mediated Growth Cone Guidance," The Journal of neuroscience, 2013, 33(49): 19071-19085.
Wang et al. "Atypical PKC zeta is activated by ceramide, resulting in coactivation of NF-kappaB/JNK kinase and cell survival," Journal of neuroscience research, 1999, 55: 293-302.
Wooten et al. "Overexpression of atypical PKC in PC12 cells enhances NGF-responsiveness and survival through an NF-kappaB dependent pathway," Cell Death and Differentiation, 1999, 6: 753-764.
Xie et al. "Protein kinase C iota protects neural cells againsts apoptosis induced by amytoid beta-peptide," Molecular Brain Research, 2000, 82: 107-113.
Huang et al. "Activation of protein kinase A and atypical protein kinase C by A(2A) adenosine receptors antagonizes apoptosis due to serum deprivation in PC12 cells," The Journal of biological chemistry, 2001, 276(17): 13838-13846.
Kim et al. "Polarity proteins PAR6 and aPKC regulate cell death through GSK-3beta in 3D epithelial morphogenesis," Journal of Cell Science, 2007, 120(14): 2309-2317.
Joung et al. "p62 modulates Akt activity via association with PKCzeta in neuronal survival and differentiation," Biochemical and biophysical research communications, 2005, 334: 654-660.
Xin et al. "Protein kinase Czeta abrogates the proapoptotic funcion of Bax through phosphorytation," The Journal of biological chemistry, 2007, 282(29): 21268-21277.
Reyland. "Protein kinase C isoforms: Multi-functional regulators of cell life and death," Front Biosci (Landmark Ed), 2009, 14: 2386-2399.
Liu et al. "Ryk-mediated Wnt repulsion regulates posterior-directed growth of corticospinal tract," Nature neuroscience, 2005, 8(9): 1151-1159.
Schmitt et al. "Wnt-Ryk signalling mediates medial-lateral retinotectal topographic mapping," Nature, 2006, 439: 31-37.
Keeble et al. "Ryk: a novel Wnt receptor regulating axon pathfinding," The International journal of biochemistry & cell biology, 2006, 38: 2011-2017.
Keeble et al. "The Wnt receptor Ryk is required for Wnt5a-mediated axon guidance on the contralateral side of the corpus callosum," The Journal of Neuroscience, 2006, 26(21): 5840-5848.
Gonzalez et al. "The ryk receptor is expressed in glial and fibronectin-expressing cells after spinal cord injury," Journal of Neurotrauma, 2013, 30(10): 806-817.
Hollis et al. "Reinduced Wnt signaling limits regenerative potential of sensory axons in the spinal cord following conditioning lesion," Proceedings of the National Academy of Sciences of the United States of America, 2012, 109(36): 14663-14668.
Hollis et al. "Expression of the Wnt signaling system in central nervous system axon guidance and regeneration," Frontiers in molecular neuroscience, 2012, 5(5): 1-4.
Fradkin et al. "Ryks: new partners for Wnts in the developing and regenerating nervous system," Trends in Neurosciences, 2010, 33(2): 84-92.
Liu et al. "Repulsive Wnt signaling inhibits axon regeneration after CNS injury," The Journal of Neuroscience, 2008, 28 (33): 8376-8382.
Miyashita et al. "Wnt-Ryk signaling mediates axon growth inhibition and limits functional recovery after spinal cord injury," Journal of Neurotrauma, 2009, 26: 955-964.
Guenther et al. "Increased atypical PKC expression and activity in the phrenic motor nucleus following cervial spinal injury," Experimental neurology, 2012, 234(2): 513-520.
Luo et al. "Axon retraction and degeneration in development and disease," Annual review of neuroscience, 2005, 28: 127-156.
Watts et al. "Axon pruning during Drosophila metamorphosis: evidence for local degeneration and requirement of the ubiquitin-proteasome system," Neuron, 2003, 38(6): 871-885.
Zhai et al. "Involvement of the uhiquitin-proteasome system in the early stages of wallerian degeneration," Neuron, 2003, 39(2): 217-225.
Xiao et al. "Insights into the mechanism of microtubule stabilization by Taxol," Proceedings of the National Academy of Scieces of the United States of America, 2006, 103(27): 10166-10173.
Drewes et al. "MARK, a novel family of protein kinases that phosphorylate microtubule-associated proteins and trigger microtubule disruption," Cell, 1997, 89(2): 297-308.
Hurov et al. "Atypical PKC phosphorylates PAR-1 kinases to regulate localization and activity," Current Biology, 2004, 14(6): 736-741.
Matenia et al. "The tau of MARK: a polarized view of the cytoskeleton," Trends in Biochemical Sciences, 2009, 34(7): 332-342.
Shen et al. "JNK signaling pathway is a key modulator in cell death mediated by reactive oxygen and nutrogen species," Free Radical Biology & Medicine, 2006, 40: 928-939.
Manning et al. "Targeting JNK for therapeutic benefit: from junk to gold?" Nature Reviews Drug Discovery, 2003, 2: 554-565.
Yoshimura et al. "C-Jun N-terminal kinase induces axonal degeneration and limits motor recovery after spinal cord Injury in mice," Neuroscience Research, 2011, 71: 266-277.
Li et al. "JNK-dependent phosphorylation of c-Jun on serine 63 mediates nitric oxide-induced apoptosis of neuroblastoma cells," The Journal of biological chemistry, 2004, 279(6): 4058-4065.
Kamitori et al. "Expression of receptor tyrosine kinase RYK in developing rat central nervous system," Developmental Brain Research, 1999, 114: 149-160.
Lyu et al. "Cleavage of the Wnt receptor Ryk regulates neuronal differentiation during cortical neurogenesis," Developmental Cell, 2008, 15(5): 773-780.
Halford et al. "Ryk-deficient mice exhibit craniofacial defects associated with pertubed Eph receptor crosstalk," Nature genetics, 2000, 25: 414-418.
Wang et al. "Frizzled-3 is required for the development of major fiber tracts in the rostral CNS," The Journal of Neuroscience, 2002, 22(19): 8563-8573.

(56) References Cited

OTHER PUBLICATIONS

Hua et al. "Frizzled3 controls axonal development in distinct populations of cranial and spinal motor neurons," eLife, 2013, 2(e01482): 1-22.

Shafer et al. "Vangl2 promotes Wnt/planar cell polarity-like signaling by antagonizing Dvl1-mediated feedback inhibition in growth cone guidance," Developmental Cell, 2011, 20(2): 177-191.

Authorship_Nature Research journals' authorship policy, pp. 1-7, (downloaded on Jan. 14, 2020 from https:///www.nature.com/nature-research/editorial-policies/authorship).

Hollis, et al., "Ryk control remapping of motor cortex during functional recovery after spinal cord injury". Nature Neuroscience, vol. 19, No. 5, May 2016, pp. 697-705.

Liu et al. "Repulsive Wnt Signaling Inhibits Axon Regeneration after CNS Injury," The Journal of Neuroscience, vol. 28, No. 33 (2008) (pp. 8376-8382).

Notice of Allowance dated Sep. 2, 2020, from U.S. Appl. No. 16/086,958.

Paul, "Fundamental Immunology", Raven Press, Ltd, 3rd Edition, 1993, pp. 292-295.

Pessian, Maysam M., "Blocking Wnt Signaling in the Corticospinal Tract and Proprioceptive Sensory Axons", Thesis in Master of Science, 2013, 50 pages.

Reporting standards and availability of data, materials, code and protocols, Nature, pp. 1-13, (downloaded on Jan. 14, 2020 from http://www.nature.com/nature-research.editorial-policies/reporting-standards).

Smaglo, et al., "The development of immunoconjugates for targeted cancer therapy", Nat Rev Clin Oncol, Nov. 2014, 11(11), pp. 637-648.

\* cited by examiner

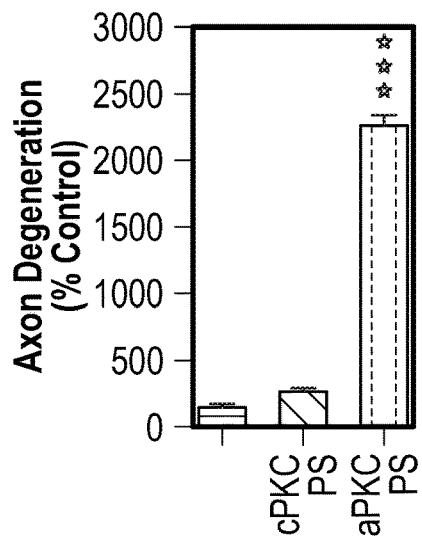
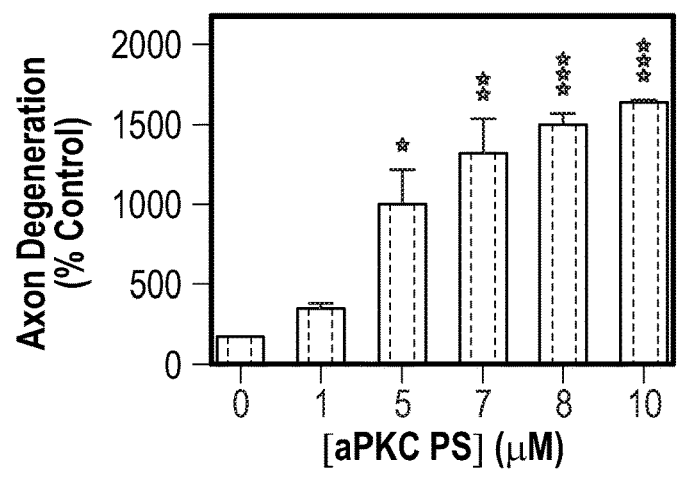
FIG. 2B
FIG. 2C
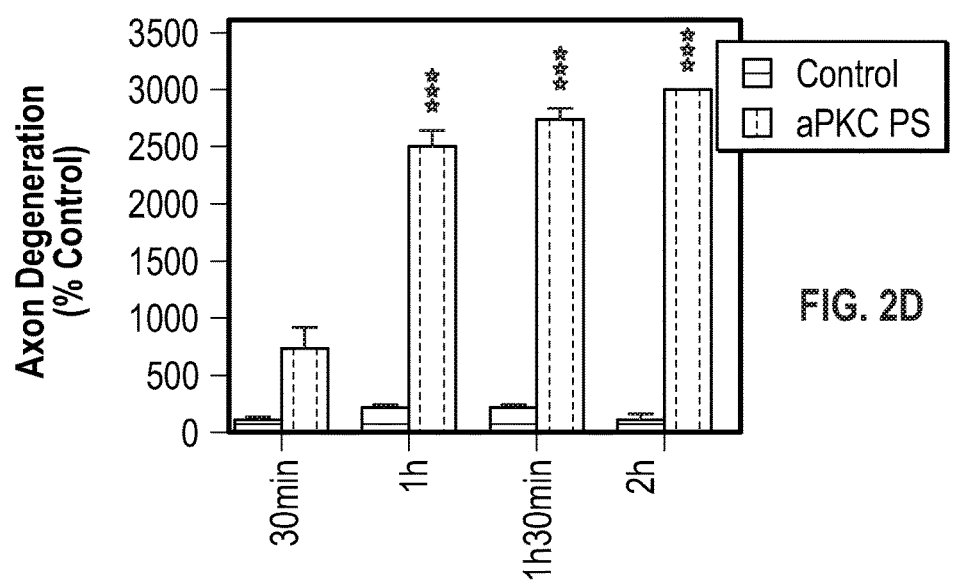
FIG. 2D
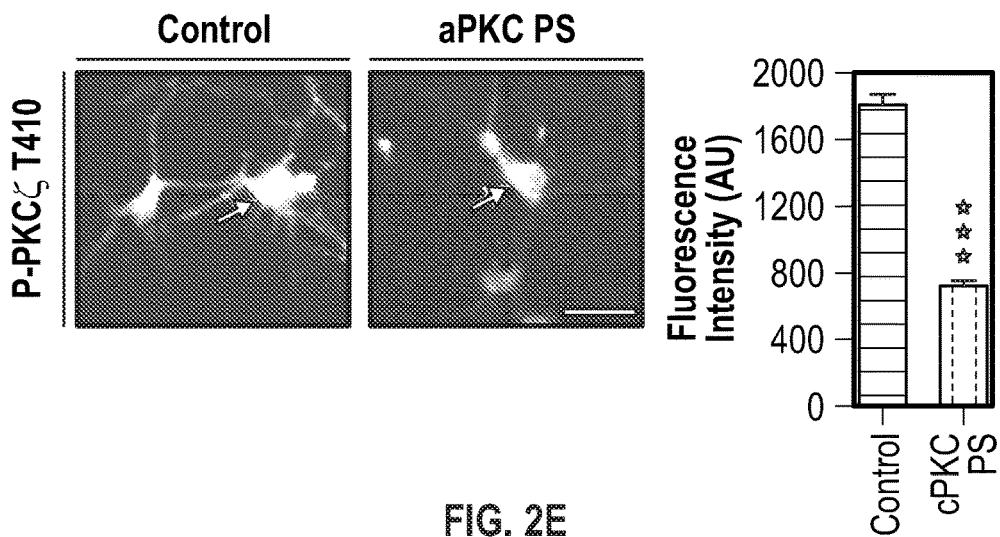
FIG. 2E

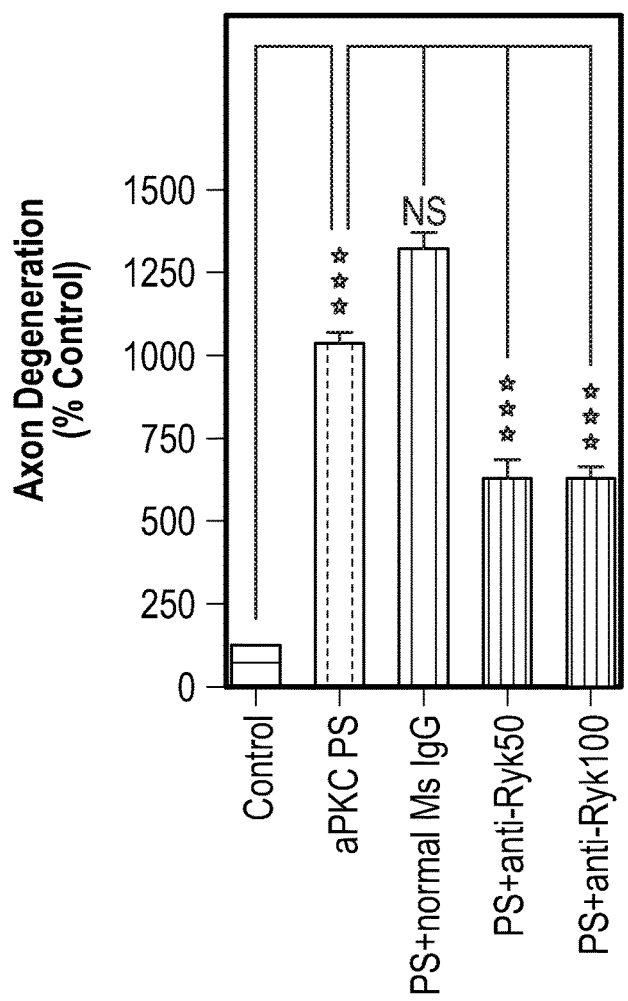
FIG. 5D
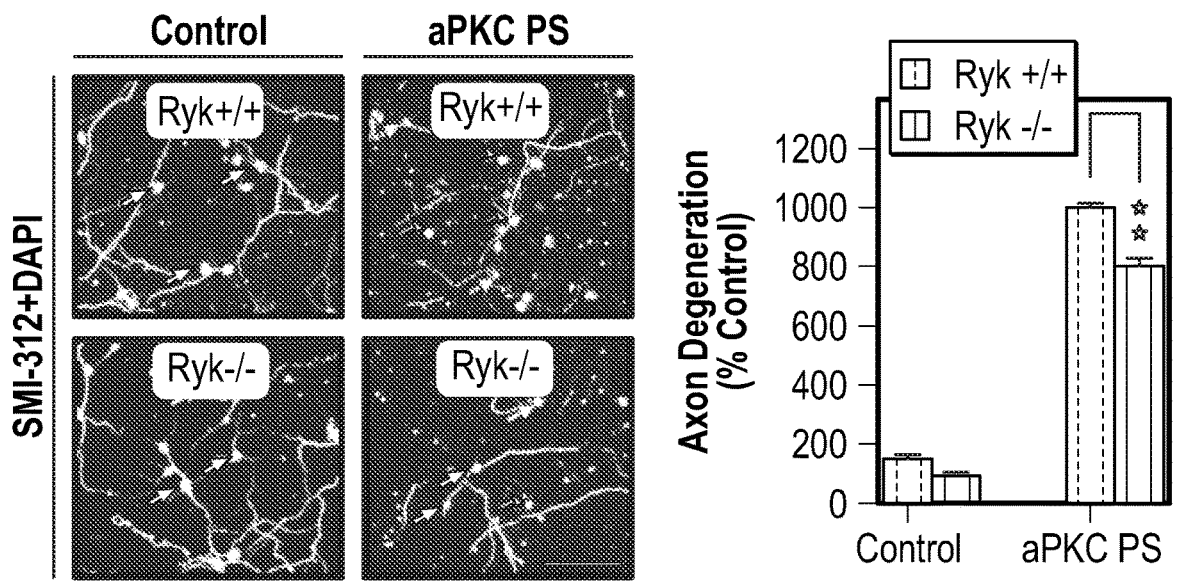
FIG. 5E
FIG. 5F

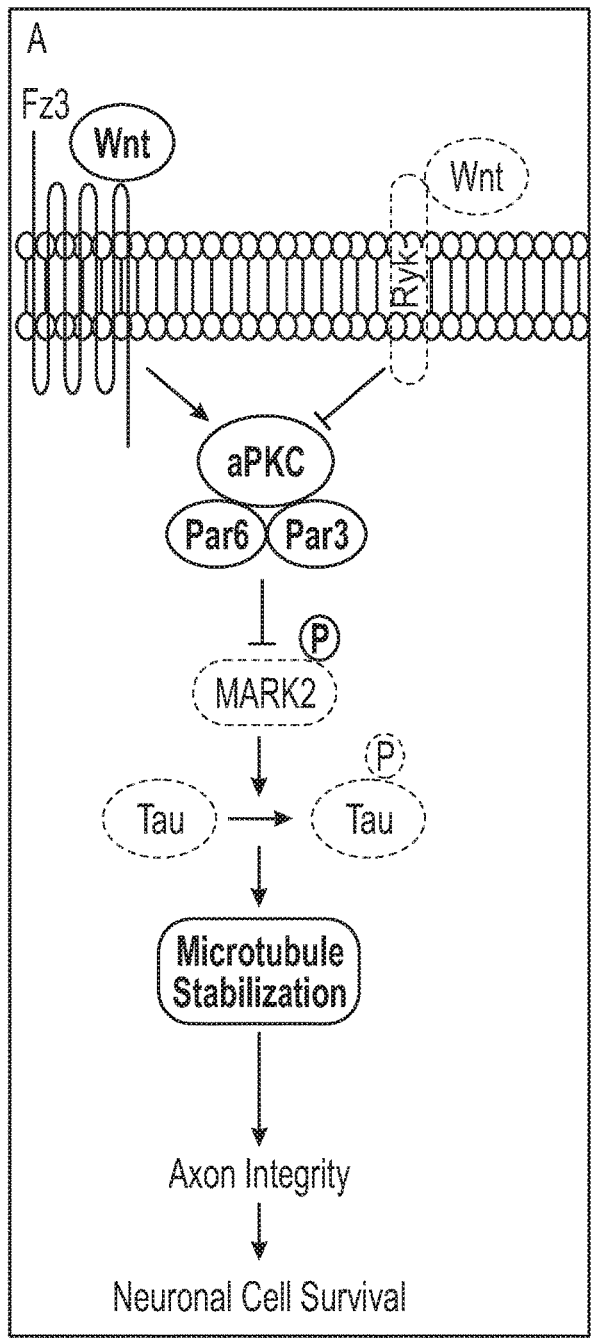
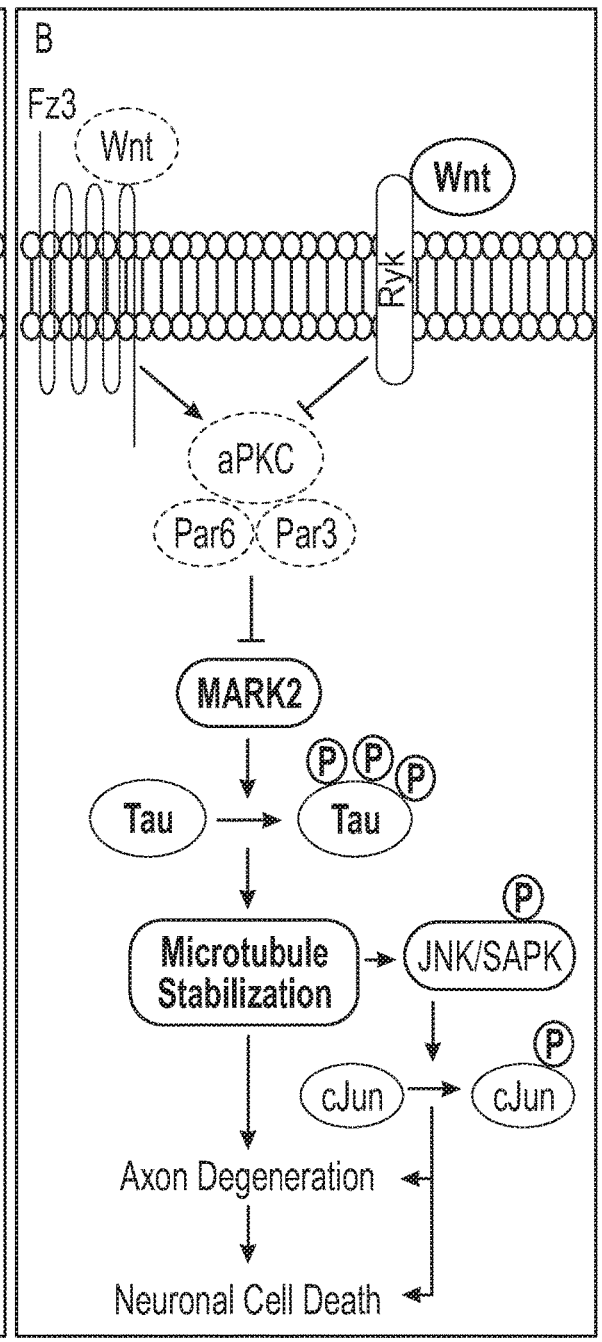
FIG. 7A  FIG. 7B

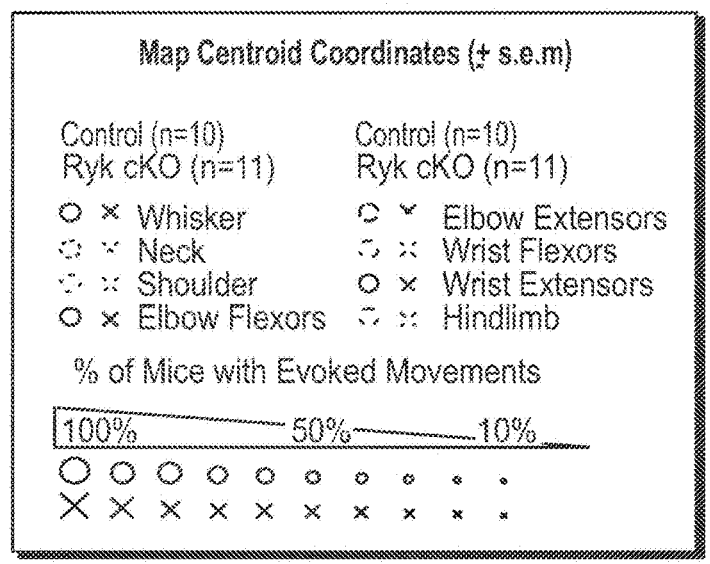
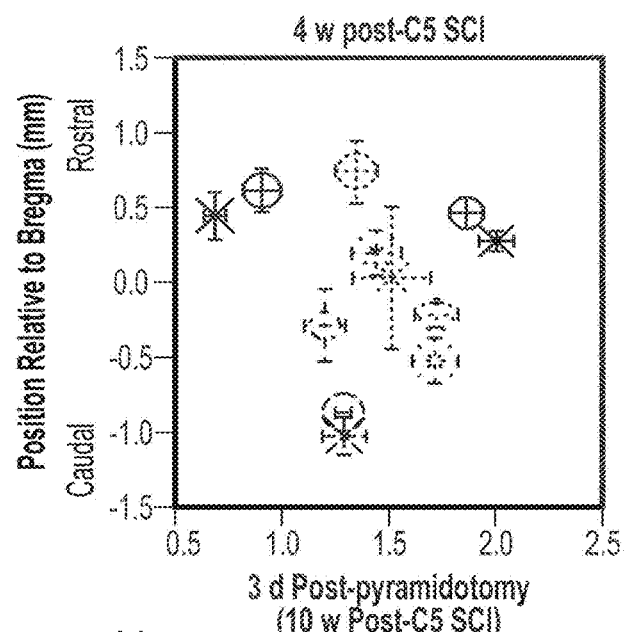
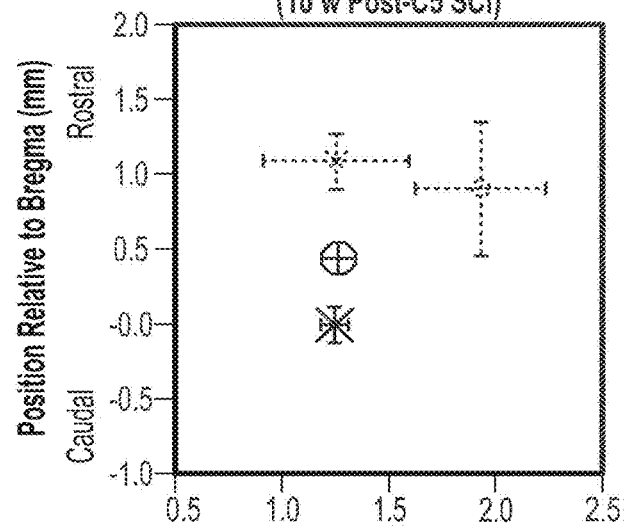
FIG. 14A (Continued)

SEQUENCE LISTING

```
<160> NUMBER OF SEQ ID NOS: 13

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Asp Ile Asn Ser Tyr
1               5

<210> SEQ ID NO 2
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ala Asn
1

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

Leu Gln Tyr Asp Glu Phe Pro Leu Thr
1               5

<210> SEQ ID NO 4
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
                20                  25                  30

Leu Ser Trp Ile Gln Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
        50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Phe Thr Phe Ser Ser Tyr Thr
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 6

Ile Ser Asn Gly Gly Gly Gly Thr
1               5

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Gly Asp Asn Gly Asp Tyr Trp Gly His Gly Ser Thr Leu Thr Val
1               5                   10                  15

Ser Ser Ala Lys
            20

<210> SEQ ID NO 8
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Lys Leu Val Glu Ser Gly Gly Asp Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Ile Arg Gln Thr Pro Glu Lys Arg Leu Glu Trp Val
        35                  40                  45

Ala Tyr Ile Ser Asn Gly Gly Gly Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Met Tyr Tyr Cys
                85                  90                  95

Thr Arg His Gly Asp Asn Gly Asp Tyr Trp Gly His Gly Ser Thr Leu
            100                 105                 110

Thr Val Ser Ser Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
        195                 200                 205

Val Asp Lys Lys Ile Val Pro Arg Asp Cys Gly Cys Lys Pro Cys Ile
    210                 215                 220

Cys Thr Val Pro Glu Val Ser Ser Val Phe Ile Phe Pro Pro Lys Pro
225                 230                 235                 240

-continued

Lys Asp Val Leu Thr Ile Thr Leu Thr Pro Lys Val Thr Cys Val Val
                245                 250                 255

Val Asp Ile Ser Lys Asp Asp Pro Glu Val Gln Phe Ser Trp Phe Val
            260                 265                 270

Asp Asp Val Glu Val His Thr Ala Gln Thr Gln Pro Arg Glu Glu Gln
        275                 280                 285

Phe Asn Ser Thr Phe Arg Ser Val Ser Glu Leu Pro Ile Met His Gln
    290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Ile Ser Lys Thr Lys Gly Arg Pro
                325                 330                 335

Lys Ala Pro Gln Val Tyr Thr Ile Pro Pro Lys Glu Gln Met Ala
            340                 345                 350

Lys Asp Lys Val Ser Leu Thr Cys Met Ile Thr Asp Phe Phe Pro Glu
        355                 360                 365

Asp Ile Thr Val Glu Trp Gln Trp Asn Gly Gln Pro Ala Glu Asn Tyr
    370                 375                 380

Lys Asn Thr Gln Pro Ile Met Asp Thr Asp Gly Ser Tyr Phe Val Tyr
385                 390                 395                 400

Ser Lys Leu Asn Val Gln Lys Ser Asn Trp Glu Ala Gly Asn Thr Phe
                405                 410                 415

Thr Cys Ser Val Leu His Glu Gly Leu His Asn His Thr Glu Lys
            420                 425                 430

Ser Leu Ser His Ser Pro Gly Lys
        435                 440

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Asp Ile Asn Arg Tyr
1               5

<210> SEQ ID NO 10
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Arg Tyr
            20                  25                  30

Leu Ser Trp Phe Gln Gln Lys Pro Gly Lys Ser Pro Glu Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

```
Glu Asp Met Gly Ile Tyr Tyr Cys Leu Gln Tyr Asp Glu Phe Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Ser Thr Gly Gly Gly Ser Thr
1               5

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Gly Glu Phe Asn Tyr Trp Gly Gln Gly Thr Leu Val Thr Val Ser
1               5                   10                  15

Ala Ala Lys

<210> SEQ ID NO 13
<211> LENGTH: 439
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Tyr Ile Ser Thr Gly Gly Gly Ser Thr Tyr Tyr Pro Asp Thr Val
```

```
                50                  55                  60
Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                     85                  90                  95

Ala Arg His Gly Glu Phe Asn Tyr Trp Gly Gln Gly Thr Leu Val Thr
                    100                 105                 110

Val Ser Ala Ala Lys Thr Thr Pro Pro Ser Val Tyr Pro Leu Ala Pro
            115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
            195                 200                 205

Asp Lys Lys Ile Val Pro Arg Asp Cys Gly Cys Lys Pro Cys Ile Cys
        210                 215                 220

Thr Val Pro Glu Val Ser Ser Val Phe Ile Phe Pro Pro Lys Pro Lys
225                 230                 235                 240

Asp Val Leu Thr Ile Thr Leu Thr Pro Lys Val Thr Cys Val Val Val
                245                 250                 255

Asp Ile Ser Lys Asp Asp Pro Glu Val Gln Phe Ser Trp Phe Val Asp
            260                 265                 270

Asp Val Glu Val His Thr Ala Gln Thr Gln Pro Arg Glu Glu Gln Phe
        275                 280                 285

Asn Ser Thr Phe Arg Ser Val Ser Glu Leu Pro Ile Met His Gln Asp
        290                 295                 300

Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
                325                 330                 335

Ala Pro Gln Val Tyr Thr Ile Pro Pro Pro Lys Glu Gln Met Ala Lys
            340                 345                 350

Asp Lys Val Ser Leu Thr Cys Met Ile Thr Asp Phe Phe Pro Glu Asp
        355                 360                 365

Ile Thr Val Glu Trp Gln Trp Asn Gly Gln Pro Ala Glu Asn Tyr Lys
        370                 375                 380

Asn Thr Gln Pro Ile Met Asp Thr Asp Gly Ser Tyr Phe Val Tyr Ser
385                 390                 395                 400

Lys Leu Asn Val Gln Lys Ser Asn Trp Glu Ala Gly Asn Thr Phe Thr
                405                 410                 415

Cys Ser Val Leu His Glu Gly Leu His Asn His His Thr Glu Lys Ser
            420                 425                 430

Leu Ser His Ser Pro Gly Lys
            435
```

ANTI-RYK ANTIBODIES AND METHODS OF USING THE SAME

CROSS REFERENCE TO RELATED APPLICATION(S)

This application a continuation of U.S. patent application Ser. No. 16/086,958, filed on Sep. 20, 2018, now U.S. Pat. No. 10,899,839 B2, which is a U.S. national phase filing of International Patent Application Serial No. PCT/US2017/024494, entitled "ANTI-RYK ANTIBODIES AND METHODS OF USING THE SAME," having an international filing date of Mar. 28, 2017, which claims the benefit of priority under 35 U.S.C. § 119(e) of U.S. Ser. No. 62/314,025, filed Mar. 28, 2016. The disclosures and contents of the above-referenced applications and patent are incorporated by reference in their entireties for all purposes.

GRANT INFORMATION

This invention was made with government support under Grant Nos. NS047484 and NS081738 awarded by the National Institutes of Health. The United States government has certain rights in the invention.

SEQUENCE LISTING

The instant application contains a Sequence Listing which has been submitted electronically in ASCII format and is hereby incorporated by reference in its entirety. Said ASCII copy, created on Mar. 16, 2017, is named 114198-3050_SL.txt and is 14,205 bytes in size.

BACKGROUND OF THE INVENTION

Field of the Invention

The invention relates generally to antibodies and more specifically to use of an anti-Ryk antibody or antibody fragment that specifically binds to a binding domain of Wnt to inhibit Wnt-Ryk signaling.

Background Information

The central nervous system (CNS) is connected by ascending sensory pathways and descending motor or regulatory pathways. In the CNS, somatosensory pathways ascend to the brain centers, and motor pathways controlling body movement descend from the brain to the spinal cord. Unlike the peripheral nervous system, damage to the central nervous system axons, such as spinal cord axons cannot be repaired, causing permanent impairment of neural function, such as in paralysis. The spinal cord serves important functions in the central nervous system. One such function is to allow communication of the body and the brain. The nerve fibers within the spinal cord carry messages to and from the brain to other parts of the body. In general, sensory information from the body travels along the spinal cord up to the brain and instruction from the brain, such as motor command, travels along the spinal cord down from the brain.

The term "spinal cord injury" refers to any injury of the neurons within the spinal canal. Spinal cord injury can occur from either trauma or disease to the vertebral column or the spinal cord itself. Most spinal cord injuries are the result of trauma to the vertebral column causing a fracture of the bone, or tearing of the ligaments with displacement of the bony column producing a pinching of the spinal cord. The majority of broken necks and broken backs, or vertebral fractures, do not cause any spinal cord damage; however, in 10-14% of the cases where a vertebral trauma has occurred, the damage is of such severity it results in damage to the spinal cord. It is estimated that the annual incidence of spinal cord injury (SCI), not including those who die at the scene of the accident, is approximately 40 cases per million population in the U.S., or approximately 11,000 new cases each year. The number of people in the U.S. who are alive today and who have SCI has been estimated to be between 721 and 906 per million population. This corresponds to between 183,000 and 230,000 persons. Treatment options for patients with spinal cord injuries are limited. Often, patients with SCI are left with severe, permanent disabilities.

In recent years, increasing evidence suggests that Wnts, which have been better known as morphogens in early development, are conserved axon guidance molecules during nervous system wiring both in vertebrates and invertebrates (Zou, Y. 2004. Trends Neurosci 27:528-32; Fradkin, et al. 2005. J Neurosci 25:10376-8; Zou & Lyuksyutova. 2007. Curr Opin Neurobiol 17:22-8; Salinas, et al. 2008. Annu Rev Neurosci 31:339-358). Wnts are secreted glycoproteins, which bind to three classes of receptors, the Frizzleds, Ryk and ROR2 (Gordon & Nusse. 2006. J Biol Chem 281:22429-33; Logan & Nusse. 2004. Annu Rev Cell Dev Biol 20:781-810). It has also been shown that the Wnt family proteins are essential guidance cues along the A-P axis of the spinal cord and topographic map formation in the retinotectal projections in development and may play important roles in regulating adult CNS axon regeneration after spinal cord injury (Lyuksyutova et al. 2003. Science 302:1984-8; Liu, et al. 2005. Nat Neurosci 8:1151-9; Schmitt et al. 2006. Nature 439:31-7; Wolf et al. 2008. J Neurosci 28:3456-67; Liu et al. 2008. The Journal of Neuroscience 28:8376-8382).

Commissural axons, which originate from the dorsal spinal cord, first project along the dorsal-ventral axis to grow towards the ventral midline, the floor plate. The ventrally directed growth of commissural axons are guided by repulsive cues, the BMPs emanating from the dorsal midline, the roof plate, and attractive cues, Netrin-1 and Sonic Hedgehog, secreted from the floor plate (Zou et al. 2007. Curr Opin Neurobiol 17:22-8). Once these commissural axons cross the midline, they lose responsiveness to midline attractants and gain sensitivity to chemorepellents, the Slits and Semaphorins, emanating from the floor plate and the neighboring ventral gray matter, forcing them to make a 90° turn into their longitudinal trajectory (Zou et al. 2000. Cell 102:363-75). The dorsal populations of rodent commissural axons all turn anterior and project towards the brain. The anterior turning requires Wnt-Frizzled signaling. Several Wnts, including Wnt4, Wnt7b, Wnt7a and Wnt5a, are expressed in an anterior-posterior decreasing gradient along the spinal cord at the ventral midline and attract post-crossing commissural axons, which have crossed the midline to turn anteriorly. When the Wnt gradient was disrupted by adding Wnt inhibitors, secreted Frizzled-related proteins (sFRPs) or positioning Wnt4-secreting cell aggregates in "open-book" explant culture, commissural axons show specific A-P randomize growth after midline crossing. In Frizzled3 mutant embryos, spinal cord commissural axons lose A-P directionality in vivo (Lyuksyutova et al. 2003. Science 302:1984-8).

Studies in *Drosophila* midline axon pathfinding independently showed that DWnt5 is a chemorepellent and repels a subset of commissural axons via a receptor called, Derailed (Yoshikawa et al. 2003. Nature 422:583-8). The vertebrate homologue of Derailed, Ryk, is also a repulsive Wnt receptor and an anterior-high posterior-low Wnt gradient created by differential expression of Wnt1 and Wnt5a, is required for the posterior growth of corticospinal tract axons in the spinal cord (Liu et al. 2005. Nat Neurosci 8:1151-9). Therefore, Wnts control A-P guidance of both ascending and descending axons in the spinal cord by attractive and repulsive guidance mechanisms. Wnt-Ryk signaling was also found to regulate the pathfinding of corpus callosum in the mammalian forebrain by a repulsive mechanism (Keeble et al. 2006. J Neurosci 26:5840-8). Studies in C. elegans showed that Wnt signaling control anterior-posterior directionality of the pathfinding of a number of axons and migration of neuroblasts (Pan et al. 2006. Dev Cell 10:367-77; Hilliard et al. 2006. Dev Cell 10:379-90; Prasad & Clark. 2006. Development 133:1757-66). Therefore, the A-P guidance mechanisms appear to be highly conserved in animal kingdom (Zou. 2006. Neuron 49:787-9.).

In addition to the role of Wnts in axon pathfinding, Wnt3 is also a positional cue for topographic mapping in the retinotectal system, acting as a laterally-directing mapping force for retinal ganglion cell axons, opposing the medially-directed force created by ephrinB1 gradient in the optic tectum (Schmitt et al. 2006. Nature 439:31-7). Wnt3 is expressed in a medial-high to lateral-low gradient in the optic tectum. Ryk is expressed in a dorsal-ventral (D-V) increasing gradient in the retinal ganglion cells. Therefore, the more ventral RGC axon branches are more strongly repelled by Wnt3 and Wnt3-Ryk signaling drives the interstitial branches to grow towards the lateral tectum. In the meantime, ephrinB1 is expressed in the same graded fashion and EphBs are expressed at higher levels in ventral RGCs. EphBs mediate attraction to ephrinB1. Therefore, the more ventral RGC axon branches are more attracted by ephinB1 towards the medial tectum. The balancing act between the medial (ephrinB1) and lateral (Wnt3) mapping forces ensures RGC axons to terminate at correct topographic positions. Remarkably, Wnt-Frizzled signaling is also required for proper dorsal-ventral retinotopic mapping in the Drosophila visual system (Sato et al. 2006. Nat Neurosci 9:67-75; Zou & Lyuksyutova. 2007. Curr Opin Neurobiol 17:22-8). Therefore, Wnts are conserved topographic mapping cues along the D-V axis.

Commissural axons of the developing spinal cord are guided to the ventral midline by a collaboration of chemoattractants (Netrin-1 and Sonic Hedgehog (Shh)) and chemorepellents (Bone Morphogenetic Proteins (BMPs)) secreted by midline floor plate and roof plate cells, respectively. Once these axons reach the floor plate they switch off their responsiveness to chemoattractants from the floor plate and become responsive to chemorepulsive cues also expressed by the floor plate cells and the surrounding ventral gray matter, including members of the Class 3 Semaphorins (Sema3B and Sema3F) and the Slit family proteins (Serafini, T., et al. Cell 78, 409-424, 1994; Kennedy, T. E., et al. Cell 78, 425-435, 1994; Serafini, T., et al. Cell 87, 1001-1014, 1996; Zou, Y., et al. Cell 102, 363-375, 2000; Charron, F., et al. Cell 113, 11-23, 2003; Long, H., et al. Neuron 42, 213-223, 2004). Neuropilin-2 mutant embryos showed severe guidance defects including stalling in the midline, overshooting to the contralateral side of the spinal cord and randomly projecting along the anterior-posterior axis (Zou, Y., et al. Cell 102, 363-375, 2000).

The identification of modulators of neuronal growth and regeneration following SCI could be applied in new forms of treatment of patients with this debilitating condition. The identification of modulators of neuronal growth and regeneration could also be applied in the treatment of patients with other disorders involving neuronal dysfunction, such as neurological/neurodegenerative diseases or disorders. Agents that can promote axonal growth along the A-P axis following injury to the spinal cord may be applied to help prevent the permanent paralysis that is often associated with SCI. Therefore, there is a need for better treatments of SCI, and a greater understanding of modulators of neuronal growth and regeneration might lead to improved methods of treatment of such neurological/neurodegenerative diseases or disorders.

SUMMARY OF THE INVENTION

The present invention is based on the finding that an anti-Ryk antibody or antibody fragment that specifically binds to a binding domain of Wnt inhibits Wnt-Ryk signaling. As such, the anti-Ryk antibody or antibody fragment may be used to modulate the directional growth of a mammalian neuron when the spinal cord has been damaged, as well as to inhibit degeneration of a neuron and to treat a neurodegenerative disease.

Accordingly, in one aspect, the invention provides an isolated anti-Ryk antibody or antibody fragment that specifically binds to a binding domain of Wnt or specifically binds to the same epitope on Wnt as does a reference antibody or antibody fragment, or cross-competes for specific binding to Wnt with a reference antibody or antibody fragment. In various embodiments, the antibody or antibody fragment and/or the reference antibody or antibody fragment includes a heavy chain variable region comprising the CDR sequences set forth in SEQ ID NOs: 5-7 or SEQ ID NOs: 5, 11, and 12; and/or a light chain variable region comprising the CDR sequences set forth in SEQ ID NOs: 1-3 or SEQ ID NOs: 9, 2, and 3. In various embodiments, the antibody or antibody fragment specifically binds to an epitope within amino acid residues 90-183 of Wnt. In various embodiments, the heavy chain variable region of the antibody or antibody fragment includes an amino acid sequence comprising at least 85% sequence identity, at least 90% sequence identity, at least 95% sequence identity, or at least 99% sequence identity to SEQ ID NOs: 8 or 13. In various embodiments, the light chain variable region of the antibody or antibody fragment includes an amino acid sequence comprising at least 85% sequence identity, at least 90% sequence identity, at least 95% sequence identity, or at least 99% sequence identity to SEQ ID NOs: 4 or 10. In various embodiments, the antibody or antibody fragment is formulated in a pharmaceutically acceptable carrier or excipient.

In another aspect, the invention provides a nucleic acid sequence encoding the isolated antibody or antibody fragment described herein. Also provided is a vector, such as an expression vector, that includes the nucleic acid sequence. Also provided is a host cell, such as a mammalian host cell that includes the vector.

In another aspect, the invention provides an immunoconjugate of the isolated anti-Ryk antibody or antibody fragment linked to a therapeutic agent such as a cytotoxin or a radioactive isotope. In another aspect, the invention provides a bispecific molecule, e.g., a bispecific antibody, which includes the isolated anti-Ryk antibody or antibody fragment linked to a second functional moiety having a different binding specificity than the isolated anti-Ryk antibody or antibody fragment.

In another aspect, the invention provides a method of interfering with interaction of Wnt and Ryk. The method includes contacting a sample that includes Wnt and Ryk with the isolated antibody or antibody fragment described herein, thereby interfering with the interaction of Wnt and Ryk.

In another aspect, the invention provides a method of inhibiting degeneration of a neuron. The method includes contacting the neuron with the isolated antibody or antibody fragment described herein, thereby inhibiting degeneration of the neuron. In various embodiments, degeneration of an axon of the neuron is inhibited or degeneration of a cell body of the neuron is inhibited. In various embodiments, the axon is a spinal cord commissural axon, an upper motor neuron axon, or a central nervous system axon. In various embodiments, the neuron is a damaged spinal cord neuron, a sensory neuron, a motor neuron, a cerebellar granule neuron, a dorsal root ganglion neuron, a cortical neuron, a sympathetic neuron, or a hippocampal neuron. In various embodiments, the neuron forms part of a nerve graft or a nerve transplant. In various embodiments, the neuron is ex vivo or in vitro. In various embodiments, the nerve graft or the nerve transplant forms part of an organism, such as a mammal or human.

In another aspect, the invention provides a method of treating a neurological disease or disorder, e.g., a neurodegenerative disease or disorder in a subject having or being at risk of developing the neurological disease or disorder, e.g., a neurodegenerative disease or disorder. The method includes administering to the subject the isolated antibody or antibody fragment described herein, thereby treating the neurological disease or disorder, e.g., a neurodegenerative disease or disorder, in the subject. In various embodiments, the neurodegenerative disease is amyotrophic lateral sclerosis, Alzheimer's disease or Parkinson's disease.

In another aspect, the invention provides a method for modulating the directional growth of a mammalian neuron. The method includes contacting the neuron with the isolated antibody or antibody fragment described herein, thereby modulating the directional growth of the neuron, a spinal cord commissural axon, an upper motor neuron axon, or a central nervous system axon. In various embodiments, the neuron is a damaged spinal cord neuron, a sensory neuron, a motor neuron, a cerebellar granule neuron, a dorsal root ganglion neuron, a cortical neuron, a sympathetic neuron, or a hippocampal neuron. In various embodiments, the neuron forms part of a nerve graft or a nerve transplant. In various embodiments, the neuron is ex vivo or in vitro. In various embodiments, the directional growth of the neuron facilitates regeneration of the neuron.

In another aspect, the invention provides a transgenic non-human mammal such as a mouse whose genome comprises a heterozygous or homozygous deletion, inactivation or knock-out of the Ryk gene. In various embodiments, the mouse has the phenotype Frizzled3$^{-/-}$ Ry$^{+/-}$. In various embodiments, the mouse contains a conditional disruption of the Ryk gene, e.g., a corticospinal tract (CST)-specific disruption of the Ryk gene. In various embodiments, the disrupted Ryk gene includes a recombinant Ryk allele, a selectable marker, frt sites flanking the selectable marker, and loxP sites flanking a portion of the allele. The marker may be PGK Neo and the loxP sites may flank exons 3-6 of the allele. Thus, the invention also provides an isolated cell derived from the transgenic non-human mammal. Also provided is a vector for making the transgenic non-human mammal whose genome comprises a heterozygous or homozygous deletion, inactivation or knock-out of the Ryk gene. An exemplary vector can include a portion of a Ryk gene, wherein exons 3-6 of the Ryk gene are flanked by 3' and 5' loxP sites, a selectable marker between exon 6 and the 5' loxP site, and frt sites flanking the selectable marker.

In another aspect, the invention provides a method of producing a knockout mouse with a conditional disruption of the Ryk gene, e.g., a CST-targeted disruption in a Ryk gene. The method includes transfecting the vector described above into a population of murine embryonic stem (ES) cells, selecting a transfected ES cell which expresses said selectable marker, introducing said transfected ES cell into an embryo of an ancestor of said mouse, allowing said embryo to develop to term to produce a chimeric mouse with a conditional knock-out construct in its germ line, breeding said chimeric mouse to produce a heterozygous mouse with a conditionally disruptable Ryk gene, and breeding said heterozygous mouse with a mouse containing a loxP-flanked stop cassette preventing tdTomato expression only in corticospinal axons to produce a mouse with a conditional disruption of the Ryk gene, e.g., a CST-specific disruption in the Ryk gene.

In another aspect, the invention provides a method of screening for an agent that modulates the amount, level and/or activity of atypical protein kinases C (aPKC) or MARK2. For example, provided herein is a method of screening of screening for a therapeutic agent for treating a neurological disease or disorder. The method includes administering a test agent to the transgenic non-human mammal described herein and evaluating the effect of the test agent on at least one of: the amount of atypical protein kinases C (aPKC) or MARK2 protein, the level of aPKC or MARK2 activity or the level of aPKC or MARK2 in at least one disease-relevant tissue of the transgenic non-human mammal, wherein at least one of: a decrease in the amount of aPKC protein, an increase in the amount of MARK2 protein, a decrease in the level of aPKC activity, an increase in the level of MARK2 activity, a reduction in the level of aPKC, or an increase in the level of MARK2 in at least one disease-relevant tissue relative to a similar transgenic non-human mammal that does not receive the test agent indicates the test agent is therapeutic for the neurological disease or disorder.

BRIEF DESCRIPTION OF THE DRAWINGS

FIG. 1A shows that endogenous aPKC is localized in cortical neuron cell bodies (E16.5) (arrows) and in SMI-312+ axons (arrowheads). FIGS. 1B-1F show overexpression of PKCζ-WT, PKCζ-KD or PKCζ-T410A in cerebral cortical neurons (pCIG2-EGFP was used as control). FIG. 1B shows that recombinant PKCζ-WT protein is localized in both neuronal cell bodies (arrows) and processes (arrowheads) while PKCζ-KD and PKCζ-T410A proteins are absent in neurites. FIG. 1C shows a higher magnification image showing intact neurites (plain arrows) in a PKCζ-WT transfected neuron and fragmented neurites in a PKCζ-KD transfected cell (dotted arrows) labeled for EGFP. FIG. 1D shows aCasp3 immunostaining in neurons transfected with the indicated plasmid. FIG. 1E shows the number of transfected neurons with degenerative neurites (dotted arrows in B) counted over the total number of EGFP+ neurons and expressed as the % of the control. FIG. 1F shows the number of apoptotic transfected neurons (aCasp3+ EGFP+) counted over the total number of EGFP+ neurons. Data represent mean±SEM (n=5 experiments in FIG. 1E, n=3 experiments in FIG. 1F. * $p<0.05$, ** $p<0.01$, ANOVA with Bonferroni post-test. Scale bars: 200 μm (FIG. 1B), 100 μm (FIG. 1D), 50 μm (FIGS. 1A and 1C).

FIGS. 2A-2H are pictorial and graphical diagrams showing that aPKC inhibition induces rapid axon degeneration that precedes neuronal cell body death. FIGS. 2A and 2B show axon degeneration in E16.5 cerebral cortical neurons treated with 1004 myristoylated aPKC PS for 2 h. The proportion of neurons with degenerative axons was counted over the total number of neurons (SMI-312+ cells,). Plain arrows indicate neurons with intact axons, dotted arrows neurons with beading axons and arrowheads neurons without axons. FIGS. 2C and 2D show aPKC PS induced axon fragmentation in a dose-(FIG. 2C) and time- (FIG. 2D) dependent manner. FIG. 2E shows aPKC PS treatment reduced phosphorylation of PKCζ-T410. Cell cultures were fixed and immunolabeled with anti-phospho-PKCζ-T410 antibody. P-PKCζ-T410 immunoreactivity was measured in neuronal cell bodies (arrows) in neuronal cell cultures incubated with water (Control) or 10 μM aPKC PS for 2 h. FIGS. 2F-2I show axon degeneration induced by aPKC inhibition precedes cell body death. Cortical neurons incubated with water (Control) or 10 μM aPKC PS for 2 h, 4 h or 24 h, fixed and double-labeled for SMI-312 and TUNEL (FIG. 2F) or activated caspase-3. Plain arrows indicate dead neuronal cell bodies labeled for TUNEL in control neurons and neurons treated with aPKC PS. Dotted arrows indicate neurons with beading axons that are not labeled for TUNEL. Graphs represent the proportion of neurons with degenerative axons (FIG. 2G) and of dead neurons (TUNEL+ (FIG. 2H) or aCasp3+ (FIG. 2I)) counted after 2 h, 4 h or 24 h of aPKC PS treatment in SMI-312+ neurons. Data represent mean±SEM (n=3 experiments). * $p<0.05$,  $p<0.01$, *$p<0.001$. FIGS. 2B-2D: ANOVA with Bonferroni post-test; FIGS. 2E and 2G-2I: unpaired Student's t test. Scale bars: 50 μm (FIGS. 2A and 2F), 25 μm (FIG. 2E).

FIGS. 3A and 3B show axon degeneration induced by aPKC is partially prevented by stabilizing microtubules with taxol. Cortical neurons were incubated with 10 μM taxol for 2 hours prior to and during 2 h treatment of 7 μM aPKC PS. Cells were fixed and immunolabeled with SMI-312 antibody. The proportion of neurons with intact axons was counted in SMI-312+ neurons (FIG. 3B). Plain arrows indicate neurons with intact axons. Dotted arrows indicate neurons with beading axon. Arrowheads indicate neurons without axons. FIGS. 3C-3F show the results from Western blottings performed with proteins lysates from E16.5 cerebral cortical cell cultures incubated with water (Control) or 10 μM aPKC PS for 2 hours. Phospho-protein levels were assessed by densitometric analysis and normalized with the corresponding total protein and actin or GAPDH (FIGS. 3C-3E). The level of Glu-tubulin protein was normalized with GAPDH (FIG. 3F). Lanes 1-3 and lanes 4-6 represent triplicates for control and for aPKC PS respectively. FIGS. 3G-3I show that Tau-S262A overexpression protects neurons from neurite degeneration induced by PKCζ-KD overexpression. E16.5 cortical cells cultured for 3 days transfected with the indicated plasmids were fixed 2 days after transfection and immunolabeled for EGFP and aCasp3 and counterstained with DAPI. FIG. 3H shows the number of transfected neurons with degenerative neurites counted over the total number of EGFP+ neurons. FIG. 3I shows the number of apoptotic transfected neurons (aCasp3+ EGFP+) counted over the total number of EGFP+ neurons. Data represent mean±SEM. FIGS. 3B-3F: n=3 experiments; FIGS. 3H and 3I: n=4 experiments. * $p<0.05$,  $p<0.01$, * $p<0.001$, FIGS. 3B-3F: Unpaired Student's t test; H,I: ANOVA with Bonferroni post-test. Scale bars: 50 μm (FIG. 3A), 100 μm (FIG. 3G).

FIGS. 4A-4C show that JNK phophorylation is increased upon aPKC inhibition. Western blotting were performed with proteins lysates from E16.5 cortical neurons cultured for 3 days incubated with water (Control) or 10 μM aPKC PS for 1 h or 2 h. FIGS. 4B and 4C show phospho-protein levels assessed by densitometric analysis. Levels of phospho-proteins were normalized with the corresponding total protein and GAPDH. FIGS. 4D and 4E show that cortical neuronal cultures incubated with water (Control) or 10 μM aPKC PS for 1 h were immunolabled for P-JNK T183/T185 (D) or P-c-Jun S63 (FIG. 4E). Arrows indicate increased immunoreactivity in neurons treated with aPKC PS compared to control neurons. Data represent mean±SEM. n=3 experiments/group, * $p<0.05$, ** $p<0.01$, unpaired Student's t test. Scale bar: 100 μm.

FIGS. 5A-5F are pictorial and graphical diagrams showing that Ryk promotes axonal degeneration induced by aPKC inhibition. FIGS. 5A and 5B show that aPKC activity is increased in Ryk KO mouse cortical neuronal cell cultures. Western blotting were performed with proteins lysates from cortical neurons from E16.5 Ryk wild type, heterozygous and KO embryos cultured for 3 days in vitro. Levels of P-PKCζ-T410 were assessed by densitometric analysis and normalized with total PKC and GAPDH. FIGS. 5C and 5D show that monoclonal Ryk antibody blocks degeneration. E16.5 cortical neurons were incubated with monoclonal mouse anti-Ryk antibody (50 μg/ml or 100 μg/ml) or normal mouse IgG (100 μg/ml) for 2 hours prior to and during 2 h treatment of 704 aPKC PS. Cells were fixed and immunolabeled for SMI-312. FIG. 5D shows the proportion of SMI-312+ neurons with degenerative axons. FIGS. 5E and 5F show reduced degeneration with Ryk knockout mouse. Cortical neurons individually dissociated from E16.5 WT ($Ryk^{+/+}$) and Ryk KO embryos ($Ryk^{-/-}$) were incubated with 704 aPKC PS for 2 h. Cells were fixed and immunolabeled for SMI-312. FIG. 5F shows the proportion of SMI-312+ neurons with degenerative axons in $Ryk^{+/+}$ and $Ryk^{-/-}$ neurons treated with aPKC PS or water (control). Plain arrows indicate neurons with intact axons, dotted arrows neurons with beading axons and arrowheads neurons without axons. Data represent mean±SEM (FIG. 5A: $Ryk^{+/+}$: n=3 embryos, $Ryk^{+/-}$ n=3 embryos, $Ryk^{-/-}$: n=4 embryos; D: n=5 experiments; FIG. 5F: $Ryk^{+/+}$: n=4 embryos, $Ryk^{-/-}$: n=6 embryos). * $p<0.05$,  $p<0.001$, * $p<0.001$; FIGS. 5B and 5F: Unpaired Student's t test, D: ANOVA with Bonferroni post-test. Scale bars: 100 μm.

FIG. 6A shows a lower magnification of a WT brain section ($Ryk^{+/+}$) showing the localization of the retrosplenial (RSP) cortex. FIGS. 6B and 6C show that $aCasp3^+$ cell number is decreased in $Ryk^{-/-}$ embryos compared to Ryk mice. FIGS. 6D and 6E show that $aCasp3^+$ cell number is increased in the RSP of $Frizzled3^{-/-}$ embryos compared to $Frizzled3^{+/-}$ and $Frizzled3^{+/-}$ mice. Ryk knockdown attenuates cell death in the RSP of Frizzled3KO mice. Data represent mean±SEM ($Ryk^{+/+}$: n=6 embryos, $Ryk^{+/-}$: n=4 embryos, $Ryk^{-/-}$: n=5 embryos, Frizzled3+/+: n=4 embryos, $Frizzled3^{+/-}$: n=6 embryos, $Frizzled3^{-/-}$: n=8 embryos, $Frizzled3^{-/-}$ $Ryk^{+/-}$: n=5 embryos). * $p<0.05$,  $p<0.01$,  $p<0.001$. FIG. 6C: Student's t test, E: ANOVA with Bonferroni post-test. HIPP: hippocampus, LV: lateral ventricle, RSP: retrosplenial cortex. Scale bars: 500 μm (FIG. 6A), 200 μm (FIGS. 6B and 6D).

FIGS. 7A and 7B are pictorial diagrams showing a model of aPKC action on axonal integrity and neuronal cell survival. FIG. 7A shows that in normal conditions when aPKC is expressed and active, aPKC inhibits MARK2 activity through phosphorylation on T585. Phosphorylation state of Tau is low and Tau binds to and stabilizes microtubules, maintaining axon integrity and neuronal cell survival. FIG. 7B shows that when aPKC kinase activity is reduced or inhibited, MARK2 activity increases and phosphorylates Tau in its microtubule binding domain on S262. Hyperphosphorylated Tau detach from microtubules which destabilizes microtubules. Disruption of microtubules activates the stress kinase JNK/SAPK pathway, leading to axonal degeneration and neuronal cell death.

FIG. 8A shows a timeline outlining experimental details of bilateral cervical level S (CS) dorsal column lesion. FIGS. 8B-8C show generation of Ryk conditional allele. FIG. 8B shows that exons 3-6 were flanked with loxP sites. FIG. 8C shows the results of a Western blot of postnatal day 7 motor cortex extract from mice infected at postnatal day 0 with AAV2/1 synapsin Cre. Full-length blot presented in FIGS. 23A and 23B. FIGS. 8D and 8E show a schematic showing the level of the CS lesion in relation to motor neuron pools for distinct forelimb muscle groups (adapted from McKenna, Prusky, and Whishaw, 2000). FIG. 8F shows behavioral performance on forelimb reach skilled food-pellet retrieval task shows enhanced recovery after Ryk conditional deletion in bilateral motor cortex (n=2S mice (control), 17 mice (Ryk cKO), from 21 litters, repeated measures ANOVA P=0.0003, F(1, 40)=16.0102). Data presented as mean±s.e.m.

FIGS. 9A and 9B are representative images of tdTomato-labeled CST axons from eight serial sagittal cryosections spaced 140 μm apart superimposed over GFAP astroglial staining at the center of injury (1 experiment, n=12 mice/group, from 11 litters; compass showing dorsal (D), ventral (V), rostral (R), and caudal (C)). Mice with Ryk conditional deletion had greater levels of collateralization both rostral and caudal to the lesion than control mice (one-tailed t-test *P<O.OS). FIGS. 9C and 9D show higher magnification of single confocal planes from boxed regions (1.5 mm caudal to the lesion site) indicated in FIGS. 9A and 9B, respectively. FIG. 9E shows the sum of tdTomato labeled axons (normalized to pyramidal labeling) over 3 mm rostral to lesion relative to control in the dorsal columns (n=12 mice/group, one-tailed t-test P=0.12, t(21) =1.198) and in the gray matter. Mice with Ryk conditional deletion had greater levels of collateralization both rostral and caudal to the lesion than control mice (n=12 mice/group, one-tailed t-test *P<O.OS: rostral P=0.0499 t(19)=1.730, caudal P=0.0397 t(19)=1.855). FIGS. 9F-9H show the distribution of corticospinal axons (axon index is thresholded pixels at every 0.411 μm in 8 total saggital spinal cord cryosections divided by thresholded pixels in transverse pyramids) within the dorsal columns (FIG. 9F) or spinal gray matter (FIGS. 9G and 9H). FIG. 9H is a magnified view of rostral collaterals from FIG. 9G. CS injury site is at 0 μm, rostral is represented with negative numbers, caudal with positive. Data in FIG. 9E is presented as median with inter-quartile range, data in FIGS. 9F-9H is presented as mean±s.e.m.

FIGS. 10A and 10B show media-lateral distribution of corticospinal axons shows highest increase in collaterals proximal to the main, dorsal corticospinal tract (regions I and II) after Ryk conditional deletion (n=12 mice/group, one-tailed t-test *P<O.OS: II rostral P=0.0225 t(19)=2.146, II caudal P=0.0295 t(21)=1.996, I caudal P=0.0059 t(17)=2.819). FIG. 10C shows both control and Ryk conditional deletion mice showed pre-synaptic densities (vGlut1 colocalization with tdTomato-labeled corticospinal axons) at 600 μm rostral to the CS injury site (1 experiment, n=9 mice/group). FIG. 10D shows media-lateral distribution of corticospinal innervation at 600 μm rostral to CS injury site. All data presented as median and inter-quartile range.

FIG. 11A is a timeline outlining experimental details of secondary C3 lesion experiments following recovery from bilateral CS dorsal column lesion. FIG. 11B is a schematic of secondary C3 injury, above the level of increased pre-synaptic density shown in (FIGS. 10C-10E). FIG. 11C shows behavioral performance on forelimb reach skilled food-pellet retrieval task shows elimination of enhanced recovery after Ryk conditional deletion by second C3 dorsal column lesion (1 experiment, n=8 (control sham), 7 (control C3), 6 (Ryk cKO sham & C3) mice, mice from 14 litters, ANOVA P=0.0102 F(3)=4.7432, Bonferroni corrected t-test *P<0.05: 1. Ryk cKO sham v. control sham P=0.0106, 2. Ryk cKO sham v. Ryk cKO C3 P=0.0092). FIGS. 11D-11F show secondary C3 dorsal column lesion eliminated enhanced levels of collateralization in Ryk conditional deleted mice. FIG. 11D shows representative images of tdTomato-labeled CST axons from 8 serial sagittal cryosections spaced 140 μm apart superimposed over GFAP astroglial staining at the center of injury (1 experiment, 7 control, 6 Ryk cKO mice). FIGS. 11E and 11F show distribution of corticospinal axons (axon index as described above) within the dorsal columns (FIG. 11E) or spinal gray matter (FIG. 11F). C3 injury site is at 0 μm, rostral is represented with negative numbers, caudal with positive. Data in FIG. 11C presented as median and inter-quartile range, data in FIGS. 11E and 11F are presented as mean±s.e.m.

FIG. 12A is a schematic showing antibody infusion by intrathecal catheterization. FIG. 12B shows behavioral performance on forelimb reach skilled food-pellet retrieval task shows enhanced recovery in rats infused with Ryk monoclonal antibody for 28 days starting at time of injury (n=6 rats (IgG control), 5 rats (Ryk monoclonal), repeated measures ANOVA P=0.0354, F(1,9)=6.113). FIG. 12C shows behavioral performance on skilled locomotor grid crossing task was not affected by Ryk monoclonal antibody infusion. FIG. 12D shows that Ryk monoclonal recognizes full-length Ryk protein expressed in transfected COS-7 cells by Western and immunocytochemistry. FIGS. 12E-12H show that BDA-labeled corticospinal axons in rats infused with Ryk monoclonal antibody had greater levels of collateralization than control mouse IgG infused rats. FIGS. 12E and 12F are images of BDA-labeled CST axons from 6 serial sagittal cryosections spaced 280 μm apart superimposed over GFAP astroglial and NG2 staining at the center of injury. FIGS. 12G and 5H show a distribution of corticospinal axons (axon index is thresholded pixels at every 0.741 μm in 6 total saggital spinal cord cryosections divided by thresholded pixels in transverse pyramids) within the dorsal columns (FIG. 12G) or spinal gray matter (FIG. 12H). CS injury site is at 0 μm, rostral is represented with negative numbers, caudal with positive. FIG. 12I shows the sum of normalized axon collaterals over 5 mm relative to control. Rats infused with Ryk monoclonal antibody had greater levels of collateralization both rostral and caudal to the lesion than control mouse IgG infused rats (n=6 rats (IgG control), 5 rats (Ryk monoclonal), one-tailed t-test 585 *P<0.05: rostral P=0.0446 t(6)=2.000, caudal P=0.019 t(6)=2.594). Data in FIGS. 12B, 12C, 12G, and 12H is presented as mean±s.e.m., data in FIG. 12I is presented as median and inter-quartile range.

FIG. 13A is a timeline outlining experimental details of optogenetic mapping with weekly behavioral testing following bilateral CS dorsal column lesion. FIG. 13B is a topographic representation of elbow flexor and extensor activation, relative to bregma (*) prior to and 3 days, 4 weeks, and 8 weeks after CS dorsal column lesion. Data presented as total number of mice responding with evoked movements at each location, lighter color indicates a larger number of mice are responsive at a given location. Each tic mark represents 300 μm. FIG. 13C shows that subsequent C3 dorsal column lesion disrupts remodeled circuitry, while subsequent pyramdidotomy eliminates unilateral evoked motor output. Both measured at 3 days after injury.

FIG. 14A is a cortical map re-organization from spinal cord injury in mice that received weekly training demonstrates how map centroids shift after injury. Size of the marker is proportional to the percentage of mice with evoked motor movements of a given muscle group. FIGS. 14B and 14C show elbow extensor motor maps shift caudal and medial towards cortex originally occupied by hindlimb representations. FIGS. 14D and 14E show that mice with Ryk conditional deletion have a greater proportion devoted to elbow flexor activation at 4 weeks post-CS lesion (FIG. 14D) and conversely a smaller proportion of the motor cortex devoted to extensor activation (FIG. 14E) (n=10 (control) 11 (Ryk cKO) mice, one-tailed t-test *P<0.05: elbow flexion P=0.0347 t(19)=1.925, elbow extension P=0.0460 t(16)=-1.791, data presented as mean±s.e.m.). FIG. 14F is a model for recruitment of ectopic cortical motor regions mediated by axon plasticity. After dorsal column injury, the immediate expansion of forelimb regions above the level of injury is likely mediated by lateral connectivity within the motor cortex. Increased axonal plasticity and connectivity after Ryk conditional deletion likely drives the formation of novel, ectopic areas of forelimb motor cortex.

FIG. 15A is a timeline outlining experimental details of optogenetic mapping with only terminal behavioral testing at 8 weeks post-injury. FIG. 15B is a topographic representation of elbow flexor and extensor activation, relative to bregma (*) prior to and 3 days, 4 weeks, and 8 weeks after CS dorsal column lesion in the absence of weekly behavioral testing. FIG. 15C shows that at 8 weeks after CS dorsal column lesion, mice with weekly behavioral testing, both Ryk cKO and controls, performed better than those only tested at 8 weeks (n=10 (control weekly testing), 11 (Ryk cKO weekly testing), 5 (control & Ryk cKO 8 wk only testing) mice, ANOVA P=0.0037 F(3)=5.7157, Bonferroni corrected t-test *P<0.05: 1. Ryk cKO weekly v. 8 week only testing P=0.0277, 2. control weekly v. 8 week only testing P=0.0346, data presented as median and inter-quartile range). FIG. 15D shows that in animals with weekly behavioral testing (black Xs), there was a strong correlation of wrist movement and skilled forelimb reach performance, regardless of injury or genotype (n=84 measurements (4 time points, 21 mice), bivariate Pearson correlation P, P<0.0001 p=0.665). Light blue is density ellipse (a=0.95). Mice with no weekly behavioral testing are shown in red.

FIG. 17A shows the specificity of Ryk monoclonal antibody. Full-length blot presented in FIGS. 23A and 23B. FIG. 17B is a timeline outlining experimental details of Ryk monoclonal antibody infusion after bilateral C5 dorsal column lesion in rats.

FIG. 23A shows the specificity of Ryk monoclonal antibody from FIG. 17A. FIG. 23B shows a Western blot of postnatal day 7 motor cortex extract from mice infected at postnatal day 0 with AAV2/1 synapsin Cre from FIG. 8C. E18.5 cortex from two separate Ryk KO embryonic mouse cortices as control in right two lanes. GAPDH loading control from same blot.

DETAILED DESCRIPTION OF THE INVENTION

Figure 1A:
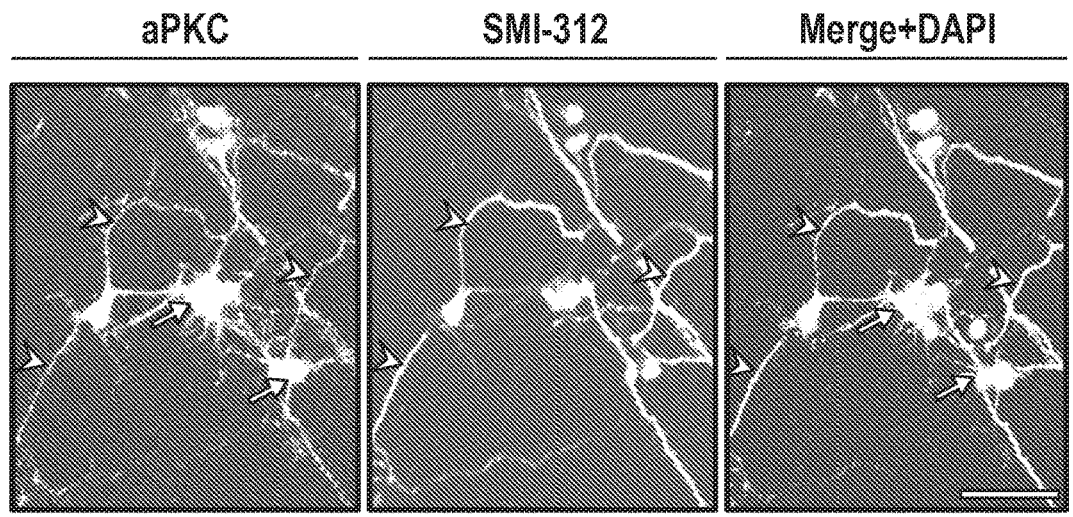
FIGS. 1A-1F are pictorial and graphical diagrams showing that inhibition of aPKC induces neurite degeneration and neuronal apoptosis.

The present invention is based on the finding that an anti-Ryk antibody or antibody fragment that specifically binds to a binding domain of Wnt inhibits Wnt-Ryk signaling. As such, the present invention provides methods for modulating neuron degeneration and neuron guidance using the anti-Ryk antibody or antibody fragment. Thus, the anti-Ryk antibody or antibody fragment can be used to treat a neurological disease or disorder, e.g., a neurodegenerative disease or disorder, in a subject having or being at risk of developing the neurological disease or disorder, e.g., a neurodegenerative disease or disorder, and/or to treat spinal cord injury (SCI) in a subject.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance.

The term "effective amount" or "therapeutically effective amount" refers to the amount of an active agent sufficient to induce a desired biological result. That result may be alleviation of the signs, symptoms, or causes of a disease, or any other desired alteration of a biological system. The term "therapeutically effective amount" is used herein to denote any amount of the formulation which causes a substantial improvement in a disease condition when applied to the affected areas repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

A "subject," "individual," or "patient," is used interchangeably herein, which refers to a vertebrate, preferably a mammal, more preferably a human. Mammals include, but are not limited to, murines, simians, humans, farm animals, sport animals, and pets. Tissues, cells and their progeny of a biological entity obtained in vitro or cultured in vitro are also encompassed.

As used herein, "promote" or "increase," or "promoting" or "increasing" are used interchangeably herein. These terms refer to the increase in a measured parameter (e.g., activity, expression, signal transduction, neuron degeneration) in a treated cell (tissue or subject) in comparison to an untreated cell (tissue or subject). A comparison can also be made of the same cell or tissue or subject between before and after treatment. The increase is sufficient to be detectable. In some embodiments, the increase in the treated cell is at least about 10%, 20%, 30%, 40%, 50%, 60%, 70%, 80%, 90%, 1-fold, 2-fold, 3-fold, 4-fold or more in comparison to an untreated cell.

As used herein, "inhibit," "prevent" or "reduce," or "inhibiting," "preventing" or "reducing" are used interchangeably herein. These terms refer to the decrease in a measured parameter (e.g., activity, expression, signal transduction, neuron degeneration) in a treated cell (tissue or subject) in comparison to an untreated cell (tissue or subject). A comparison can also be made of the same cell or tissue or subject between before and after treatment. The decrease is sufficient to be detectable. In some embodiments, the decrease in the treated cell is at least about 10%, 20%, 30%, 40%, 50%, 60%, 70%, 80%, 90%, or completely inhibited in comparison to an untreated cell. In some embodiments the measured parameter is undetectable (i.e., completely inhibited) in the treated cell in comparison to the untreated cell.

The term "selective inhibition" or "selectively inhibit" as referred to a biologically active agent refers to the agent's ability to preferentially reduce the target signaling activity as compared to off-target signaling activity, via direct or indirect interaction with the target.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

A conservative substitution may include substitution such as basic for basic, acidic for acidic, polar for polar, etc. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" Comput. Appl Biosci. 9: 745-756; Taylor W. R. (1986) "The classification of amino acid conservation" J. Theor. Biol. 119; 205-218). Conservative substitutions may be made, for example, according to the table below which describes a generally accepted Venn diagram grouping of amino acids.

TABLE 1

Grouping of amino acids

| Characteristic | Set | Characteristic | Subset |
|---|---|---|---|
| Hydrophobic | F W Y H K M<br>I L V A G C | Aromatic<br>Aliphatic | F W Y H<br>I L V |
| Polar | W Y H K R E<br>D C S T N Q | Charged<br>Positive | H K R E<br>D H K R |
|  |  | Charged<br>Negative | E D |
| Small | V C A G S<br>P T N D | Tiny | A G S |

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., 60% identity, optionally 65%, 70%, 75%, 80%, 85%, 90%, or 95% identity over a specified region, or, when not specified, over the entire sequence), when compared and aligned for maximum correspondence over a comparison window, or designated region as measured using one of the following sequence comparison algorithms or by manual alignment and visual inspection. The invention provides polypeptides that are substantially identical to the polypeptides, respectively, exemplified herein, as well as uses thereof including, but not limited to, use for treating or preventing neurological diseases or disorders, e.g., neurodegenerative diseases or disorders, and/or treating SCI. Optionally, the identity exists over a region that is at least about 50 nucleotides in length, or more preferably over a region that is 100 to 500 or 1000 or more nucleotides in length, or the entire length of the reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

Two examples of algorithms that are suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

As used herein, the term "dominant negative mutant" of a protein refers to a mutant polypeptide or nucleic acid, which lacks wild-type activity and which, once expressed in a cell wherein a wild-type of the same protein is also expressed, dominates the wild-type protein and effectively competes with wild type proteins for substrates, ligands, etc., and thereby inhibits the activity of the wild type molecule. The dominant negative mutant can be a polypeptide having an amino acid sequence substantially similar (i.e., at least about 75%, about 80%, about 85%, about 90%, about 95% similar) to the wild type protein. The dominant negative mutant can also be a polypeptide comprising a fragment of the wild type protein, e.g., the C-domain of the wild-type protein. The dominant negative mutant can be a truncated form of the wild type protein.

Mouse Model

As used herein, "transgenic organism" refers to an animal in which exogenous DNA has been introduced while the animal is still in its embryonic stage. In most cases, the transgenic approach aims at specific modifications of the genome, e.g., by introducing whole transcriptional units into the genome, or by up- or down-regulating or mutating pre-existing cellular genes. The targeted character of certain of these procedures sets transgenic technologies apart from experimental methods in which random mutations are conferred to the germline, such as administration of chemical mutagens or treatment with ionizing solution. A transgenic organism can include an organism which has a gene knock-out or may result for inducing a genetic mutation.

A "genetic knock out" refers to partial or complete suppression of the expression of a protein encoded by an endogenous DNA sequence in a cell. The "knockout" can be affected by targeted deletion of the whole or part of a gene encoding a protein. Alternatively, the transgenic organism can be obtained by the targeted mutation of a functional protein in an embryonic stem cell. As a result, the deletion or mutation may prevent or reduce the expression of the protein in any cell in the whole animal in which it is normally expressed, or results in the expression of a mutant protein having a biological function different than the normal/wild-type protein.

The term "knockout animal" and "transgenic animal", refer to a transgenic animal wherein a given gene has been suppressed or mutated by recombination with a targeting vector. It is to be emphasized that the term is intended to include all progeny generations. Thus, the founder animal and all F1, F2, F3, and so on, progeny thereof are included.

As used herein, the phrase "conditional knockout," or "cKO," when used to describe a non-human transgenic mammal such as a mouse, refers to mice containing a knock-out of a specific gene in a certain tissue. The creation of a genetically engineered cKO mouse involves inserting specific DNA sequences, such as a knock-out construct/vector, into the mouse DNA. The inserted sequences are recognized by two DNA specific enzymes, frt recombinase (also known as flippase) and Cre recombinase, not normally present in mice. Cre recombinase recognition sites are termed loxP sites and flippase recognition sites are termed frt sites. Each of these enzymes can cut and remove a DNA sequence that is flanked by its recognitions sites. This can lead to disruption of gene function if a functional DNA sequence of the gene of interest is removed. In addition, a selectable marker gene is inserted into the mouse, the introduction of which allows selection of embryonic mouse cells (stem cells) that contain the Cre recombination or flippase recognition sites. The resultant mouse is a conditional knockout mouse.

A knock-out construct is a nucleic acid sequence, such as a DNA construct, which, when introduced into a cell, results in suppression (partial or complete) of expression of a polypeptide or protein encoded by endogenous DNA in the cell. An exemplary knock-out construct is provided herein. This construct contains a loxP site 5' to exon 3 and 3' to exon 6 of the Ryk gene, a selectable marker cassette and a loxP site 3' to the selectable marker cassette. The selectable marker cassette comprises frt sites 5' and 3' to the selectable marker and is between the 3' frt site and the selectable marker gene. Suitable selectable markers include, but are not limited to, neomycin, puromycin and hygromycin.

Animals containing more than one transgenic construct and/or more than one transgene expression construct may be prepared in any of several ways. An exemplary manner of preparation is to generate a series of animals, each containing one of the desired transgenic phenotypes. Such animals are bred together through a series of crosses, backcrosses and selections, to ultimately generate a single animal containing all desired transgenic traits and/or expression constructs, where the animal is otherwise congenic (genetically identical) to the wild type except for the presence of the construct(s) and/or transgene(s).

Embryonic stem (ES) cells are typically selected for their ability to integrate into and become part of the germ line of a developing embryo so as to create germ line transmission of the transgene. Thus, any ES cell line that can do so is suitable for use herein. ES cells are generated and maintained using methods well known to the skilled artisan, such as those described by Doetschman et al. (1985) J. Embryol. Exp. Mol. Biol. 87:27-45). Any line of ES cells can be used, however, the line chosen is typically selected for the ability of the cells to integrate into and become part of the germ line of a developing embryo so as to create germ line transmission of the transgenic/knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934). Still another ES cell line is the WW6 cell line (Ioffe et al. (1995) PNAS 92:7357-7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. (1987)); by Bradley et al. (1986) Current Topics in Devel. Biol. 20:357-371); and by Hogan et al. (Manipulating the Mouse Embryo: A Laboratory Manual, Cold Spring Harbor Laboratory Press, Cold Spring Harbor, N.Y. (1986)).

Introduction of the knock-out construct into ES cells may be accomplished using a variety of methods well-known in the art, including, for example, electroporation, microinjection, and calcium phosphate treatment. For introduction of the DNA sequence, the knock-out construct DNA is added to the ES cells under appropriate conditions for the insertion method chosen. If the cells are to be electroporated, the ES cells and construct DNA are exposed to an electric pulse using an electroporation machine (electroporator) and following the manufacturer's guidelines for use. After electroporation, the cells are allowed to recover under suitable incubation conditions. The cells are then screened for the presence of the knockout construct. Screening for cells which contain the transgene (homologous recombinants) may be done using a variety of methods. For example, as described herein, cells can be processed as needed to render DNA in them available for screening with specific probes by polymerase chain reaction (PCR).

Once appropriate ES cells are identified, they are introduced into an embryo using standard methods. They can be introduced using microinjection, for example. Embryos at the proper stage of development for integration of the ES cell to occur are obtained, such as by perfusion of the uterus of pregnant females. For example, mouse embryos at 3-4 days development can be obtained and injected with ES cells using a micropipet. After introduction of the ES cell into the embryo, the embryo is introduced into the uterus of a pseudopregnant female mouse. The stage of the pseudopregnancy is selected to enhance the chance of successful implantation. In mice, 2-3 days pseudopregnant females are appropriate.

Successful incorporation of ES cells into implanted embryos results in offspring termed chimeras. Chimeras capable of germline transmission of the mutant allele are identified by standard methods. Chimeras are bred and the resulting progeny are screened for the presence of the desired alteration (e.g., the modified recombinant Ryk allele). This may be done, for example, on the basis of coat color or by obtaining DNA from offspring (e.g., tail DNA) to assess for the transgene, using known methods (e.g., Southern analysis, dot blot analysis, PCR analysis). Transgene expression may also be assessed (e.g., to determine if a replacement construct is expressed) by known methods, such as northern analysis or PCR analysis. Southern hybridization or PCR analysis of progeny DNA (e.g., tail DNA) may be conducted to identify desired genotypes. A suitable technique for obtaining completely ES cell derived transgenic non-human organisms is described in WO 98/06834, incorporated herein by reference.

In various embodiments, the cKO mice disclosed herein include at least three elements: (1) at least two enzyme-specific recognition sites flanking a critical portion of the target gene; (2) a gene encoding a selection marker such as, but not limited to neomycin; and (3) at least two enzyme-specific recognition sites flanking a selection marker gene for easy removal upon breeding with specific mouse strains. In a non-limiting example, exons 3-6 of the target gene has been designated as the critical portion. In one embodiment the enzyme-specific recognition sites flanking the critical portion of the target gene are loxP sites. In another embodiment, the enzyme-specific recognition sites flanking the selection marker gene are frt sites.

As mentioned above, the homologous recombination of the above described "knock-out" and/or "knock in" constructs is sometimes rare and such a construct can insert non-homologously into a random region of the genome where it has no effect on the gene which has been targeted for deletion, and where it can potentially recombine so as to disrupt another gene which was otherwise not intended to be altered. Such non-homologous recombination events can be selected against by modifying the above-mentioned targeting vectors so that they are flanked by negative selectable markers at either end (particularly through the use of the diphtheria toxin gene, thymidine kinase gene, the polypeptide product of which can be selected against in expressing cell lines in an appropriate tissue culture medium well known in the art—e.g., one containing a drug such as ganciclovir. Non-homologous recombination between the resulting targeting vector comprising the negative selectable marker and the genome will usually result in the stable integration of one or both of these negative selectable marker genes and hence cells which have undergone non-homologous recombination can be selected against by growth in the appropriate selective media (e.g., media containing a drug such as ganciclovir). Simultaneous selection for the positive selectable marker and against the negative selectable marker will result in a vast enrichment for clones in which the construct has recombined homologously at the locus of the gene intended to be mutated. The presence of the predicted chromosomal alteration at the targeted gene locus in the resulting stem cell line can be confirmed by means of Southern blot analytical techniques which are well known to those familiar in the art. Alternatively, PCR can be used.

Other methods of making transgenic animals are also generally known. See, for example, Manipulating the Mouse Embryo, (Cold Spring Harbor Laboratory Press, Cold Spring Harbor, N.Y., 1986). Recombinase dependent transgenic organisms can also be generated, e.g., by homologous recombination to insert target sequences, such that tissue specific and/or temporal control of inactivation of a Ryk gene can be controlled by recombinase sequences.

Accordingly, in one aspect, the invention provides a transgenic non-human mammal such as a mouse whose genome comprises a heterozygous or homozygous deletion, inactivation or knock-out of the Ryk gene and methods of making the same. In various embodiments, the mouse has the phenotype Frizzled3$^{-/-}$ Ryk$^{+/-}$. In various embodiments, the mouse contains a corticospinal tract (CST)-specific disruption of the Ryk gene. In various embodiments, the disrupted Ryk gene includes a recombinant Ryk allele, a selectable marker, frt sites flanking the selectable marker, and loxP sites flanking a portion of the allele. The marker may be PGK Neo and the loxP sites may flank exons 3-6 of the allele. Also provided is an isolated cell derived from the transgenic non-human mammal.

Neurons

As used herein, the term "neuron" include a neuron and a portion or portions thereof (e.g., the neuron cell body, an axon, or a dendrite). The term "neuron" as used herein denotes nervous system cells that include a central cell body or soma, and two types of extensions or projections: dendrites, by which, in general, the majority of neuronal signals are conveyed to the cell body, and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column). Certain specific examples of neuron types that may be subject to treatment or methods according to the invention include cerebellar granule neurons, dorsal root ganglion neurons, and cortical neurons.

The term "neuronal degeneration" is used broadly and refers to any pathological changes in neuronal cells, including, without limitation, death or loss of neuronal cells, any changes that precede cell death, and any reduction or loss of an activity or a function of the neuronal cells. The pathological changes may be spontaneous or may be induced by any event and include, for example, pathological changes associated with apoptosis. The neurons may be any neurons, including without limitation sensory, sympathetic, parasympathetic, or enteric, e.g., dorsal root ganglia neurons, motor neurons, and central neurons, e.g., neurons from the spinal cord. Neuronal degeneration or cell loss is a characteristic of a variety of neurological diseases or disorders, e.g., neurodegenerative diseases or disorders. In some embodiments, the neuron is a sensory neuron. In some embodiments, the neuron is a motor neuron. In some embodiments, the neuron is a damaged spinal cord neuron.

In some embodiments, degeneration occurs in a portion of the neuron such as the neuron cell body, an axon, or a dendrite. Accordingly, the degeneration can be inhibited in the degenerated portion or portions of the neuron. In some embodiments, the degeneration of an axon of the neuron is inhibited. In some embodiments, the degeneration of a cell body of the neuron is inhibited. The axon can be an axon of any neuron. For example, in some embodiments, the axon is a spinal cord commissural axon, or an upper motor neuron axon, or a central nervous system axon.

As described herein, the disclosed methods can be carried out in vivo, such as in the treatment of neurodegenerative diseases, neurological disorders or injuries to the nervous system. The methods can also be carried out in vitro or ex vivo, such as in laboratory studies of neuron function and in the treatment of nerve grafts or transplants. Accordingly, in some embodiments, the neuron forms part of a nerve graft or a nerve transplant. In some embodiments, the neuron is ex vivo or in vitro. In some embodiments, the nerve graft or the nerve transplant forms part of an organism, human or non-human (e.g., mammal, primate, rat, mouse, rabbit, bovine, dog, cat, pig, etc.).

Axon Degeneration

Axon degeneration is a common feature in many neurological and neurodegenerative diseases/disorders and in traumatic injuries. Studies indicate that it can occur independent of and before the death of neuronal cell bodies. However, the molecular and cellular mechanisms underlying axonal degeneration and protection are still unclear. Elucidating the degeneration pathways that are activated or the protection pathways that are inactivated during axon pathology will help develop specific therapeutic agents that preserve axon integrity and enhance regeneration.

During the development of the nervous system, axons respond to extracellular signals that promote the growth as well as those that inhibit their growth. Some extracellular cues attract axons to grow towards higher concentration and others repel axon away from higher concentration. The signaling pathways that regulate these opposite axon responses have profound effect on the extension and removal of axons, although their functions in mature axons have not been well characterized. Studies suggest that axon guidance molecules may play a role in neurological/neurodegenerative disorders, such as amyotrophic lateral sclerosis (ALS).

Atypical protein kinases C (aPKC), including PKCζ and PKCι/λ play crucial roles in many cellular processes including cell polarization and survival. In neurons, aPKC has been involved in cell polarity (7-13), neurite differentiation (11-13) and axon guidance (14) (15). aPKC mediates axon attraction to Wnts and anterior-posterior axon guidance of commissural axons via Wnt-Frizzled3 signaling (14) (15). Through its interaction with Par6 and Par3, aPKC is required for axon specification of hippocampal neurons by regulating the activity of the microtubule affinity regulating kinase MARK2 on microtubule-associated protein Tau phosphorylation and microtubule assembly (9). During neuronal polarization, aPKC is regulated by dishevelled (Dvl) which mediates Wnt signaling (11). aPKC has been also involved in prosurvival signaling in many different cell types including neural cells (16-23). However, the mechanisms underlying the prosurvival function of aPKC in neurons have not been elucidated. The present disclosure demonstrates that inhibiting aPKC using dominant negative constructs or a myristoylated atypical PKC pseudosubstrate promoted axonal degeneration and neuronal apoptosis. These biochemical studies showed that inhibition of aPKC led to microtubule destabilization by increasing MARK2 activity and Tau phosphorylation, resulting in axon degeneration, and eventually neuronal cell body death through the activation of the JNK-cJun pathway. This is the same signaling mechanism of how aPKC/Par6/Par3 is involved in neuronal polarity and promotes axon elongation (9). Together, these results indicate that aPKC is required for both axon elongation during initial axon development and maintenance by promoting microtubule assembly and stability once axons have formed.

Ryk is an atypical receptor tyrosine kinase that binds Wnts. Interestingly, Ryk mediates axon repulsion during development (24-27) and inhibits axon plasticity in adulthood after traumatic injury (28-33). Blocking Ryk signaling into injured dorsal spinal cord prevents axon retraction and can promote axon regrowth (32). Recently, it was found that Ryk expression was increased in motor neurons and axons of the ventral spinal cord in a mouse model of ALS, at early stage of the disease progression, suggesting that Ryk may be involved in early events that trigger neurodegeneration in ALS (6). In this study, it was first tested whether Ryk regulates aPKC. The findings described herein show that aPKC activity was increased in Ryk KO neurons, suggesting that Ryk might normally inhibit aPKC. This is a novel discovery of the interaction between Ryk and aPKC, which may also be relevant to understand how Ryk mediates axon repulsion.

It was then determined whether blocking Ryk signaling might prevent axonal degeneration induced by aPKC inhibition and neuronal death in Ryk knock-out (KO) mice was analyzed. These studies indicate that inhibiting Wnt/Ryk signaling with specific antibodies or by Ryk KO decreased aPKC-induced axonal degeneration. Because both Ryk and Frizzled3 KO mice die at birth, brain areas that are undergoing neuronal death before birth were explored. It was found that an area of cortex shows clear evidence of neuronal death detectable by aCasp3 staining at E18.5, the retrosplenial cortex (RSP), localized between the neocortex and hippocampus.

Consistent with the proposed role of Ryk in promoting degeneration, apoptosis was decreased in E18.5 Ryk KO embryos. Furthermore, it was found that apoptosis was greatly increased in Frizzled3 KO embryos in the RSP at E18.5 and this increase was significantly attenuated in $Ryk^{+/-}$ $Frizzled3^{-/-}$ embryos, revealing a genetic interaction between Frizzled3 and Ryk. It should be noted that there are 10 Frizzleds in the mouse genome. The fact that only the RSP showed clear increase of aCasp3 immunoreactivity suggests significant functional redundancy among the Frizzled family members in cortical neuronal protection at this stage. It cannot be exclude that other areas of the brain would show increased cell death at later time points, including neonatal stage. In Frizzled3 KO embryos, only the RSP region of the cortex showed strong increase of death (5 fold), further suggesting this area being the most vulnerable before birth. Interestingly, when Ryk was reduced by half, the increase of death was significantly reduced.

This genetic interaction between the two opposite Wnt receptors which regulate aPKC in opposite ways further underlie the important role of aPKC and the complex function of Wnts in regulating neuronal survival. This is also consistent with a recent study showing that Frizzled3 is required for spinal cord motor axon survival after initial axon outgrowth (52). Another recent study also shows that planar cell polarity signaling pathway mediates axon guidance and aPKC is involved in amplifying planar cell polarity signaling in growth cone guidance (53) (15). Studies show that Ryk inhibits planar cell polarity signaling (54) (55). Here, the data shows that Ryk and aPKC play opposite roles in mediating axon and neuronal survival. These findings, therefore, will help untangle the intricate molecular signaling pathways that the nervous system uses to carefully assemble neural circuits and the disruption of which may underlie neurological/neurodegenerative disorders.

Method for Inhibiting Neuron Degeneration

Accordingly, the present invention provides methods and compositions for modulating growth of a nerve cell by contacting the neuron with an agent, thereby inhibiting degeneration of a neuron. In various embodiments, the agent may be an anti-Ryk monoclonal antibody or antibody fragment that specifically binds to a binding domain of Wnt affecting a Wnt signaling pathway. These methods and compositions can be used in a wide variety of therapeutic contexts where nerve growth and regeneration would be beneficial. For example, an anti-Ryk antibody or antibody fragment affecting a Wnt signaling pathway can be used to stimulate axonal growth of a damaged neuron along the A-P axis of a patient with SCI. Because it has also been observed that the Wnts are expressed in the several regions in the brain and the components of the Wnt signaling pathways are also present in axons of other central nervous system neurons, it is possible that the anti-Ryk antibody or antibody fragments described herein can be used to modulate growth and directional guidance of axons in the central nervous system.

In some embodiments, the methods as described herein result in at least a 10% decrease (e.g., at least 15%, 20%, 25%, 30%, 35%, 40%, 45%, 50%, 55%, 60%, 65%, 70%, 75%, 80%, 85%, 90%, or even 100% decrease) in the degeneration of a population of neurons or in the degeneration of axons or cell bodies or dendrites of a neuron in a population of neurons as compared to a control population of neurons. In some embodiments, the methods as described herein result at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in the number of neurons (or neuron bodies, axons, or dendrites thereof) that degenerate in a subject compared to the number of neurons (or neuron bodies, axons, or dendrites thereof) that degenerate in a subject that is not administered the one or more of the agents described herein. In some embodiments, the methods as described herein result in at least a 10% decrease (e.g., at least 15%, 20%, 25%, 30%, 35%, 40%, 45%, 50%, 55%, 60%, 65%, 70%, 75%, 80%, 85%, 90%, or even 100% decrease) in one or more (e.g., 1, 2, 3, 4, 5, 6, 7, 8, or 9) symptoms of a neurological/neurodegenerative disease or disorder and/or condition. In some embodiments, the methods as described herein result in at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in the likelihood of developing a neurological/neurodegenerative disease or disorder and/or condition.

The methods of inhibiting neuron degeneration include in vitro, in vivo, and/or ex vivo methods. In some embodiments, the methods are practiced in vivo, i.e., the agent inhibiting neuron degeneration is administered to a subject. In some embodiments, the methods are practiced ex vivo, i.e., neurons to be treated form part of a nerve graft or a nerve transplant in a subject. In some embodiments, the methods are practiced in vitro.

The methods of inhibiting neuron degeneration can be used to inhibit or prevent neuron degeneration in patients newly diagnosed as having a neurological/neurodegenerative disease or disorder or at risk of developing a new neurological/neurodegenerative disease or disorder. On the other hand, the methods of inhibiting neuron degeneration can also be used to inhibit or prevent further neuron degeneration in patients who are already suffering from, or have symptoms of, a neurological/neurodegenerative disease or disorder. Preventing neuron degeneration includes decreasing or inhibiting neuron degeneration, which may be characterized by complete or partial inhibition of neuron degeneration. This can be assessed, for example, by analysis of neurological function.

Spinal Cord Injury (SCI)

A large proportion of spinal cord injury patients have incomplete lesions, where parts of the spinal cord tissues remain intact. Due to the strong inhibitory environment in the injured adult spinal cord, especially in the glial scar, and reduced growth potential of adult axons, the original connections are usually not restored. Nonetheless, the complex circuitry can undergo remodeling to achieve variable levels of functional recovery with rehabilitative training.

Functional restoration of the corticospinal motor system after spinal cord injury is of principal importance since it is essential for recovery of voluntary motor control. In rodents, however, the role of the corticospinal tract (CST) is more limited, with little effect on locomotion and hindlimb usage. Nevertheless, the CST is crucial for skilled forelimb motor control. Fine motor skills are lost after a dorsal column lesion of the main CST, with a varying extent of spontaneous recovery.

In order to understand how neural circuits reorganize to regain function after injury, functional, anatomical and behavioral analyses were performed. The present disclosure demonstrates that the motor cortex remaps such that the cortical areas are no longer used for the hindlimb are recruited to control the forelimb to achieve functional recovery after a dorsal column lesion and this reorganization requires continued training. The present disclosure also shows that removing Ryk, a receptor to axon guidance cues Wnts, results in greater CST axon plasticity and cortical circuit remodeling in conjunction with rehabilitative training, leading to maximal functional restoration. The more gradual and persistent changes in cortical control maps observed in Ryk conditional knockout injured mice are likely due to the enhanced changes in connectivity within the spinal cord and cortical circuits that occur in the absence of Wnt-Ryk signaling. It was previously found that Wnt-Ryk signaling controls topographic map formation in the developing visual system. The present disclosure reveals a novel function of Wnt-Ryk signaling in controlling motor cortex remapping after spinal cord injury in adulthood.

Figure 13A:
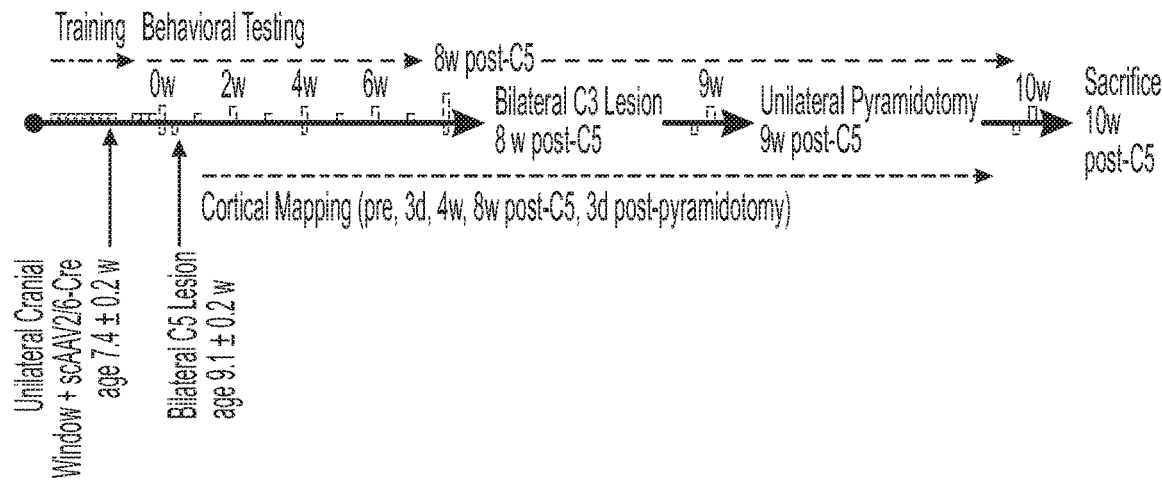
FIGS. 13A-13C are graphical diagrams showing cortical map re-organization during recovery from spinal cord injury.
Figure 13B:
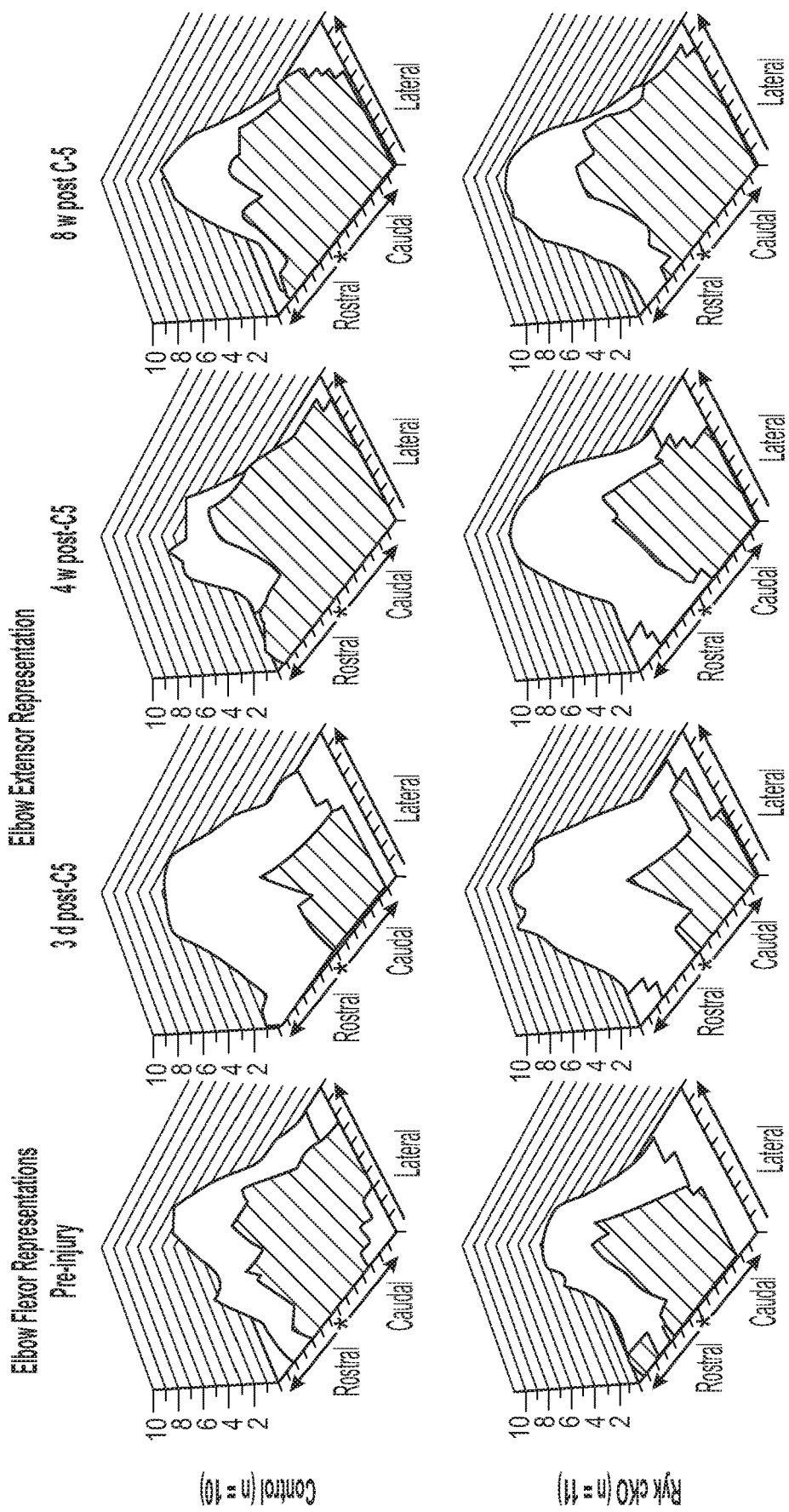
Figure 13C:
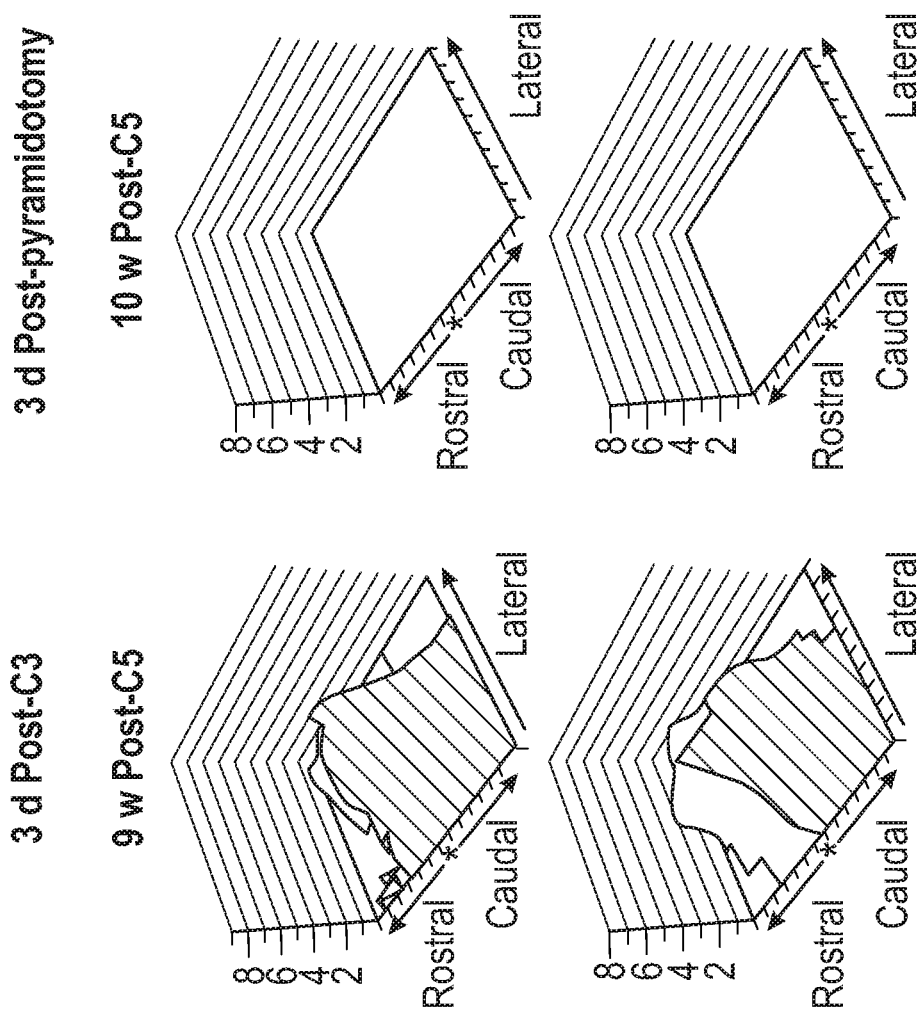

Previous work has demonstrated that the Wnt signaling, which regulates axon guidance in development, has a profound effect on axon plasticity after injury in the adult spinal cord. The motor output map was characterized after spinal cord injury and therefore forelimb motor maps spread into adjacent regions affected by the injury. It was observed that an expansion of flexor control area caudally and medially towards cortical regions originally responsible for hindlimb movements (FIGS. 7A, 7B, 13A and 13B). These changes are likely stereotypical, because wrist flexor representations exhibited a medial shift as they recovered, similar to observed shifts of digit representations in primates (FIGS. 7A, 13A and 13B).

To specifically test the function of Wnt-Ryk signaling in neurons, a conditional allele of Ryk was generated encoding a repulsive Wnt receptor, motor cortex specific knockout was performed and then the dorsal columns at cervical level 5 (C5) were lesioned. Following Ryk conditional knockout, mice recovered on a skilled forelimb reaching task to 81±7% of peak pre-injury levels at 12 weeks after dorsal column lesion, compared to only 60±5% in wild type control mice. This additional recovery depends on the segment of the main CST immediately rostral to the lesion (C3-C5), as a second dorsal column lesion at C3 reduces the functional recovery to control levels. Anatomical analyses showed significantly increased collateral sprouting of CST above and below the C5 injury and with pre-synaptic puncta in these axon sprouts.

Using an optogenetic approach, the output map of the motor cortex was monitored. It was found that immediately after C5 dorsal column lesion, forelimb elbow flexion can be activated by a much larger cortical area, whereas forelimb extension was lost. Over time, the area that activates forelimb flexion reduced back to the original size and a new area, which used to activate the hind limb, was recruited to activate forelimb extension. After the second lesion at C3, the control of forelimb flexion was lost but that of the new control of the forelimb extension was largely unaffected. In Ryk cKO, these changes are more gradual and persistent. Finally, mice that did not undergo weekly behavioral testing displayed only limited skilled forelimb recovery with performance similar to that of mice tested at one week after injury. In the absence of weekly testing, refinement of cortical motor maps was also impaired, irrespective of Ryk conditional deletion, highlighting the importance of targeted plasticity.

Figure 2A:
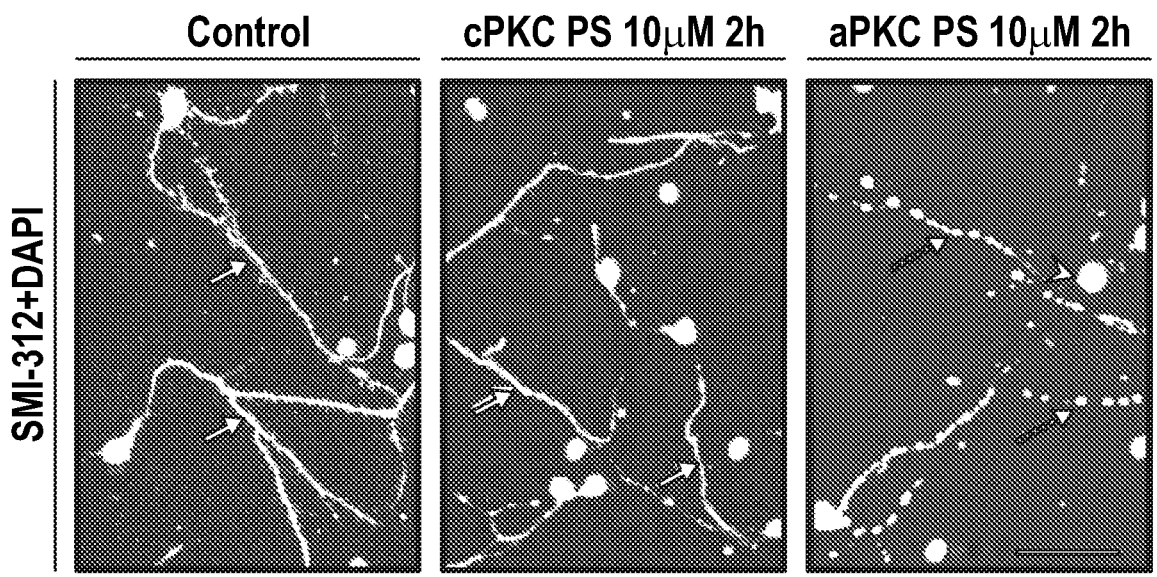
Figure 2F:
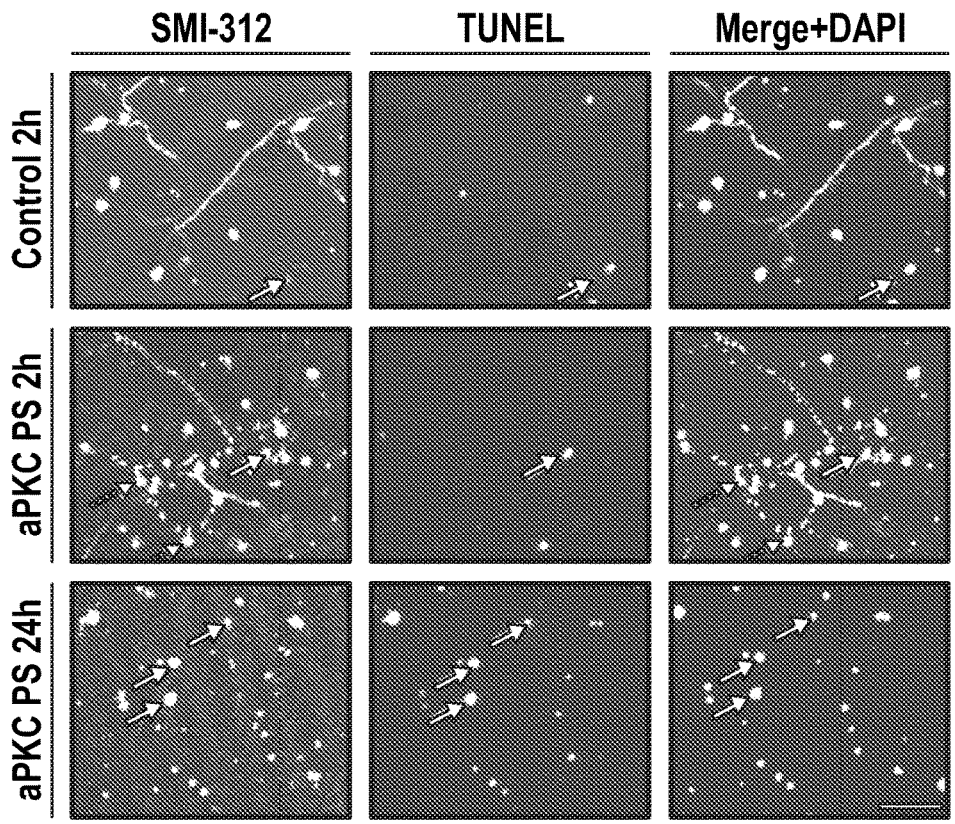
Figure 2H:
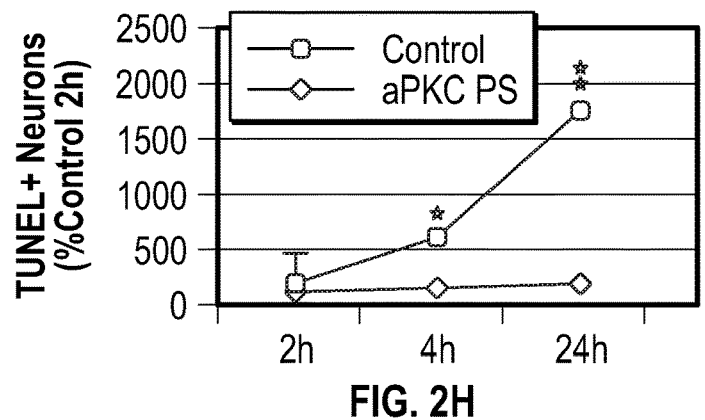
Figure 3A:
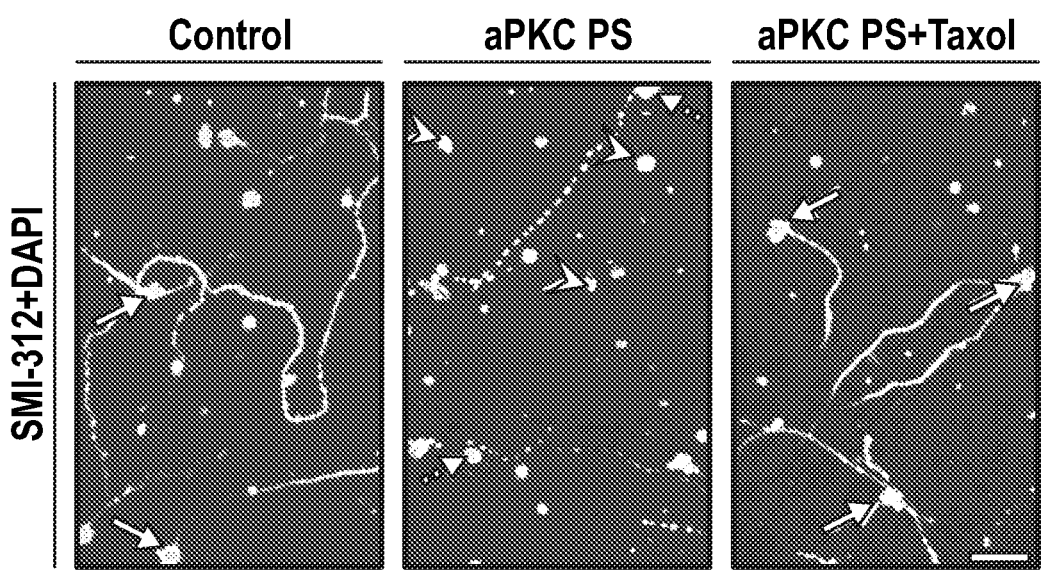
FIGS. 3A-3I are pictorial and graphical diagrams showing that inhibition of aPKC destabilizes microtubules through regulation of MARK2 activity and Tau phosphorylation.
Figure 3B:
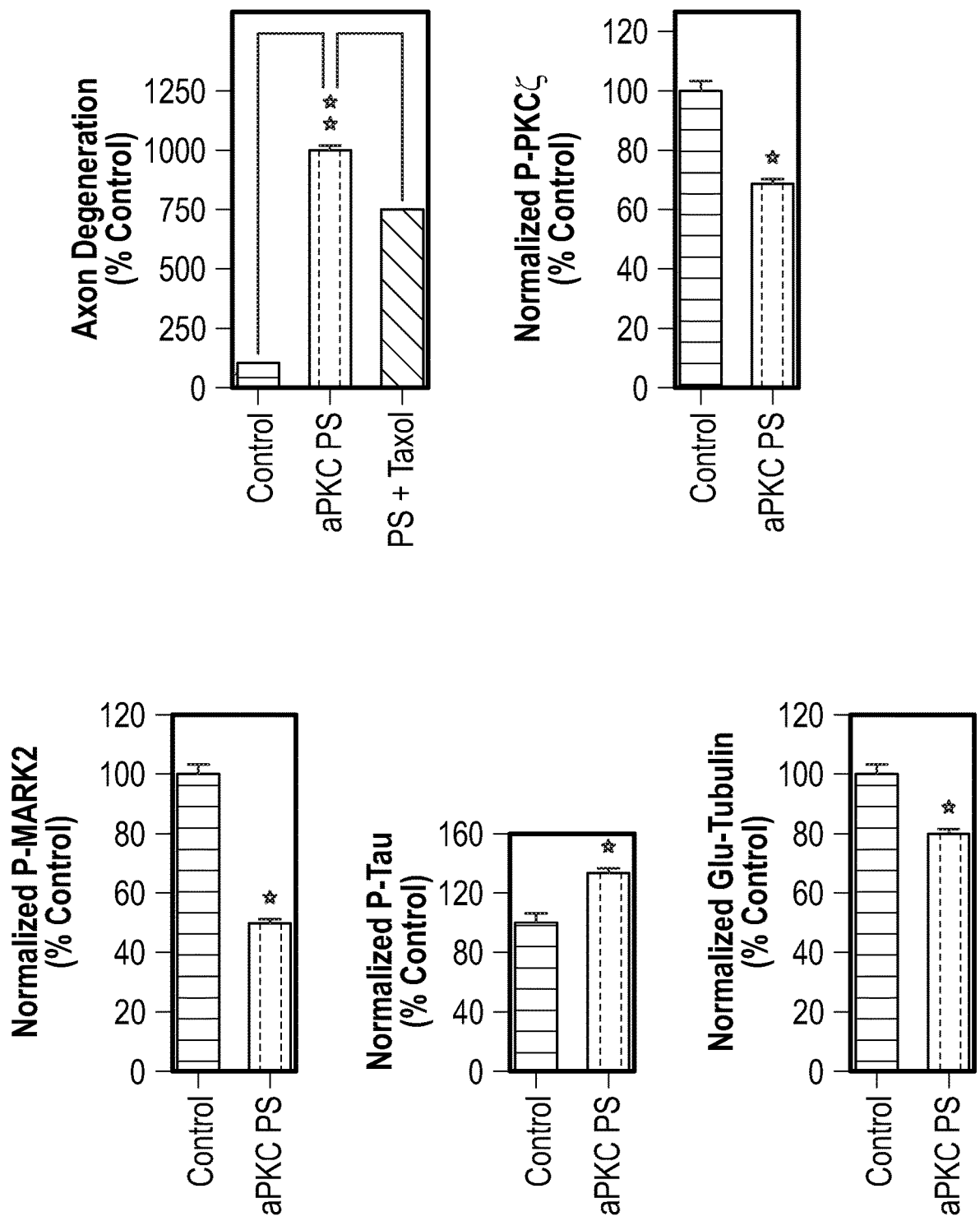
Figure 3C:
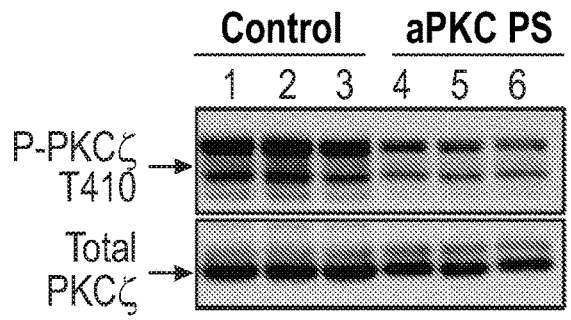
Figure 3D:
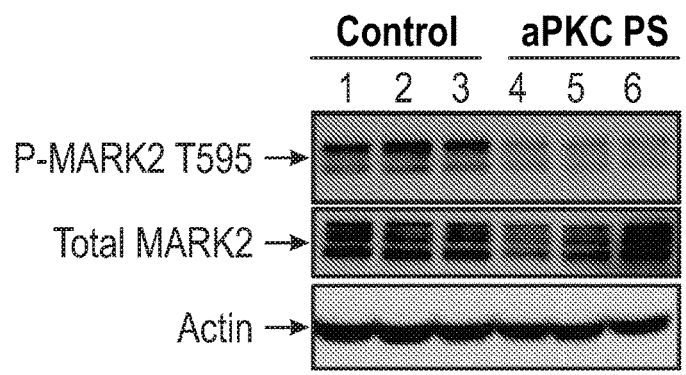

Alterations of motor output maps have been noted in spinal cord injury patients for many years but the neural circuit mechanisms remain unknown. It is known that naive transected hindlimb-projecting corticospinal neurons sprout into cervical spinal cord as early as one week post spinal cord injury. However, it is unlikely that early expansion of motor maps above the level of the injury, which was observed only 3 days later, was due to sprouting and establishment of new connectivity patterns; rather, without being bound by theory, it is likely due to a loss of lateral inhibition within the cortex. However, by 4 weeks after spinal cord injury cortical maps likely reflect the output to the remodeled corticospinal circuitry in the cervical spinal cord. It was observed that the greater CST axon collateral numbers induced following Ryk deletion leads to slight increase of connections with motor units distal to the injury site but robust increase with those rostral to the injury (FIGS. 2H and 3D). Therefore, the changes in connectivity above the level of injury could be the main source for the changes of cortical maps (FIG. 7F). For example, the initial expansion of the biceps at 4 weeks post-injury, and subsequent reduction at 8 weeks, may result from an initial sprouting of CST collaterals that normally project to forelimb motor units in the cervical spinal cord, followed by a subsequent pruning through Hebbian competition. The recruitment of the hindlimb cortical areas for triceps control may result from de novo connections from corticospinal neurons that originally controlled the hindlimb to the forelimb motor units of the cervical spinal cord. These sprouts may either directly contact motor units or form relays using propriospinal neurons. Conditional deletion of Ryk in corticospinal neurons enhances collateral sprouts and thus recruits more spinal cord circuitry, a process that likely underlies greater recovery of voluntary skilled forelimb control. The results of the antibody infusion experiments in the spinal cord suggest that circuit remodeling in the cervical spinal cord is sufficient to promote functional recovery. However, it is plausible that connectivity changes within the primary motor cortex also contribute to the remodeling of the entire circuit.

Other descending pathways are also involved in fine motor control and can partially compensate for the loss of CST input on a skilled forelimb reach task. Additionally, animals with incomplete lesion of the pyramids have been shown to exhibit similar success rates of skilled forelimb reach to intact control animals through compensatory forelimb movements, indicating that a small proportion of spared CST is capable of restoring full, if altered, function on the skilled forelimb reach task. In 59% of the Ryk cKO mice and 100% of Ryk monoclonal antibody-infused animals, recovery of skilled forelimb reach to levels at or above peak pre-injury levels was observed. This full recovery clearly requires the novel CST connections rostral to the lesion, as a second C3 lesion abolishes the enhanced recovery. While the CST is not the sole component mediating control of skilled forelimb reach, it is required for the recovered function as pyramidotomy in the mouse model described herein completely abolished the reaching and grasping behavior. These results suggest that restoring at least some CST function is a critical component in recovery of motor control after injury as compensatory plasticity of other tracts drives limited recovery in rodents, which are less dependent upon the CST for motor control than primates.

The present disclosure also demonstrates that a Ryk monoclonal antibody can be a therapeutic tool as blocking Ryk function after lesion leads to improved functional recovery. It has been shown here that maximal recovery of the forelimb can be achieved by combining targeted plasticity for the forelimb function (continued reaching and grasping training) and molecular manipulation. Therefore, it is anticipated that combining targeted plasticity of other functions with molecular manipulation may allow recovery of other motor or sensory functions. A large proportion of patients have incomplete spinal cord injuries, providing a substrate for recovery. This disclosure illustrates that promoting circuit plasticity is a promising approach to restore maximal function following incomplete spinal cord injury.

Wnt Peptides

Wnts are secreted cysteine-rich glycosylated proteins that play a role in the development of a wide range of organisms. Wnts are thought to function in a variety of developmental and physiological processes since many diverse species have multiple conserved Wnt genes (McMahon, 1992; Nusse and Varmus, 1992). The Wnt growth factor family includes at least 19 genes identified in mammals, including Wnt1, Wnt2, Wnt2b, Wnt3, Wnt3a, Wnt4, Wnt5a, Wnt5b, Wnt 6, Wnt7a, Wnt7b, Wnt8Wnt8b, Wnt9a, Wnt9b, Wnt10a, Wnt10b, Wnt11, and Wnt16. Similar numbers of Wnt genes are present in other vertebrate species (see, e.g., US Pub. No. 2011/0065645, incorporated herein by reference in its entirety). Of course, further Wnts may be discovered and/or characterized in the future, and those of skill will be able to employ any such Wnts in the context of the invention. Further, those of skill will be able to use the teachings herein to obtain and use Wnts of any species in the context of the invention.

Anti-Ryk Antibodies

Antibodies of the invention can be administered by any suitable means, including parenteral, subcutaneous, intraperitoneal, intrapulmonary, intranasal, and, if desired for local treatment, intralesional administration. Parenteral infusions include intramuscular, intravenous, intraarterial, intraperitoneal, and subcutaneous administration. In addition, antibodies can be administered by pulse infusion, particularly with declining doses of the antibody. Dosing can be by any suitable route, e.g., by injections, such as intravenous or subcutaneous injections, depending in part on whether the administration is brief or chronic.

As used herein, the term "antibody" is used in its broadest sense to include polyclonal and monoclonal antibodies, as well as antigen binding fragments of such antibodies. Antibodies are characterized, in part, in that they specifically bind to an antigen, particularly to one or more epitopes of an antigen. The term "binds specifically" or "specific binding activity" or the like, when used in reference to an antibody, means that an interaction of the antibody and a particular epitope has a dissociation constant of at least about $1 \times 10^{-6}$ M, generally at least about $1 \times 10^{-7}$ M, usually at least about $1 \times 10^{-8}$ M, and particularly at least about $1 \times 10^{-9}$ M or $1 \times 10^{-10}$ M or less. As such, Fab, F(ab')$_2$, Fd and Fv fragments of an antibody that retain specific binding activity are included within the definition of an antibody.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., Science 246:1275-1281, 1989, which is incorporated herein by reference). These and other methods of making, for example, chimeric, humanized, CDR-grafted, single chain, and bifunctional antibodies are well known (Winter and Harris, Immunol. Today 14:243-246, 1993; Ward et al., Nature 341:544-546, 1989; Harlow and Lane, Antibodies: A laboratory manual (Cold Spring Harbor Laboratory Press, 1999); Hilyard et al., Protein Engineering: A practical approach (IRL Press 1992); Borrabeck, Antibody Engineering, 2d ed. (Oxford University Press 1995); each of which is incorporated herein by reference). In addition, modified or derivatized antibodies, or antigen binding fragments of antibodies, such as pegylated (polyethylene glycol modified) antibodies, can be useful for the present methods.

Antibodies can be tested for anti-target polypeptide activity using a variety of methods well-known in the art. Various techniques may be used for screening to identify antibodies having the desired specificity, including various immunoassays, such as enzyme-linked immunosorbent assays (ELISAs), including direct and ligand-capture ELISAs, radioimmunoassays (RIAs), immunoblotting, and fluorescent activated cell sorting (FACS). Numerous protocols for competitive binding or immunoradiometric assays, using either polyclonal or monoclonal antibodies with established specificities, are well known in the art. Such immunoassays typically involve the measurement of complex formation between the target polypeptide and a specific antibody. A two-site, monoclonal-based immunoassay utilizing monoclonal antibodies reactive to two non-interfering epitopes on the target polypeptide is preferred, but other assays, such as a competitive binding assay, may also be employed. See, e.g., Maddox et al, 1983, J. Exp. Med. 158:1211.

The location of the binding target of an antibody used in the invention can be taken into consideration in preparation and administration of the antibody. When the binding target is an intracellular molecule, certain embodiments of the invention provide for the antibody or antigen-binding fragment thereof to be introduced into the cell where the binding target is located. In one embodiment, an antibody of the invention can be expressed intracellularly as an intrabody. The term "intrabody," as used herein, refers to an antibody or antigen-binding portion thereof that is expressed intracellularly and that is capable of selectively binding to a target molecule, as described in Marasco, Gene Therapy 4:11-15, 1997; Kontermann, Methods 34:163-170, 2004; U.S. Pat. Nos. 6,004,940 and 6,329,173; U.S. Patent Application Publication No. 2003/0104402, and PCT Publication No. WO 03/077945. Intracellular expression of an intrabody is effected by introducing a nucleic acid encoding the desired antibody or antigen-binding portion thereof (lacking the wild-type leader sequence and secretory signals normally associated with the gene encoding that antibody or antigen-binding fragment) into a target cell. Any standard method of introducing nucleic acids into a cell may be used, including, but not limited to, microinjection, ballistic injection, electroporation, calcium phosphate precipitation, liposomes, and transfection with retroviral, adenoviral, adeno-associated viral and vaccinia vectors carrying the nucleic acid of interest.

In another embodiment, internalizing antibodies are provided. Antibodies can possess certain characteristics that enhance delivery of antibodies into cells, or can be modified to possess such characteristics. Techniques for achieving this are known in the art. For example, cationization of an antibody is known to facilitate its uptake into cells (see, e.g., U.S. Pat. No. 6,703,019). Lipofections or liposomes can also be used to deliver the antibody into cells. Where antibody fragments are used, the smallest inhibitory fragment that specifically binds to the binding domain of the target protein is generally advantageous. For example, based upon the variable-region sequences of an antibody, peptide molecules can be designed that retain the ability to bind the target protein sequence. Such peptides can be synthesized chemically and/or produced by recombinant DNA technology (see, e.g., Marasco et al., Proc. Natl. Acad. Sci. U.S.A. 90:7889-7893, 1993).

Entry of modulator polypeptides into target cells can be enhanced by methods known in the art. For example, certain sequences, such as those derived from HIV Tat or the Antennapedia homeodomain protein are able to direct efficient uptake of heterologous proteins across cell membranes (see, e.g., Chen et al., Proc. Natl. Acad. Sci. U.S.A. 96:4325-4329, 1999).

When the binding target is located in the brain, certain embodiments of the invention provide for the antibody or antigen-binding fragment thereof to traverse the blood-brain barrier. Certain neurological/neurodegenerative diseases are associated with an increase in permeability of the blood-brain barrier, such that the antibody or antigen-binding fragment can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the antibody or antigen-binding fragment across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford Pharmaceutical). Methods of creating openings in the barrier include, but are not limited to, ultrasound (see, e.g., U.S. Pub. No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody or antigen-binding fragment (see, e.g., U.S. Pub. No. 2003/0083299).

Lipid-based methods of transporting the antibody or antigen-binding fragment across the blood-brain barrier include, but are not limited to, encapsulating the antibody or antigen-binding fragment in liposomes that are coupled to antibody binding fragments that bind to receptors on the vascular endothelium of the blood-brain barrier (see, e.g., U.S. Pub. No. 2002/0025313), and coating the antibody or antigen-binding fragment in low-density lipoprotein particles (see, e.g., U.S. Pub. No. 2004/0204354) or apolipoprotein E (see, e.g., U.S. Pub. No. 2004/0131692).

Receptor and channel-based methods of transporting the antibody or antigen-binding fragment across the blood-brain barrier include, but are not limited to, using glucocorticoid blockers to increase permeability of the blood-brain barrier (see, e.g., U.S. Pub. Nos. 2002/0065259, 2003/0162695, and 2005/0124533); activating potassium channels (see, e.g., U.S. Pub. No. 2005/0089473), inhibiting ABC drug transporters (see, e.g., U.S. Pub. No. 2003/0073713); coating antibodies with a transferrin and modulating activity of the one or more transferrin receptors (see, e.g., U.S. Pub. No. 2003/0129186), and cationizing the antibodies (see, e.g., U.S. Pat. No. 5,004,697).

Antibody compositions used in the methods of the invention are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody (when used alone or in combination with other agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g., 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

In some embodiments, different antibody regions are illustrated by reference to IgG, which contains four amino acid chains—two longer length heavy chains and two shorter light chains that are inter-connected by disulfide bonds. The heavy and light chains each contain a constant region and a variable region. A heavy chain is comprised of a heavy chain variable region and a heavy chain constant region. A light chain is comprised of a light chain variable region and a light chain constant region. In various embodiments, there are three hypervariable regions within the variable regions that are responsible for antigen specificity. In various embodiments, the hypervariable regions are referred to as complementarity determining regions (CDR) and are interposed between more conserved flanking regions referred to as framework regions (FW). In various embodiments, the variable regions of the heavy and light chains contain a binding domain that interacts with an antigen.

Accordingly, in one aspect, the invention provides an anti-Ryk antibody and functional fragments thereof that inhibit Wnt-Ryk signaling. In various embodiments, the antibody is an isolated monoclonal antibody that specifically binds to a binding domain of Wnt to inhibit Wnt-Ryk signaling. Sequence data of the key regions of antibodies of the invention are shown in Tables 2 and 3:

TABLE 2

| Sequence Data of Ab5.5 | | |
|---|---|---|
| SEQ ID NO: | DESCRIPTION | SEQUENCE |
| 1 | CDR of Ab5.5 antibody Light Chain Variable Region | QDINSY |
| 2 | CDR of Ab5.5 antibody Light Chain Variable Region | RAN |
| 3 | CDR of Ab5.5 antibody Light Chain Variable Region | LQYDEFPLT |
| 4 | Ab5.5 antibody Light Chain Variable Region | DIKMTQSPSSMYASLGE RVTITCKAS<u>QDINSY</u>LS WIQQKPGKSPKTLIY<u>RA</u> NRLVDGVPSRFSGSGSG QDYSLTISSLEYEDMGI YYC<u>LQYDEFPLT</u>FGAGT KLELKRADAAPTVSIFP PSSEQLTSGGASVVCFL NNFYPKDINVKWKIDGS ERQNGVLNSWTDQDSKD STYSMSSTLTLTKDEYE RHNSYTCEATHKTSTSP IVKSFNRNEC |

TABLE 2-continued

Sequence Data of Ab5.5

| SEQ ID NO: | DESCRIPTION | SEQUENCE |
|---|---|---|
| 5 | CDR of Ab5.5 antibody Heavy Chain Variable Region | GFTFSSYT |
| 6 | CDR of Ab5.5 antibody Heavy Chain Variable Region | ISNGGGGT |
| 7 | CDR of Ab5.5 antibody Heavy Chain Variable Region | HGDNGDYWG HGSTLTVSS AK |
| 8 | Ab5.5 antibody Heavy Chain Variable Region | EVKLVESGGDLV QPGGSLKLSCAA SGFTFSSYTM SWIRQTPEKRLE WVAYISNGGGGT YYPDTVKGRFTI SRDNAKNTLYLQ MNSLKSEDTAMY YCTRHGDNGDYW GHGSTLTVSSAK TTPPSVYPLAPG SAAQTNSMVTLGC LVKGYFPEPVTVT WNSGSLSSGVHT FPAVLQSDLYTL SSSVTVPSSTWP SETVTCNVAHPA SSTKVDKKIVPR DCGCKPCICTVP EVSSVFIFPPKP KDVLTITLTPKV TCVVVDISKDDP EVQFSWFVDDVE VHTAQTQPREEQ FNSTFRSVSELP IMHQDWLNGKEF KCRVNSAAFPAP IEKTISKTKGRP KAPQVYTIPPPK EQMAKDKVSLTC MITDFFPEDITV EWQWNGQPAENY KNTQPIMDTDGS YPVYSKLNVQKS NWEAGNTFTCSV LHEGLHNHHTEK SLSHSPGK |

TABLE 3

Sequence Data of Ab11.4

| SEQ ID NO: | DESCRIPTION | SEQUENCE |
|---|---|---|
| 9 | CDR of Ab11.4 antibody Light Chain Variable Region | QDINRY |
| 2 | CDR of Ab11.4 antibody Light Chain Variable Region | RAN |
| 3 | CDR of Ab11.4 antibody Light Chain Variable Region | LQYDEFPLT |
| 10 | Ab11.4 antibody Light Chain Variable Region | DIKMTQSPSSMYASL GERVTITCKASQDIN RYLSWFQQKPGKSPE TLIYRANRLVDGVPS RFSGSGSGQDYSLTIS SLEYEDMGIYYCLQYD EFPLTFGAGTKLELKR ADAAPTVSIFPPSSEQ LTSGGASVVCFLNNFY PKDINVKWKIDGSERQ NGVLNSWTDQDSKDST YSMSSTLTLTKDEYER HNSYTCEATHKTSTSP IVKSFNRNEC |
| 5 | CDR of Ab11.4 antibody Heavy Chain Variable Region | GFTFSSYT |
| 11 | CDR of Ab11.4 antibody Heavy Chain Variable Region | ISTGGGST |
| 12 | CDR of Ab11.4 antibody Heavy Chain Variable Region | HGEFNYWGQG TLVTVSAAK |
| 13 | Ab11.4 antibody Heavy Chain Variable Region | EVKLVESGGGLVQPGGS LKLSCAASGFTFSSYTM SWVRQTPEKRLEWVAY ISTGGGSTYYPDTVKGR FTISRDNAKNTLYLQMS SLKSEDTAMYYCARHG EFNYWGQGTLVTVSAAK TTPPSVYPLAPGSAAQ TNSMVTLGCLVKGYFPE PVTVTWNSGSLSSGVHT FPAVLQSDLYTLSSSVT VPSSTWPSETVTCNVAH PASSTKVDKKIVPRDCG CKPCICTVPEVSSVFIF PPKPKDVLTITLTPKVT CVVVDISKDDPEVQFSW FVDDVEVHTAQTQPREE QFNSTFRSVSELPIMHQ DWLNGKEFKCRVNSAAF PAPIEKTISKTKGRPKA PQVYTIPPPKEQMAKDK VSLTCMITDFFPEDITV EWQWNGQPAENYKNTQP IMDTDGSYFVYSKLNVQ KSNWEAGNTFTCSVLHE GLHNHHTEKSLSHSP GK |

Accordingly, the invention provides an antibody that specifically binds to a binding domain of Wnt to inhibit Wnt-Ryk signaling. Thus, in various embodiments, the anti-Ryk antibodies of the present invention include any polypeptide or protein having a binding domain which is, or is substantially identical to the set of CDRs within an antibody variable region described herein that is specific for binding to a Wnt binding domain (e.g., at least about 80% identical, at least about 85% identical, at least about 90% identical, at least about 95% identical, or at least 99% identical to those herein). In particular, the antibody has a light chain variable region having the CDR sequences set forth in SEQ ID NOs: 1-3 or SEQ ID NOs: 9, 2 and 3; and a heavy chain variable region having the CDR sequences set forth in SEQ ID Nos: 5-7 or SEQ ID NOs: 5, 11, and 12.

In various embodiments, the light chain variable region has an amino acid sequence with at least 85% sequence identity to SEQ ID NOs: 4 or 10, optionally at least 90% sequence identity to SEQ ID NOs: 4 or 10. In further embodiments, the light chain variable region has an amino acid sequence having at least 95% sequence identity to SEQ ID NOs: 4 or 10, optionally at least 99% sequence identity to SEQ ID NOs: 4 or 10. In further embodiments, the anti-Ryk antibody Ab5.5 has a light chain variable region with the amino acid sequence set forth in SEQ ID NO: 4. In further embodiments, the anti-Ryk antibody Ab11.4 has a light chain variable region with the amino acid sequence set forth in SEQ ID NO: 10.

In various embodiments, the heavy chain variable region has an amino acid sequence with at least 85% sequence identity to SEQ ID NOs: 8 or 13, optionally at least 90% sequence identity to SEQ ID NOs: 8 or 13. In further embodiments, the heavy chain variable region has an amino acid sequence having at least 95% sequence identity to SEQ ID NOs: 8 or 13, optionally at least 99% sequence identity to SEQ ID NOs: 8 or 13. In further embodiments, the anti-Ryk antibody Ab5.5 has a heavy chain variable region with the amino acid sequence set forth in SEQ ID NO: 8. In further embodiments, the anti-Ryk antibody Ab11.4 has a heavy chain variable region with the amino acid sequence set forth in SEQ ID NO: 13.

While the heavy chain variable region and light chain variable region may be combined with other light chain variable regions and other heavy chain variable regions respectively, so long as specific binding to a binding domain of Wnt can be maintained to inhibit Wnt-Ryk signaling binding, in some embodiments, the anti-Ryk antibody includes a heavy chain variable region having at least 85% sequence identity to the amino acid sequence set forth in SEQ ID NO: 8, the heavy chain variable region further having three CDR sequences set forth in SEQ ID NOs: 5-7; and a light chain region variable region having at least 85% sequence identity to the amino acid sequence set forth in SEQ ID NO: 4, the light chain variable region also having the three CDR sequences set forth in SEQ ID NOs: 1-3. In some embodiments, the anti-Ryk antibody includes a heavy chain variable region having at least 85% sequence identity to the amino acid sequence set forth in SEQ ID NO: 13, the heavy chain variable region further having three CDR sequences set forth in SEQ ID NOs: 5, 11, and 12; and a light chain region variable region having at least 85% sequence identity to the amino acid sequence set forth in SEQ ID NO: 10, the light chain variable region also having the three CDR sequences set forth in SEQ ID NOs: 9, 2, and 3.

In further embodiments, the heavy chain variable region has at least 90% sequence identity to the amino acid sequence of SEQ ID NO: 8 and the light chain variable region has at least 90% sequence identity to the amino acid sequence of SEQ ID NO: 4. In still further embodiments, the heavy chain variable region has at least 95% sequence identity to the amino acid sequence of SEQ ID NO: 8 and the light chain variable region has at least 95% sequence identity to the amino acid sequence of SEQ ID NO: 4. In still further embodiments, the heavy chain variable region has at least 99% sequence identity to the amino acid sequence of SEQ ID NO: 8 and the light chain variable region has at least 99% sequence identity to the amino acid sequence of SEQ ID NO: 4. In the anti-Ryk antibody AB5.5, the heavy chain variable region has the amino acid sequence of SEQ ID NO: 8 and the light chain variable region has the amino acid sequence of SEQ ID NO: 4.

In further embodiments, the heavy chain variable region has at least 90% sequence identity to the amino acid sequence of SEQ ID NO: 13 and the light chain variable region has at least 90% sequence identity to the amino acid sequence of SEQ ID NO: 10. In still further embodiments, the heavy chain variable region has at least 95% sequence identity to the amino acid sequence of SEQ ID NO: 13 and the light chain variable region has at least 95% sequence identity to the amino acid sequence of SEQ ID NO: 10. In still further embodiments, the heavy chain variable region has at least 99% sequence identity to the amino acid sequence of SEQ ID NO: 13 and the light chain variable region has at least 99% sequence identity to the amino acid sequence of SEQ ID NO: 10. In the anti-Ryk antibody AB11.4, the heavy chain variable region has the amino acid sequence of SEQ ID NO: 13 and the light chain variable region has the amino acid sequence of SEQ ID NO: 10.

As indicated above, the invention encompasses variations in sequence around the CDRs of the antibody within a percent sequence identity. The term "percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two optimally aligned polypeptide sequences are identical. Likewise, 85% amino acid sequence identity means that 85% of the amino acids in two optimally aligned polypeptide sequences are identical; and 90%, 95%, and 99% amino acid sequence identity means that 90%, 95%, and 99% respectively of the amino acids in two optimally aligned polypeptide sequences are identical.

Variations in sequence identity are permitted outside of the CDRs because not all amino acid residues within the heavy and light variable regions are required for binding Ryk at a binding domain of Wnt. In particular regions outside of CDRs, such as framework regions, may be mutated without losing Ryk binding capability. Still further, framework regions may be further mutated and thus vary in sequence when adapting the CDRs for the treatment of different species. Mutations or variations can be described by use of the following nomenclature: position (#); substituted amino acid residue(s). According to this nomenclature, the substitution of, for instance, an alanine residue for a glycine residue at position can be indicated as A#G, where # represents the position. When an amino acid residue at a given position is substituted with two or more alternative amino acid residues, these residues are separated by a comma or a slash. For example, substitution of alanine with either glycine or glutamic acid can be indicated as #G/E, or #G, #E. The deletion of alanine in the same position can be shown as Ala#* or A#* or *#Ala or *#A, where # refers to the position of the amino acid. Multiple mutations are separated by a plus sign or a slash. For example, two mutations in positions (each indicated by "#") substituting alanine and glutamic acid for glycine and serine, respectively, are indicated as A#G+E#S or A#G/E#S. When an amino acid residue at a given position # is substituted with two or more alternative amino acid residues, these residues are separated by a comma or a slash. For example, substitution of alanine at a position # with either glycine or glutamic acid is indicated as A#G,E or A#G/E, or A#G, A#E. When a position # suitable for modification is identified herein without any specific modification being suggested, it is to be understood that any amino acid residue may be substituted for the amino acid residue present in the position. Thus, for instance, when a modification of an alanine at a position # is mentioned but not specified, it is to be understood that the alanine may be deleted or substituted for any other amino acid residue (i.e., any one of R, N, D, C, Q, E, G, H, I, L, K, M, F, P, S, T, W, Y and V).

Referring back to SEQ ID NOs: 1-13, the invention can be defined as a set of CDR regions with anti-Ryk binding activity; however, in preferred embodiments the CDR peptides (each corresponding to a single CDR) are joined to form an anti-Ryk antibody having a variable region for specific binding to a Wnt binding domain. Again, the antibody variable region can be present in, for example, a complete antibody, an antibody fragment (e.g., F(ab), F(ab')$_2$, scFv, minibody, tetrabody and others) or a recombinant derivative of an antibody or antibody fragment. In some aspects, the antibody variable region is present in a recombinant derivative. Examples of recombinant derivatives include single-chain antibodies, diabody, triabody, tetrabody, and miniantibody. In some embodiments, an anti-Ryk antibody also contains one or more variable regions recognizing the same or different epitopes.

In various embodiments, the anti-Ryk antibodies of the invention may contain additional components including, but not limited to, components other than variable regions or additional variable regions that provide, or help provide, useful and/or additional activities. Useful activities include, for example, antibody effector functions such as antibody-dependent cellular cytoxicity, phagocytosis, complement-dependent cytoxicity, and half-life/clearance rate. In some embodiments, antibody effector functions are mediated by different host components, such as Fcγ receptors, neonatal Fc receptor (FcRn), and C1q. In various embodiments, different types of antibody components or alterations are used to enhance effector functions. Examples of useful components or alternations include the use of non-fucosylated oligosaccharides, amino acids altered to have increased stability, amino acids with enhanced binding to FcRn, amino acid alterations with enhanced binding to a Fcγ receptor, and amino acid alterations with decreased binding affinity to a Fcγ receptor.

In various embodiments, the anti-Ryk antibodies of the invention may contain additional components to alter the physiochemical properties of the protein, providing pharmacological advantages. For example, the attachment of polyethylene glycol ("PEG") to molecules, in some embodiments, improves safety by reducing toxicity and increasing efficiency of the molecules when used as therapeutics. Physiochemical alterations include, but are not limited to, changes in conformation, electrostatic binding, and hydrophobicity which can work together to increase systemic retention of a therapeutic agent. Additionally, by increasing the molecular weight of an anti-Ryk antibody or functional fragment thereof by attaching a PEG moiety, pharmacological advantages may include extended circulating life, increased stability, and enhanced protection from host proteases. PEG attachment can also influence binding affinity of the therapeutic moiety to cell receptors. PEG is a non-ionic polymer composed of repeating units ($-O-CH_2-CH_2-$) to make a range of molecular weight polymers from 400 to greater than 15,000 (e.g., PEG polymers with molecular weights of up to 400,000 are commercially available).

Methods for incorporating PEG or long chain polymers of PEG are well known in the art (described, for example, in Veronese, F. M., et al., Drug Disc. Today 10: 1451-8 (2005); Greenwald, R. B., et al., Adv. Drug Deliv. Rev. 55: 217-50 (2003); Roberts, M. J., et al., Adv. Drug Deliv. Rev., 54: 459-76 (2002)), the contents of which is incorporated herein by reference. Other methods of polymer conjugations known in the art can also be used in the present invention.

Thus, the anti-Ryk antibody or functional fragment thereof may be derivatized, linked to or co-expressed with another functional molecule, e.g., another peptide or protein (e.g., a Fab fragment). For example, the antibody can be functionally linked (e.g., by chemical coupling, genetic fusion, noncovalent association or otherwise) to one or more other molecular entities, such as another antibody (e.g., to produce a bispecific or a multispecific antibody), a cytotoxin, cellular ligand or antigen (e.g., to produce an immunoconjugate, such as an immunotoxin). The antibody also can be linked to other therapeutic moieties, e.g., a radioisotope, a small molecule anti-cancer drug, an anti-inflammatory agent, or an immunosuppressive agent. Accordingly, the present invention encompasses a large variety of antibody conjugates, bispecific and multispecific molecules, and fusion proteins, all of which specifically bind to a binding domain of Wnt or specifically bind to the same epitope on Wnt as does a reference antibody or antibody fragment, or cross-competes for specific binding to Wnt with a reference antibody or antibody fragment, as described herein.

Nucleic Acids

Nucleic acid sequences encoding the anti-Ryk polypeptide sequences, which include any of SEQ ID NOs: 1-13 are also provided. Recombinant nucleic acids encoding anti-Ryk antibodies are particularly useful for expression in a host cell that in effect serves as a factory for the anti-Ryk antibodies. In various embodiments, nucleic acids are isolated when purified away from other cellular components or other contaminants (e.g., other nucleic acids or proteins present in the cell) by standard techniques including, including alkaline/SDS treatment, CsCl banding, column chromatography, agarose gel electrophoresis and others well-known in the art. See e.g., F. Ausubel, et al., ed. (1987) Current Protocols in Molecular Biology, Greene Publishing and Wiley Interscience, New York. In various embodiments, a nucleic acid is, for example, DNA or RNA and may or may not contain intronic sequences. In a preferred embodiment, the nucleic acid is a cDNA molecule. In various embodiments, a recombinant nucleic acid provides a recombinant gene encoding the anti-Ryk antibody that exists autonomously from a host cell genome or as part of the host cell genome.

In some embodiments, a recombinant gene contains nucleic acids encoding a protein along with regulatory elements for protein expression. Generally, the regulatory elements that are present in a recombinant gene include a transcriptional promoter, a ribosome binding site, a terminator, and an optionally present operator. A promoter is defined as a DNA sequence that directs RNA polymerase to bind to DNA and initiate RNA synthesis. Antibody associated introns may also be present. The degeneracy of the genetic code is such that, for all but two amino acids, more than a single codon encodes a particular amino acid. This allows for the construction of synthetic DNA that encodes a protein where the nucleotide sequence of the synthetic DNA differs significantly from the nucleotide sequences disclosed herein, but still encodes such a protein. Such synthetic DNAs are intended to be within the scope of the present invention.

Diseases

The anti-Ryk antibodies or antibody fragments described herein can be used in methods for inhibiting neuron (e.g., axon) degeneration. These antibodies or antibody fragments are, therefore, useful in the therapy of, for example, (i) disorders of the nervous system (e.g., neurological/neurodegenerative diseases or disorders), (ii) conditions of the nervous system that are secondary to a disease, condition, or therapy having a primary effect outside of the nervous system, (iii) injuries to the nervous system caused by physical, mechanical, or chemical trauma, (iv) pain, (v) ocular-related neurodegeneration, (vi) memory loss, and (vii) psychiatric disorders. Non-limiting examples of some of these diseases, conditions, and injuries are provided below.

Examples of neurological/neurodegenerative diseases and conditions that can be prevented or treated according to the invention include amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, progressive bulbar palsy, inherited muscular atrophy, invertebrate disk syndromes (e.g., herniated, ruptured, and prolapsed disk syndromes), cervical spondylosis, plexus disorders, thoracic outlet destruction syndromes, peripheral neuropathies, prophyria, mild cognitive impairment, Alzheimer's disease, Huntington's disease, Parkinson's disease, Parkinson's-plus diseases (e.g., multiple system atrophy, progressive supranuclear palsy, and corticobasal degeneration), dementia with Lewy bodies, frontotemporal dementia, demyelinating diseases (e.g., Guillain-Barre syndrome and multiple sclerosis), Charcot-Marie-Tooth disease (CMT; also known as Hereditary Motor and Sensory Neuropathy (HMSN), Hereditary Sensorimotor Neuropathy (HSMN), and Peroneal Muscular Atrophy), prion disease (e.g., Creutzfeldt-Jakob disease, Gerstmann-Straussler-Scheinker syndrome (GSS), fatal familial insomnia (FFI), and bovine spongiform encephalopathy (BSE, commonly known as mad cow disease)), Pick's disease, epilepsy, and AIDS demential complex (also known as HIV dementia, HIV encephalopathy, and HIV-associated dementia).

The methods of the invention can also be used in the prevention and treatment of ocular-related neurodegeneration and related diseases and conditions, such as glaucoma, lattice dystrophy, retinitis pigmentosa, age-related macular degeneration (AMD), photoreceptor degeneration associated with wet or dry AMD, other retinal degeneration, optic nerve drusen, optic neuropathy, and optic neuritis. Non-limiting examples of different types of glaucoma that can be prevented or treated according to the invention include primary glaucoma (also known as primary open-angle glaucoma, chronic open-angle glaucoma, chronic simple glaucoma, and glaucoma simplex), low-tension glaucoma, primary angle-closure glaucoma (also known as primary closed-angle glaucoma, narrow-angle glaucoma, pupil-block glaucoma, and acute congestive glaucoma), acute angle-closure glaucoma, chronic angle-closure glaucoma, intermittent angle-closure glaucoma, chronic open-angle closure glaucoma, pigmentary glaucoma, exfoliation glaucoma (also known as pseudoexfoliative glaucoma or glaucoma capsulare), developmental glaucoma (e.g., primary congenital glaucoma and infantile glaucoma), secondary glaucoma (e.g., inflammatory glaucoma (e.g., uveitis and Fuchs heterochromic iridocyclitis)), phacogenic glaucoma (e.g., angle-closure glaucoma with mature cataract, phacoanaphylactic glaucoma secondary to rupture of lens capsule, phacolytic glaucoma due to phacotoxic meshwork blockage, and subluxation of lens), glaucoma secondary to intraocular hemorrhage (e.g., hyphema and hemolytic glaucoma, also known as erythroclastic glaucoma), traumatic glaucoma (e.g., angle recession glaucoma, traumatic recession on anterior chamber angle, postsurgical glaucoma, aphakic pupillary block, and ciliary block glaucoma), neovascular glaucoma, drug-induced glaucoma (e.g., corticosteroid induced glaucoma and alpha-chymotrypsin glaucoma), toxic glaucoma, and glaucoma associated with intraocular tumors, retinal detachments, severe chemical burns of the eye, and iris atrophy.

Certain diseases and conditions having primary effects outside of the nervous system can lead to damage to the nervous system, which can be treated according to the methods of the present invention. Examples of such conditions include peripheral neuropathy and neuralgia caused by, for example, diabetes, cancer, AIDS, hepatitis, kidney dysfunction, Colorado tick fever, diphtheria, HIV infection, leprosy, lyme disease, polyarteritis nodosa, rheumatoid arthritis, sarcoidosis, Sjogren syndrome, syphilis, systemic lupus erythematosus, and amyloidosis.

In addition, the methods of the invention can be used in the treatment of nerve damage, such as peripheral neuropathy, which is caused by exposure to toxic compounds, including heavy metals (e.g., lead, arsenic, and mercury) and industrial solvents, as well as drugs including chemotherapeutic agents (e.g., vincristine and cisplatin), dapsone, HIV medications (e.g., Zidovudine, Didanosine, Stavudine, Zalcitabine, Ritonavir, and Amprenavir), cholesterol lowering drugs (e.g., Lovastatin, Indapamid, and Gemfibrozil), heart or blood pressure medications (e.g., Amiodarone, Hydralazine, Perhexiline), and Metronidazole.

The methods of the invention can also be used to treat injury to the nervous system caused by physical, mechanical, or chemical trauma. Thus, the methods can be used in the treatment of peripheral nerve damage caused by physical injury (associated with, e.g., burns, wounds, surgery, and accidents), ischemia, prolonged exposure to cold temperature (e.g., frost-bite), as well as damage to the central nervous system due to, e.g., stroke or intracranial hemorrhage (such as cerebral hemorrhage).

Further, the methods of the invention can be used in the prevention or treatment of memory loss such as, for example, age-related memory loss. Types of memory that can be affected by loss, and thus treated according to the invention, include episodic memory, semantic memory, short-term memory, and long-term memory. Examples of diseases and conditions associated with memory loss, which can be treated according to the present invention, include mild cognitive impairment, Alzheimer's disease, Parkinson's disease, Huntington's disease, chemotherapy, stress, stroke, and traumatic brain injury (e.g., concussion).

The methods of the invention can also be used in the treatment of psychiatric disorders including, for example, schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders (e.g., kleptomania, pathological gambling, pyromania, and trichotillomania).

In addition to the in vivo methods described above, the methods of the invention can be used to treat nerves ex vivo, which may be helpful in the context of nerve grafts or nerve transplants. Thus, the compounds provided herein can be useful as components of culture media for use in culturing nerve cells in vitro.

The antibodies or antibody fragments described herein can be optionally combined with or administered in concert with each other or other agents known to be useful in the treatment of the relevant disease or condition. Thus, in the treatment of ALS, for example, the compounds can be administered in combination with Riluzole (Rilutek), minocycline, insulin-like growth factor 1 (IGF-I), and/or methylcobalamin. In another example, in the treatment of Parkinson's disease, inhibitors can be administered with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In a further example, in the treatment of Alzheimer's disease, inhibitors can be administered with acetylcholinesterase inhibitors (e.g., donepezil, galantamine, and rivastigmine) and/or NMDA receptor antagonists (e.g., memantine). The combination therapies can involve concurrent or sequential administration, by the same or different routes, as determined to be appropriate by those of skill in the art. The invention also includes pharmaceutical compositions and kits including combinations as described herein.

In the context of the invention, the terms "contact" or "contacting" are defined to mean any manner in which a compound is brought into a position where it can mediate, modulate, or inhibit the growth of a neuron. "Contacting" can comprise injecting a diffusable or non-diffusable substance into the neuron or an area adjacent a neuron. "Contacting" can comprise placing a nucleic acid encoding a compound into or close to a neuron or non-neuronal cell in a manner such that the nucleic acid is expressed to make the compound in a manner in which it can act upon the neuron. Those of skill in the art, following the teachings of this specification, will be able to contact neurons with substances in any manner.

The methods for modulating growth of a neuron may, in certain embodiments, be methods for stimulating growth of a neuron, methods for regenerating a damaged neuron, or methods for guiding growth of a neuron along the anterior-posterior axis. In other embodiments, the methods for modulating growth of a neuron are further defined as methods for directionally orienting axon growth of a neuron between the spinal cord and the brain.

In certain embodiments, the neuron is contacted with an anti-Ryk monoclonal antibody or antibody fragment that specifically binds to a binding domain of Wnt affecting a Wnt signaling pathway, and may further involve exposing the neuron to a gradient of the anti-Ryk monoclonal antibody or antibody fragment that specifically binds to a binding domain of Wnt affecting a Wnt signaling pathway. The gradient may be in the spinal cord, such as a decreasing anterior-posterior gradient within the spinal cord. In other embodiments, exposing the neuron to the gradient involves stimulating directionally-oriented axon growth of the neuron along the anterior-posterior axis. Any direction of axon growth is contemplated by the present invention. In certain embodiments, the axon growth is directed from the spinal cord to the brain, such as in the growth of neurons in ascending somatosensory pathways. In other embodiments, the axon growth is directed from the brain to the spinal cord, such as in the growth of neurons in descending motor pathways or other regulatory pathways. In further embodiments, the axon growth is directed along the spinothalamic pathway.

The present invention also includes methods of modulating growth of a neuron in a subject, including: (a) providing a composition that includes an anti-Ryk antibody or antibody fragment that specifically binds to a binding domain of Wnt affecting a Wnt signaling pathway; and a pharmaceutical preparation suitable for delivery to the subject; and (b) administering the composition to the subject. The methods for modulating neuron growth of the present invention contemplate measurement of neuronal growth by any known means, as discussed above. For example, the method of modulating neuron growth may be defined as a method of promoting growth and regeneration of a neuron in a subject, a method of promoting axon growth and regeneration in a subject, or a method of promoting directionally-oriented axon growth in a subject. Directionally-oriented axon growth may be along the anterior-posterior axis such as from the spinal cord to the brain, or from the brain to the spinal cord.

In another aspect, the invention provides a composition comprising the antibody or antibody fragment of the invention, which can be prepared for administration to a subject by mixing the antibody or immunogenic peptide fragment with physiologically acceptable carriers or excipients. Such carriers will be nontoxic to recipients at the dosages and concentrations employed. Ordinarily, the preparation of such compositions entails combining the particular antibody with saline, buffers, antioxidants such as ascorbic acid, low molecular weight (less than about 10 residues) polypeptides, proteins, amino acids, carbohydrates including glucose or dextrans, or chelating agents such as EDTA, glutathione and other stabilizers and excipients. Such compositions can be in suspension, emulsion or lyophilized form and are formulated under conditions such that they are suitably prepared and approved for use in the desired application.

A physiologically acceptable carrier or excipient can be any material that, when combined with an immunogenic peptide or a polynucleotide of the invention, allows the ingredient to retain biological activity and does not undesirably disrupt a reaction with the subject's immune system. Examples include, but are not limited to, any of the standard physiologically acceptable carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well-known conventional methods (see, for example, Remington's Pharmaceutical Sciences, Chapter 43, 14th Ed., Mack Publishing Co., Easton Pa. 18042, USA).

For administration to a subject, a peptide, or an encoding polynucleotide, generally is formulated as a composition. Accordingly, the present invention provides a composition, which generally contains, in addition to the peptide or polynucleotide of the invention, a carrier into which the peptide or polynucleotide can be conveniently formulated for administration. For example, the carrier can be an aqueous solution such as physiologically buffered saline or other solvent or vehicle such as a glycol, glycerol, an oil such as olive oil or an injectable organic esters. A carrier also can include a physiologically acceptable compound that acts, for example, to stabilize the peptide or encoding polynucleotide or to increase its absorption. Physiologically acceptable compounds include, for example, carbohydrates, such as glucose, sucrose or dextrans, antioxidants, such as ascorbic acid or glutathione, chelating agents, low molecular weight proteins or other stabilizers or excipients. Similarly, a cell that has been treated in culture for purposes of the practicing the methods of the invention, for example, synovial fluid mononuclear cells, dendritic cells, or the like, also can be formulated in a composition when the cells are to be administered to a subject.

It will be recognized to the skilled clinician that choice of a carrier or excipient, including a physiologically acceptable compound, depends, for example, on the manner in which the peptide or encoding polynucleotide is to be administered, as well as on the route of administration of the composition. Where the composition is administered under immunizing conditions, i.e., as a vaccine, it generally is administered intramuscularly, intradermally, or subcutaneously, but also can be administered parenterally such as intravenously, and can be administered by injection, intubation, or other such method known in the art. Where the desired modulation of the immune system is tolerization, the composition preferably is administered orally, or can be administered as above.

Screening Methods

In another aspect, the invention provides a method of screening for a therapeutic/test/candidate agent for treating a neurological disease or disorder. The method includes administering a test agent to the transgenic non-human mammal described herein and evaluating the effect of the test agent on at least one of: the amount of atypical protein kinases C (aPKC) or MARK2 protein, the level of aPKC or MARK2 activity or the level of aPKC or MARK2 in at least one disease-relevant tissue of the transgenic non-human mammal, wherein at least one of: a decrease in the amount of aPKC protein, an increase in the amount of MARK2 protein, a decrease in the level of aPKC activity, an increase in the level of MARK2 activity, a reduction in the level of aPKC, or an increase in the level of MARK2 in at least one disease-relevant tissue relative to a similar transgenic non-human mammal that does not receive the test agent indicates the test agent is therapeutic for the neurological disease or disorder.

A "test agent" or "candidate agent" refers to an agent that is to be screened in one or more of the assays described herein. The agent can be virtually any chemical compound. It can exist as a single isolated compound or can be a member of a chemical (e.g., combinatorial) library. In one embodiment, the test agent is a small organic molecule. The term small organic molecules refers to molecules of a size comparable to those organic molecules generally used in pharmaceuticals.

Conventionally, new chemical entities with useful properties are generated by identifying a chemical compound (called a "lead compound") with some desirable property or activity, creating variants of the lead compound, and evaluating the property and activity of those variant compounds.

Any agent identified as being a potential therapeutic for treating a neurological disease or disorder may be brought into association with a pharmaceutically acceptable carrier, which constitutes one or more accessory ingredients. The term "pharmaceutically acceptable," when used in reference to a carrier, is meant that the carrier, diluent or excipient must be compatible with the other ingredients of the formulation and not deleterious to the recipient thereof.

Pharmaceutically acceptable carriers useful for formulating an agent for administration to a subject are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the therapeutic agent and on the route of administration of the composition, which can be, for example, orally, intranasally or any other such method known in the art. The pharmaceutical composition also can contain a second (or more) compound(s) such as a diagnostic reagent, nutritional substance, toxin, or therapeutic agent, for example, a cancer chemotherapeutic agent and/or vitamin(s).

The total amount of a compound or composition to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the plasma expander used to treat blood loss in a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

The following examples are intended to illustrate but not limit the invention.

EXAMPLE 1

Methods

Animals—Time-mated pregnant CD1 mice rats were purchased from Charles River. Ryk-deficient mice were obtained from Steven Stacker (Ludwig Institute for Cancer Research, Melbourne, VIC, Australia) (50). Frizzled3-deficient and were obtained from Jeremy Nathans (John Hopkins University, Baltimore, Md.) (51). Genotypes were determined by standard PCR. The day of vaginal plug detection was considered E0.5. Animals were housed in a temperature-controlled room with standard laboratory food and water provided ad libitum.

Antibodies, Reagents and Plasmidic Constructs—Myristoylated aPKC and cPKC pseudosubstrates were purchased from Enzo Life Sciences-Biomol (#BML-P-219 and #BML-P205 respectively).

Monoclonal mouse Ryk antibodies were generated against the ectodomain of Ryk, amino-acids 90-183, fused with maltose binding protein.

Commercial primary antibodies used in this study included P-PKCζ T410 (Santa Cruz sc-101778, rabbit 1:1000), Total PKC (Santa Cruz C-20 sc-216, rabbit, 1:2000), P-MARK2 T595 (Abcam, rabbit 1:1000), Total MARK2 (Abcam, goat 1:1000), SMI-312 (Covance, mouse, 1:1000), MAP2 (Abcam, rabbit 1:1500), βIII-tubulin (Covance, mouse, 1:1000), Rhodamine-phalloidin (Invitrogen, 1:100), P-Tau 5262 (Invitrogen, rabbit, 1:1000), Tau (Taus, Millipore, mouse, 1:2000 for cell culture, 1:4000 for western blotting), P-JNK/SAPK T183/T185 (Cell Signaling, rabbit, 1:1000), Total JNK/SAPK (Cell Signaling, 1:1000), P-c-Jun S63 (Cell Signaling, rabbit 1:1000), Total c-Jun (Cell Signaling, rabbit 1:1000), GAPDH (Millipore-Chemicon, mouse, 1:50,000), actin (mouse, 1:5000), activated Caspase-3 (aCasp3, Cell signaling, rabbit, 1:1000 on cell cultures, 1:500 on tissue sections) and CTIP2 (Abcam, rat, 1:500).

cDNAs of PKCζ-WT, PKCζ-KD (K281W) and PKCζ-T410A plasmidic constructs (56) were cloned into pCIG2-EGFP plasmid (14). pCIG2-Tau-WT and pCIG2-Tau-S262A plasmids were provided by Georges Mairet-Coello (The Scripps Research Institute, La Jolla, Calif.) (57).

Cerebral cortical cell culture—E16.5 mouse pregnant females were sacrificed by $CO_2$ asphyxia and cervical dislocation. Embryos were removed from uterine horns. Skin, skull, and meninges were removed from embryo heads. The cortex was dissected in L-15 medium (Sigma), digested with 0.025% trypsin/0.221 mM EDTA (Mediatech) for 20 min followed by incubation in 5% horse serum prepared in L-15 medium for 5 min to inhibit trypsin. Cortices were mechanically dissociated and cells were plated at 500 cells/mm$^2$ on poly-D-lysine (33.3 µg/ml, Millipore) and laminin (3.3 µg/ml, Invitrogen)-coated 12 mm glass coverslips in 24-well plates or at 1050 cells/mm$^2$ on poly-D-lysine (0.1 mg/ml)-coated 6 well plates (35 mm dishes). Cells were incubated in Neurobasal (Gibco) medium supplemented with B27 (Gibco) containing Glutamax (Gibco), 40 mM Glucose, 100 U/ml penicillin and 1 mg/ml streptomycin (Mediatech). Cultures were maintained in a humidified 5% $CO_2$/air incubator at 37° C.

Magnetofection—For magnetofection, cortices from E17.5 embryos were dissociated in papain (Worthington) supplemented with DNAse I (100 mg/ml, Sigma) for 20 min at 37° C., washed three times and manually triturated in plating medium. Cells were plated at 565/mm$^2$ on 12 mm-glass bottom dishes coated with poly-D-lysine (1 mg/ml, Sigma). Cells were cultured in neurobasal medium supplemented with 2.5% fetal bovine serum (Gemini), B27 (1×), L-glutamine (2 mM) and penicillin (2.5 U/ml)-streptomycin (2.5 mg/ml) (Invitrogen). Neurons were transfected at DIV3 by magnetofection using NeuroMag (OZ Bioscience), according to manufacturer's instructions and as previously described (57). Briefly, 2 µg cDNA was incubated with NeuroMag in neurobasal medium for 15 min at room temperature, and then the mixture was applied dropwise on culture cells. Cultures were placed on magnet for 20 min for transfection. Cotransfections were performed at a 1:1 ratio (w/w).

Immunohistochemistry, Immunocytochemistry and TUNEL assay—Cell cultures were fixed with 4% PFA for 30 min. Embryonic brains were dissected in cold PBS, fixed in 4% PFA for 2 h and incubated overnight in 30% sucrose for cryoprotection. Brains were embedded in a commercial embedding medium (Tissue-Tek, Sakura Finetek), quickly frozen on dry-ice and coronally sectioned at a thickness of 20 µm using a cryostat-microtome (Leica). Sections were mounted on Superfrost Plus slides (Thermo Fisher Scientific) and stored at −20° C. Cells or sections were permeabilized in PBS containing 0.3% triton X-100 (PBS-T) for 10 min and incubated with the primary antibody overnight at 4° C. Monoclonal antibodies were diluted in PBS-T and polyclonal antibodies were diluted in a PBS-T solution containing 10% lactoproteins, 1% bovine serum albumin. Staining was visualized using Alexa Fluor 588 (1:500-1:1000), 594 (1:500-1:1000) or 649 (1:200-1:500) conjugated secondary antibodies (Jackson ImmunoReasearch). For CTIP2 immunodetection, sections were submitted to antigen retrieval procedure in 10 mM citrate buffer pH=6 at 90° C.-95° C. for 10 min. Sections were counterstained with DAPI (Thermo Fisher Scientific). TUNEL was performed using the In situ cell death detection kit TMR red (Roche) according to the manufacturer's instructions.

Western-blotting—Cortical cells cultured in 6 well plates were washed twice with PBS (pH 7.4), scrapped using a rubber policeman and lysed in lysis buffer containing 20 µM Tris-HCl pH7.6, 150 µM NaCl, 0.1% SDS, 1% triton X-100, protease inhibitors (cOmplete mini tablets, Roche Applied Science), phosphatase inhibitors (PhosSTOP, Roche Applied Science). Twenty micrograms of proteins were separated by SDS PAGE and then electro-transferred onto polyvinylidene difluoride membranes (Bio-Rad). Membranes were blocked with blocking buffer containing 2% BSA or 5% fat-free dry milk in Tris-buffered saline solution and Tween 20 (10 mM Tris-HCl pH 7.4, 150 mM NaCl, 0.05% Tween 20) and incubated overnight at 4° C. with primary antibody diluted in blocking buffer. Incubations with HRP conjugated secondary antibodies (1:5000) were performed for 1 h at room temperature and visualization was performed using chemiluminescence (ECL).

Image acquisition and analysis—All images were acquired on an inverted Zeiss LSM510 confocal microscope with LSM acquisition software (Carl Zeiss Microscopy). For quantification of P-PKCζ T410 immunoreactivity in cell cultures, exposure time was adjusted to be under the saturation level for the highest immunofluorescence signal and was conserved between the different samples. Mean immunofluorescence intensity level in neuronal cell bodies was measured using FiJi-ImageJ software (NIH). All quantifications were performed on 10 non-overlapping fields in cell cultures from at least three independent experiments and on four non-consecutive sections from at least three animals for in vivo experiments.

Statistical Analysis—Statistical analyses were performed using ANOVA with Bonferroni Posttest or Student's t test using GraphPad Instat 3.05 (GraphPad Software). All data are expressed as means or percents±s.e.m. *$p<0.05$, $p<0.01$, *$p<0.001$.

EXAMPLE 2

Inhibition of aPKC Promotes Axonal Degeneration and Neuronal Apoptosis

A culture system was established to investigate the expression and role of aPKC in the survival of cerebral cortical neurons. E16.5 cortical cells were cultured for 3 days in vitro (DIV3) and double immunolabeled for the pan-axonal marker SMI-312 and the dendritic marker MAP2. At this stage, most neurons exhibit a long process labeled for SMI-312 corresponding to the axon and few short MAP2+ processes that will give rise to the dendrites. To evaluate the proportion of polarized neurons at this stage, the number of neurons with a long process labeled for SMI-312 and not labeled for MAP2 in its distal part was counted over the total number of SMI-312+ neurons. It was found that 84.2±3.45% of SMI-312+ neurons were polarized in these culture conditions. Then, aPKC expression was investigated in cortical neurons by using an antibody that recognized all isoforms of aPKC family including PKCζ, PKCλ/ι and PKMζ (34). These observations indicate that aPKC immunolabeling was localized in neuronal cell bodies and SMI-312+ axons (FIG. 1A).

Figure 1B:
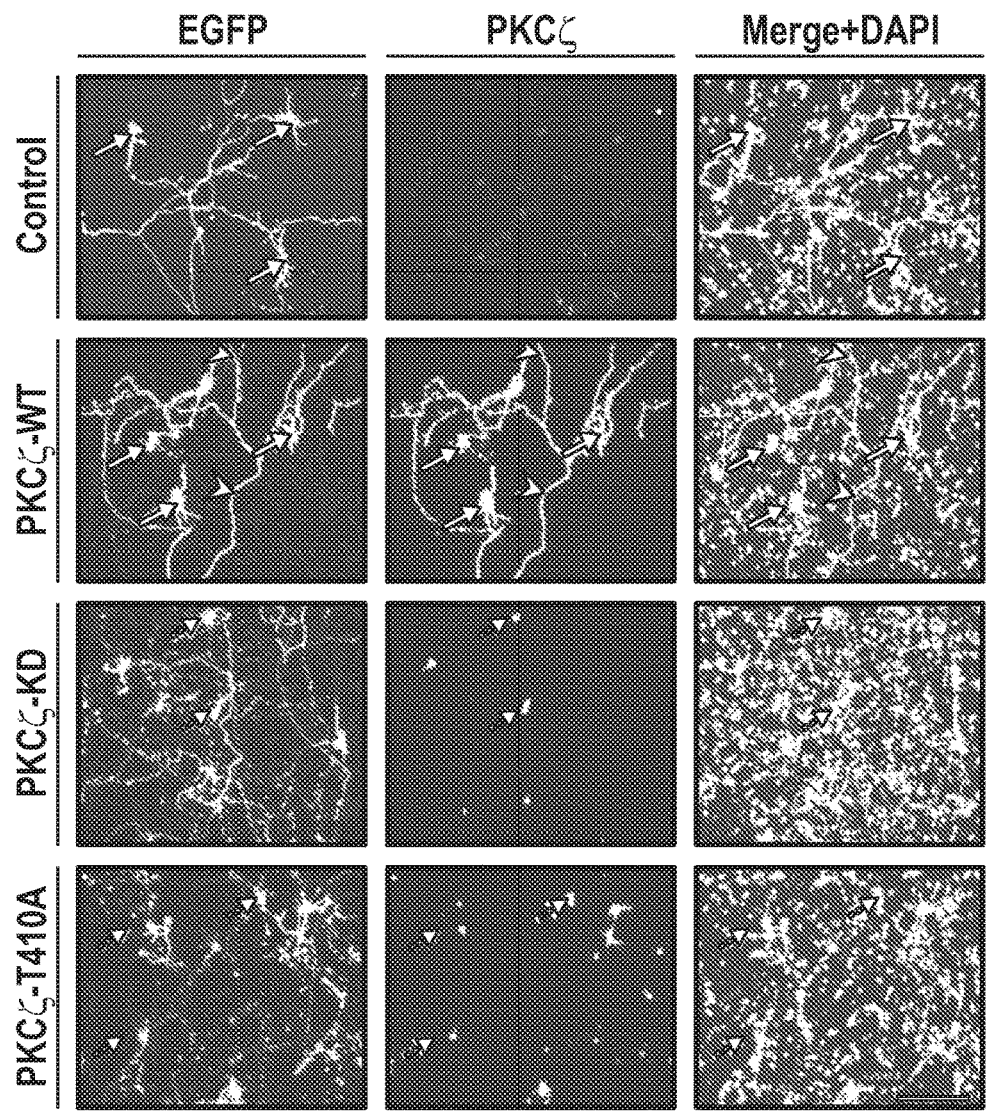
Figure 1C:
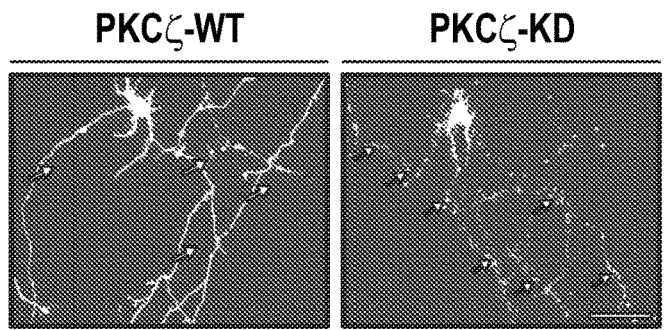
Figure 1D:
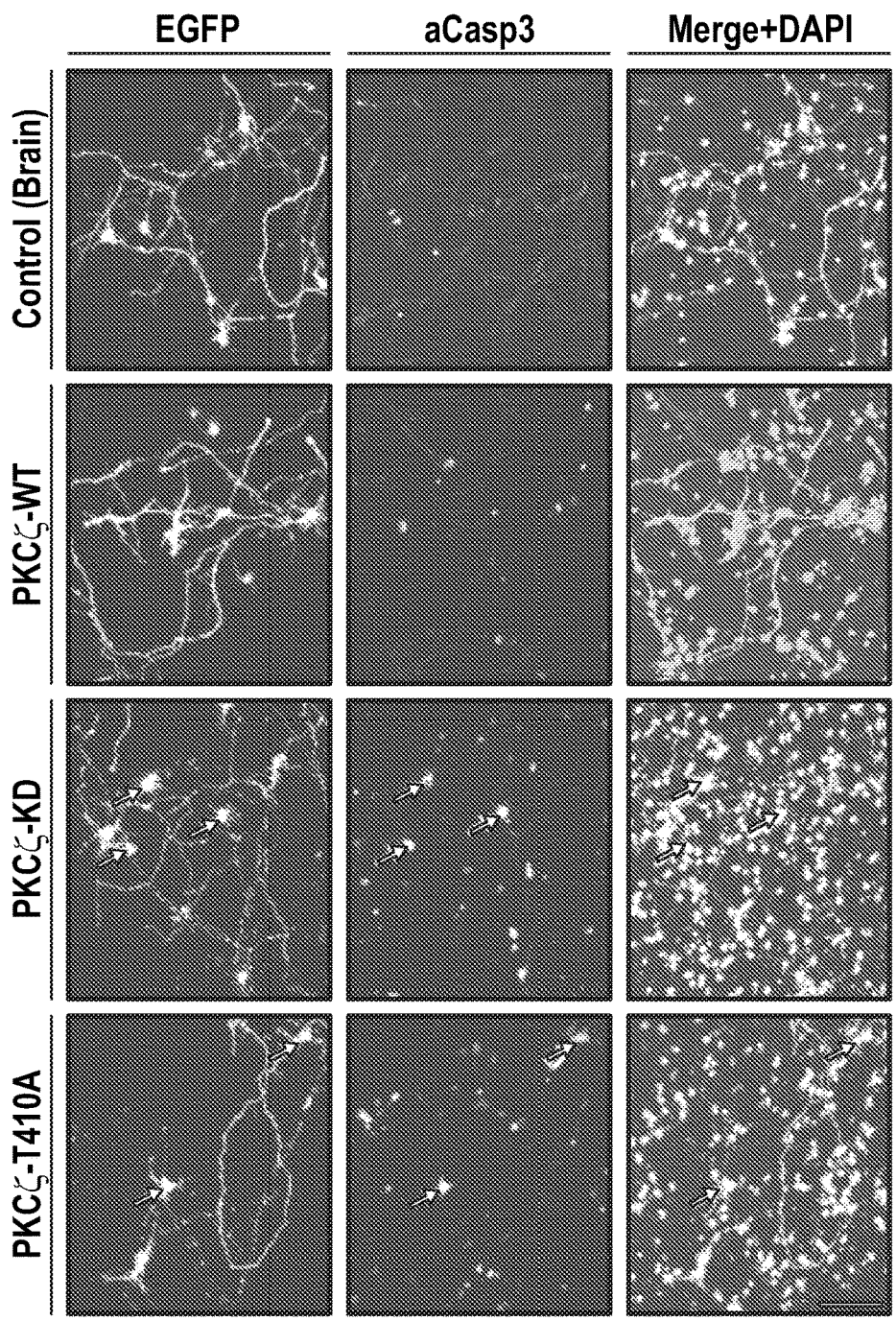
Figure 1E:
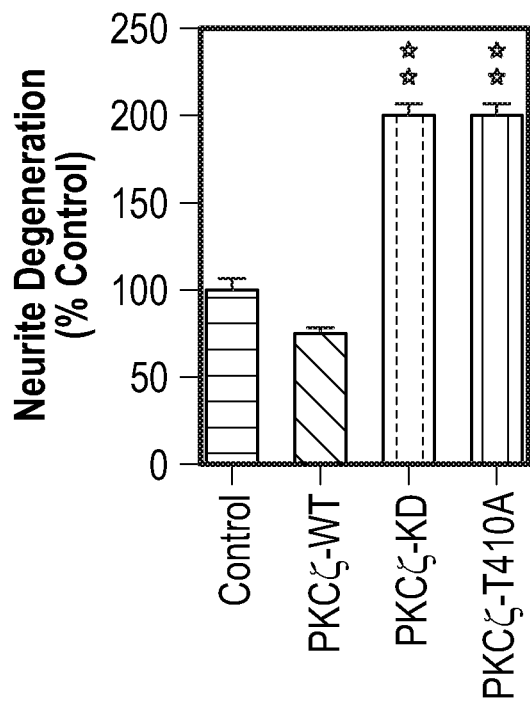
Figure 1F:
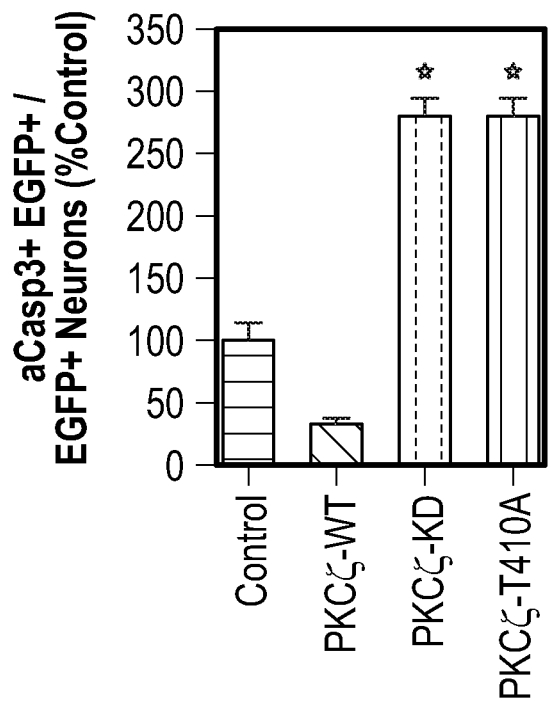

To investigate the role of aPKC in neuronal survival, aPKC activity was inhibited by transfecting a kinase-defective PKCζ (PKCζ-KD) or a nonphosphorylatable mutant (PKCζ-T410A) in cortical neuron cultures. aPKC inhibition by these constructs induced neurite degeneration (FIGS. 1B, 1C, and 1E) after 2 days of transfection, as shown by the massive fragmented neurites of PKCζ-KD and PKCζ-T410A transfected neurons (FIGS. 1B and 1C). PKCζ-KD and PKCζ-T410A overexpression also induced neuronal apoptosis as shown by the increase of the proportion of aCasp3+ neurons (FIGS. 2D and 2F). Overexpression of PKCζ-WT protein did not affect neurite integrity or neuronal survival (FIGS. 1B-1F). The massive axon fragmentation suggests that axons have grown extensively initially and underwent degeneration all at once, suggesting that aPKC is required for axon maintenance. Interestingly, while overexpressed PKCζ was localized in both neuronal cell bodies and neurites, overexpressed PKCζ-KD and PKCζ-T410A mutant proteins were excluded from the processes and were restricted to the cell bodies (FIG. 1B), suggesting that PKCζ activity might regulate its own localization and/or the stability of the protein.

In order to test the role of aPKC in axon survival using an independent method and that allows biochemical analyses, a cell-permeable myristoylated pseudosubstrate specific to aPKC was used (14). As a control, a myristoylated pseudosubstrate specific to conventional PKC (14) was used. The $IC_{50}$ of aPKC and cPKC inhibitors are 10 μM and 8 μM respectively, so a starting dose of 10 μM was used. At this dose, aPKC inhibitor but not cPKC inhibitor promotes rapid axonal degeneration in cortical neurons as shown by the beading aspect of SMI-312+ axons, 2 h after aPKC pseudosubstrate treatment (FIGS. 2A and 2B). Furthermore, aPKC pseudosubstrate promotes axonal degeneration in a dose- (FIG. 2C) and time-dependent manner (FIG. 2D), with an effect starting at 5 μM and as early as 1 h at a dose of 10 μM. To verify the efficacy of aPKC pseudosubstrate, P-PKCζ-T410 immunoreactivity was measured in neuronal cell bodies after 2 h of 10 μM aPKC PS treatment and it was found that it was significantly decreased (FIG. 2E), indicating that aPKC pseudosubstrate decreases (auto)-phosphorylation activity of aPKC.

Figure 2G:
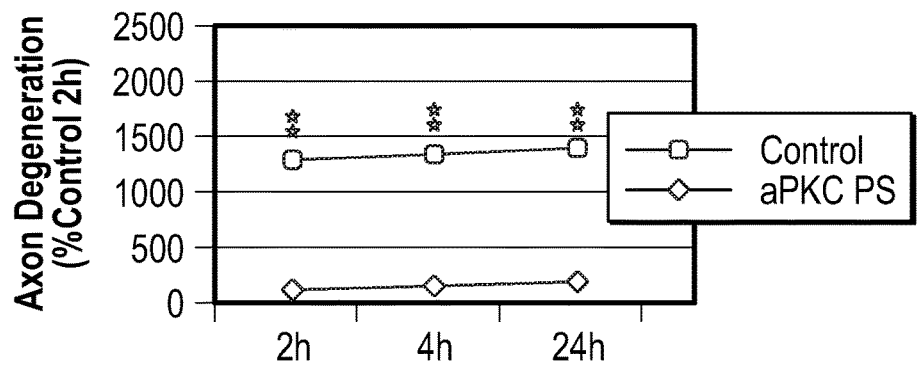
Figure 2I:
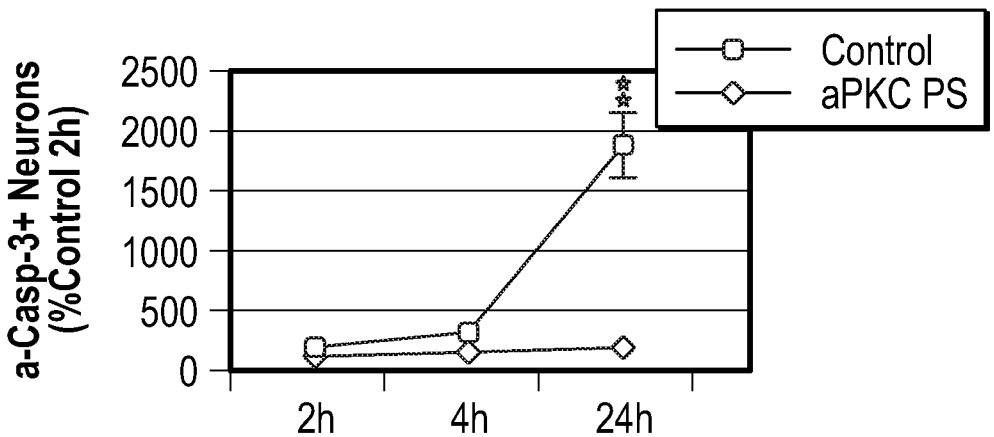

Axon degeneration induced by aPKC pseudosubstrate occurred as early as 1 h (FIG. 2D) and the time course analysis revealed that almost all neurons exhibited degenerating axon or were devoid of axon by 4 h (FIGS. 2F and 2G). In parallel to axon degeneration, neuronal cell body death was measured using TUNEL and activated Caspase-3 staining at 2 h, 4 h and 24 h. It was found that cell death in SMI312+ neurons started at 4 h of incubation with aPKC pseudosubstrate (FIG. 2H), when the quasi-totality of axons had already degenerated (FIG. 2G), suggesting that blocking aPKC signaling triggers a dying back mechanism. Interestingly, neurons started to show aCasp3 after 4 h but all neurons did not express activated Caspase-3 by 24 h (FIG. 2I) while all of them were TUNEL+ by 24 h (FIG. 2H), suggesting that aPKC inhibition may trigger both caspase-3-dependent and -independent cell death pathways.

EXAMPLE 3 aPKC Inhibition Destabilizes Microtubules by Regulating MARK2 Activity and Tau Phosphorylation Microtubule degradation is an early cellular event in axon degeneration process, preceding axonal beading and neurofilament fragmentation (1, 35-37). It was hypothesized that inhibition of aPKC may promote rapid axon degeneration by destabilizing microtubules. To test this hypothesis, cortical neuronal cell cultures were first pre-incubated with taxol, a microtubule stabilizer (38), 2 h prior to and during aPKC pseudosubstrate treatment. Axon degeneration induced by aPKC inhibition was reduced when neuronal cell cultures were pre-treated with taxol (FIGS. 3A and 3B). Using specific markers for the different compartments of the neuronal cytoskeleton (Tau for microtubules, SMI-312 for neurofilaments and rhodamine-phalloidine for F-actin filaments), it was found that microtubules and neurofilaments, but not actin filaments, were disrupted in axons of neurons treated with aPKC pseudosubstrate using confocal microscopy. These observations suggest that aPKC is required for microtubule stability and that aPKC inhibition promotes both microtubule and neurofilament disruption, ultimately leading to axonal degeneration.

Figure 3E:
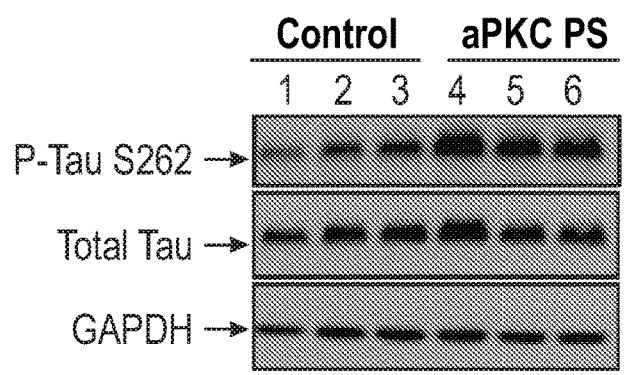
Figure 3F:
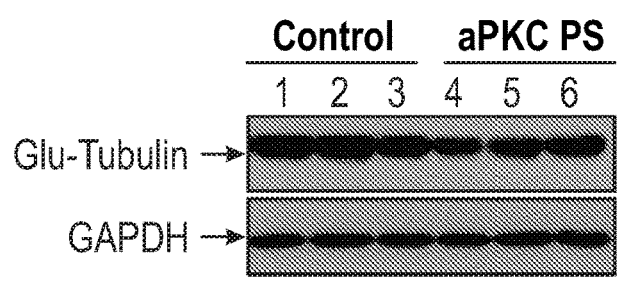

The signaling pathway involved in microtubule destabilization induced by aPKC inhibition was further investigated. First, the efficacy of aPKC pseudosubstrate on blocking aPKC (auto-)phosphorylation activity was confirmed by western blotting. aPKC pseudosubstrate decreased P-PKCζT410 level after 2 h of incubation (FIG. 3C), in agreement with the immunocytochemical analyses (FIG. 2E). Then the focus was on MARK2 because (1) it belongs to the MARK/Par1 family of kinases that were originally discovered to trigger microtubule disassembly (39) and (2) it is inhibited when phosphorylated by aPKC on T595 (40). It was found that aPKC pseudosubstrate treatment reduced phosphorylation of MARK2 on T595 at 2 h (FIG. 3D), indicating that MARK2 activity was increased when aPKC was inhibited. Furthermore, Tau phosphorylation in the microtubule binding domain at S262 (FIG. 3E) was increased at 2 h while stable microtubules, revealed by Glu-Tubulin (FIG. 3F), were decreased. These observations are in agreement with previous studies showing that MARK family kinases destabilize microtubules by phosphorylating MAPs including Tau (9, 39, 41).

Figure 3G:
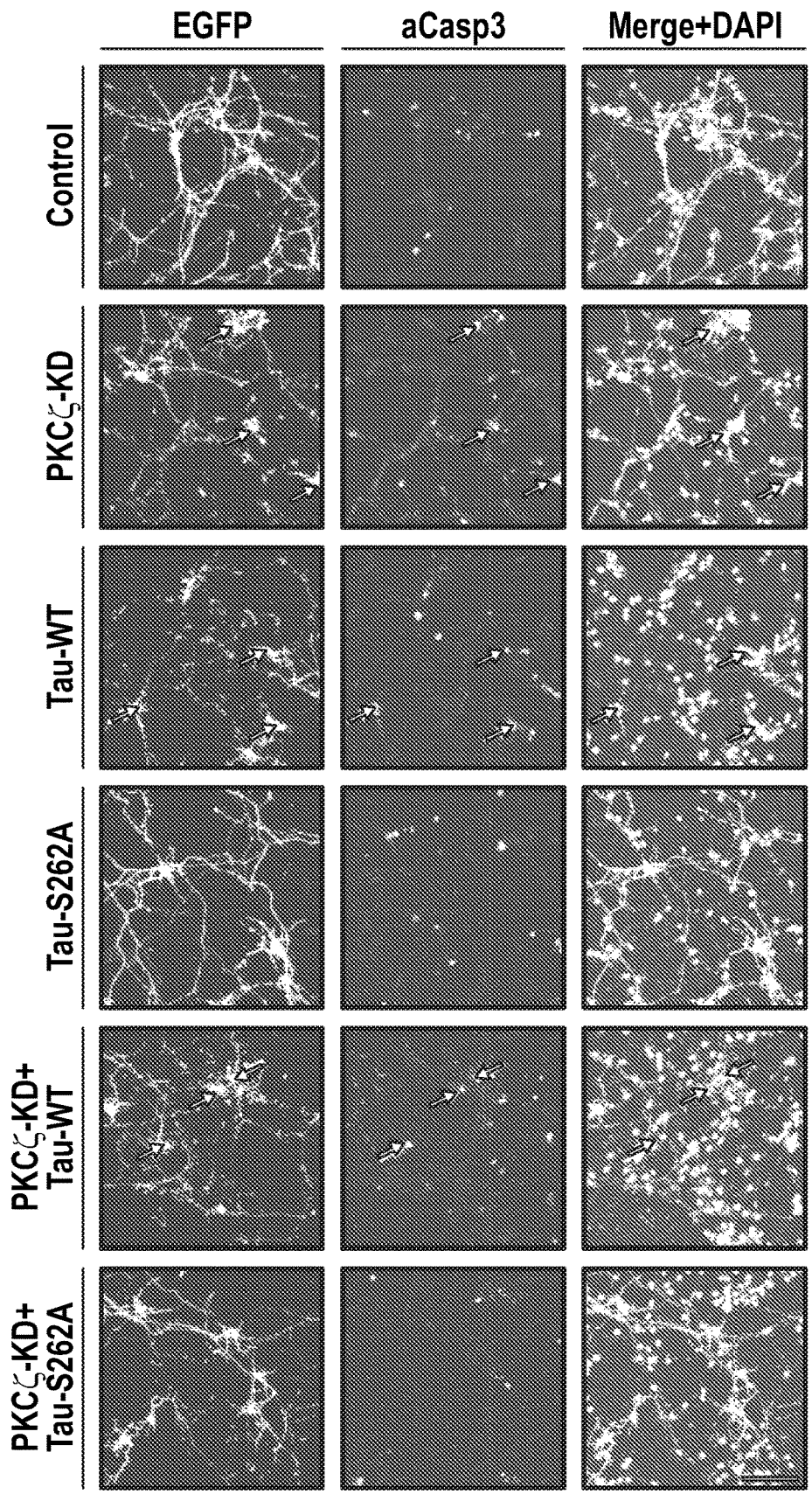
Figure 3H:
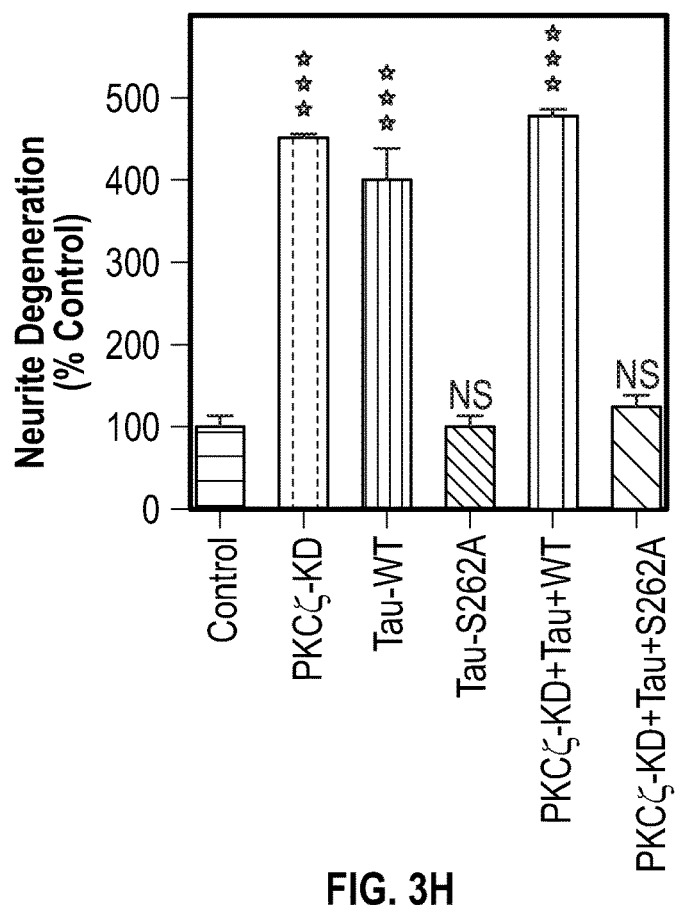
Figure 3I:
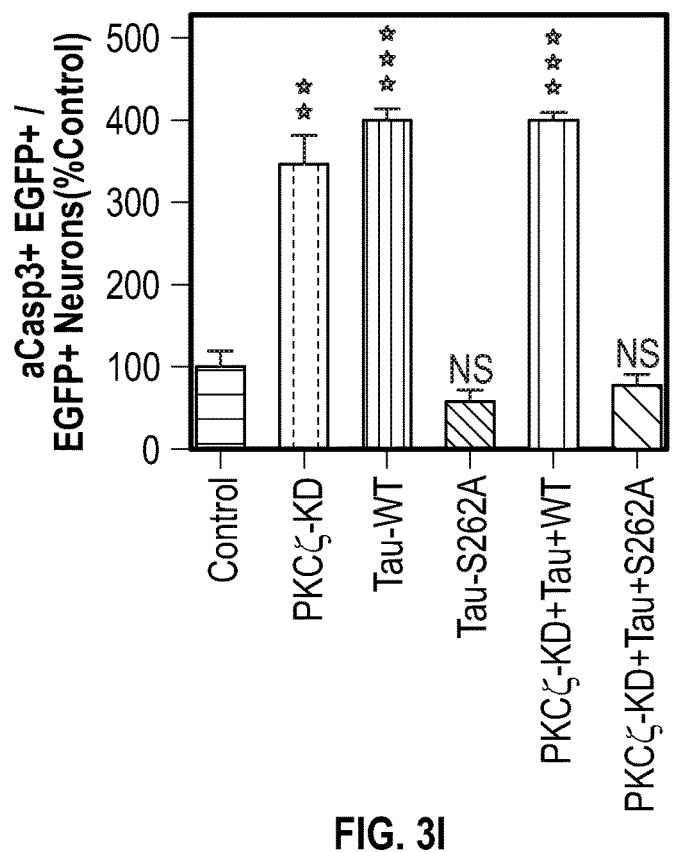

To further test the role of Tau phosphorylation in axonal degeneration induced by aPKC inhibition, cortical neurons were co-transfected with PKCζ-KD and Tau-WT or a non phosphorylatable mutant Tau at S262 (Tau-S262A) plasmidic construct. Overexpression of Tau-WT, but not Tau-S262A, induced axonal degeneration and neuronal apoptosis in a similar extent than PKCζ-KD (FIGS. 3G-3I). Co-transfection of PKCζ-KD with Tau-S262A but not with Tau-WT prevented axonal degeneration and neuronal cell death induced by PKCζ-KD overexpression (FIGS. 3G-3I), suggesting that axonal degeneration induced by PKCζ-KD is mediated by Tau phosphorylation at S262.

EXAMPLE 4 aPKC Inhibition Activates the JNK-cJun Signaling Pathway

Figure 4A:
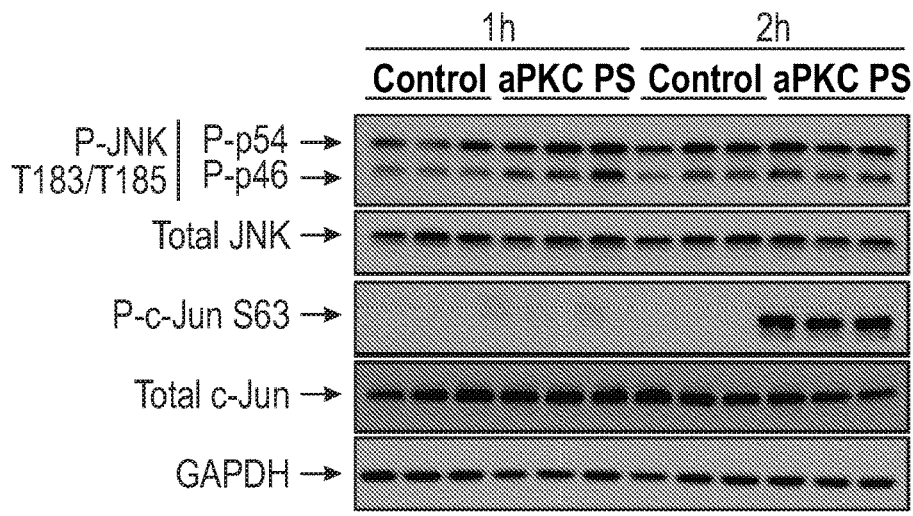
FIGS. 4A-4E are pictorial and graphical diagrams showing that aPKC inhibition activates the JNK-cJun signaling pathway.
Figure 4B:
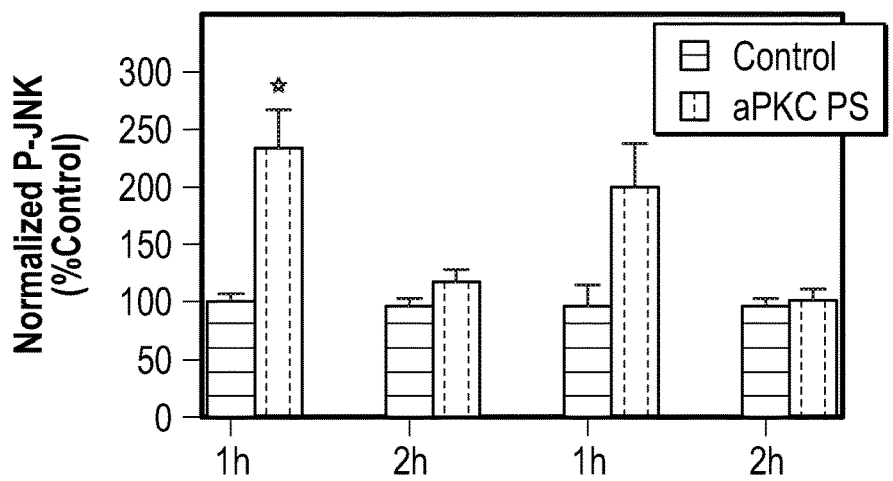
Figure 4C:
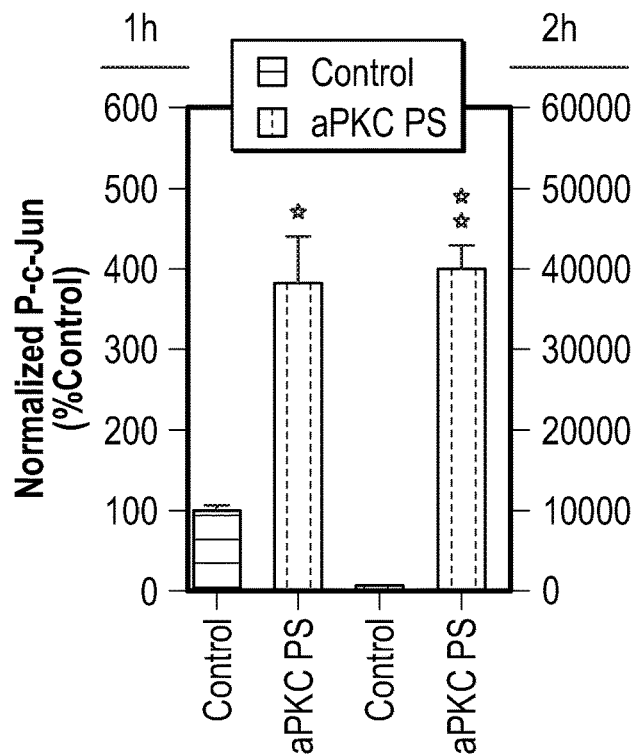
Figure 4D:
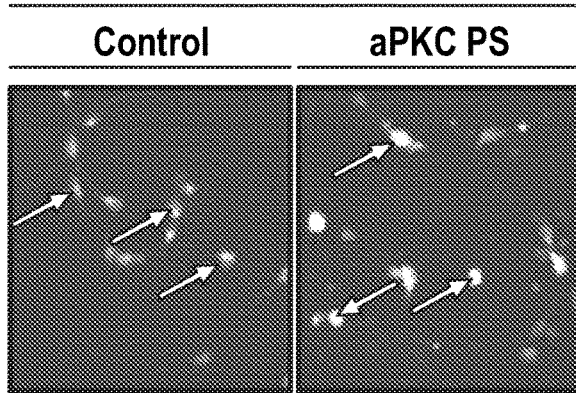
Figure 4E:
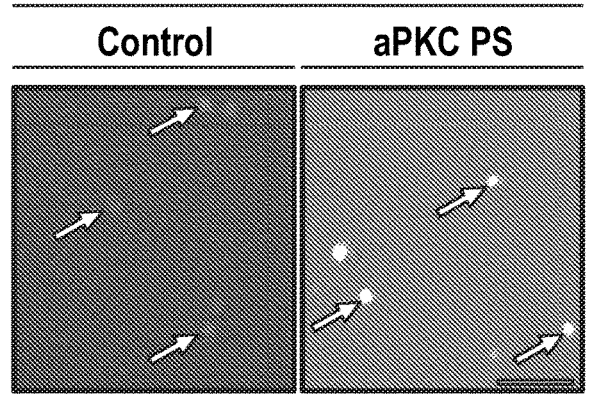

JNKs/SAPKs are a subfamily of MAPKs involved in a variety of physiological and pathological processes in the central and peripheral nervous system. In particular, JNKs mediate neuronal cell death in response to stress and injury and in some pathological conditions (42, 43). JNKs were also shown to induce, retrograde axonal degeneration and to limit motor recovery after spinal cord injury (44). It was therefore sought to determine whether JNKs might be involved in axonal degeneration induced by aPKC inhibition. Western-blotting experiments revealed that aPKC inhibition induced by aPKC PS leads to an increase of phosphorylation of JNKs at T183/T185. Increased phosphorylation occurred on both p54 and p46 protein isoforms at 1 h (FIGS. 4A and 4B). Phosphorylation of the transcription factor c-Jun was increased at S63, at 1 h and 2 h (FIGS. 4A and 4C), indicating that c-Jun, a direct substrate of JNK (45), is quickly activated when aPKC activity is inhibited. Increase of P-JNK-T183/T185 and P-cJun-S63 was confirmed in the nucleus of neurons by immunocytochemistry (FIGS. 4D and 4E). These results suggest that aPKC inhibition might promote axonal degeneration and neuronal cell death by activating the cell death JNK/c-Jun pathway.

EXAMPLE 5

Ryk Promotes Axonal Degeneration Induced by aPKC Inhibition

Figure 5A:
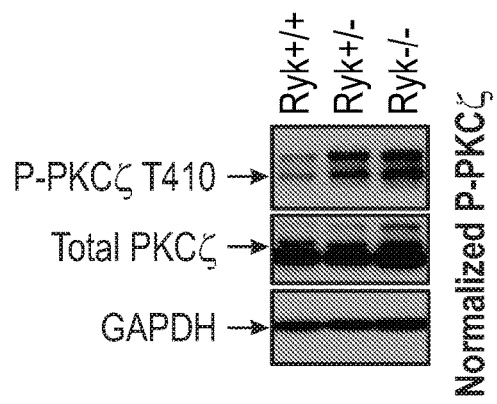
Figure 5B:
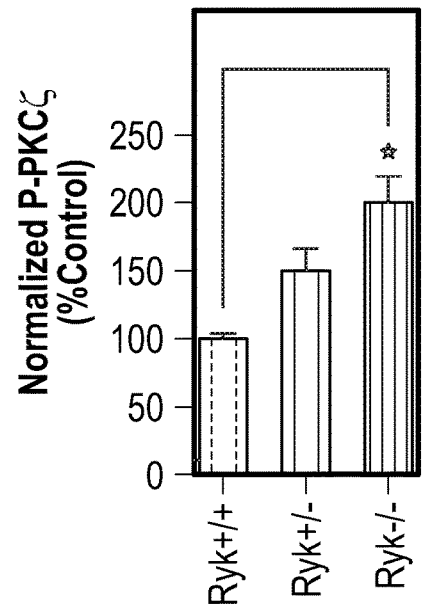

Previous studies showed that aPKC is a kinase required for Wnt-Frizzled3 mediated axon growth and attraction and also exerts a positive feedback function to amplify planar cell polarity signaling by increasing Frizzled3 endocytosis (46). Because Ryk is a repulsive Wnt receptor and inhibits planar cell polarity signaling, it was tested whether Ryk regulates aPKC. It was found that P-aPKC-T410 level measured by Western-Blotting was increased in Ryk KO cortical neurons cultured for 3 days (FIGS. 5A and 5B), suggesting that Ryk normally inhibit aPKC activity.

It was previously shown that expressions of certain Wnts and of the Ryk receptor are re-induced after spinal cord injury and that blocking Wnt/Ryk signaling reduces the retraction of corticospinal axons from the injury site (32). These recent studies indicate that Ryk expression is increased in motor neurons and axons in the spinal cord of a mouse model of ALS at early stage of the disease progression, suggesting that Ryk is involved in the early steps of neurodegeneration in ALS (47). It was therefore hypothesized that Ryk may be also involved in axon degeneration and it was tested whether blocking Wnt/Ryk signaling could protect cortical axons from degeneration induced by aPKC inhibition.

Figure 5C:
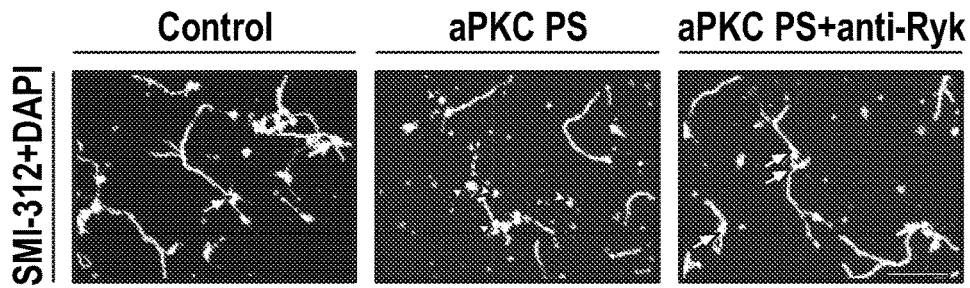

To block Ryk signaling, a mouse monoclonal antibody against the ectodomain of mouse Ryk was generated (by the laboratory of Alex Kolodkin at John Hopkins University, Baltimore, Md.). To test the specificity of this antibody, Western-Blotting analyses were performed on protein extracts from HEK cells transfected with a mouse Ryk expression vector. A signal was detected at approximately 70 KDa, the expected size for Ryk protein. A weaker band of similar size was detected endogenously in E14.5 embryonic wild type mouse tissue but not in Ryk KO tissue, suggesting that the antibody is specific to Ryk. Pre-incubation of cortical neuronal cell cultures with the mouse Ryk antibody but not with normal mouse IgG, 2 h prior to and during the 2 h of aPKC PS treatment, partially blocked axonal degeneration (FIGS. 5C and 5D). Axonal degeneration induced by aPKC inhibition was also analyzed in Ryk KO mouse neuronal cell cultures. Axonal degeneration triggered by aPKC PS was reduced in Ryk KO cortical neurons compared to WT neurons (FIGS. 5E and 5F).

EXAMPLE 6

Figure 6A:
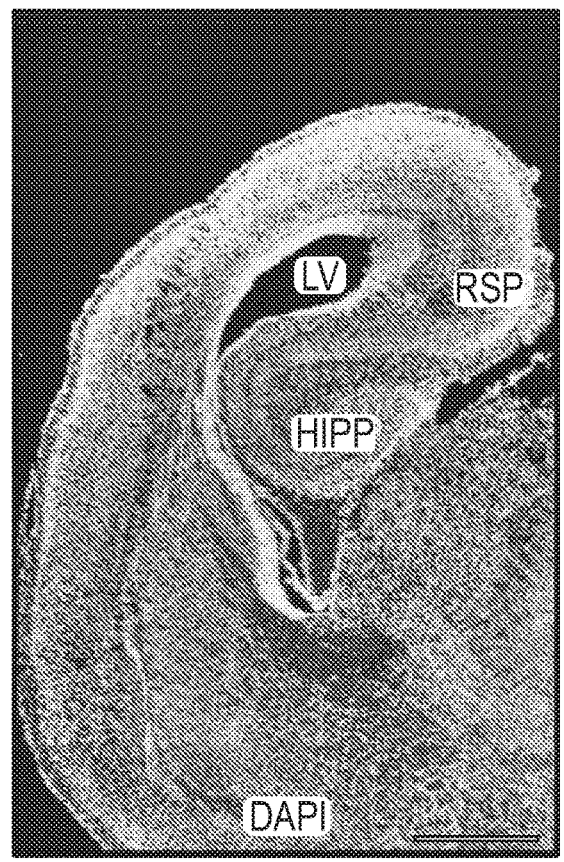
FIGS. 6A-6E are pictorial and graphical diagrams showing genetic interaction between Ryk and Frizzled3 in neuronal cell death.
Figure 6B:
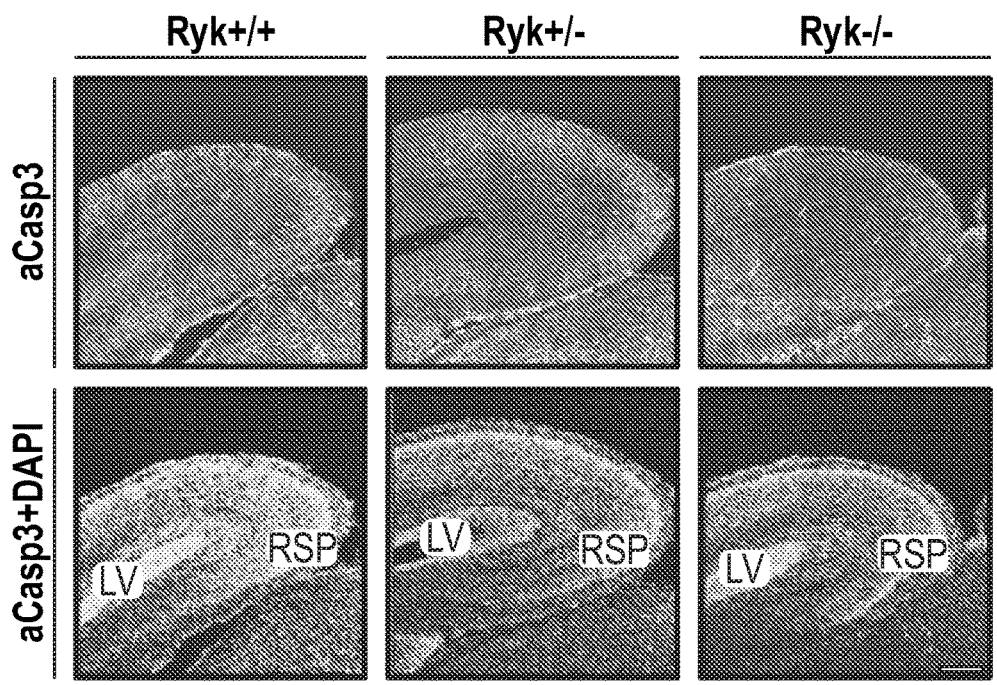
Figure 6E:
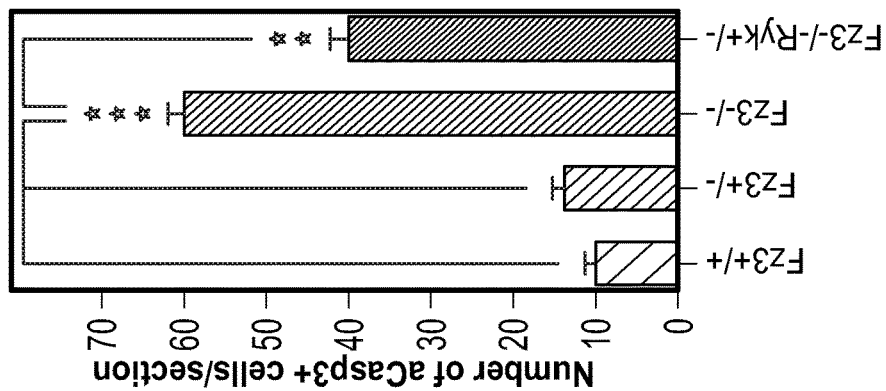
Figure 6D:
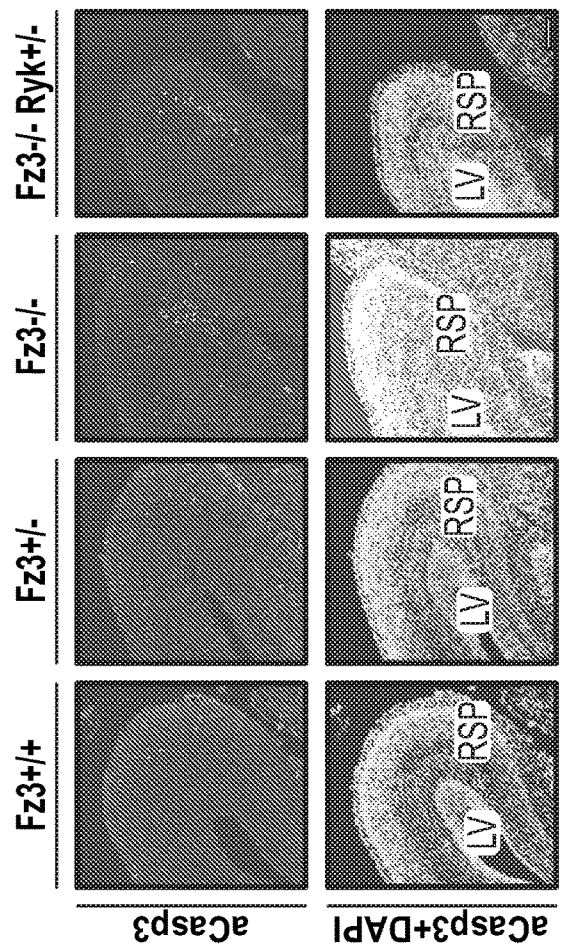
Figure 6C:
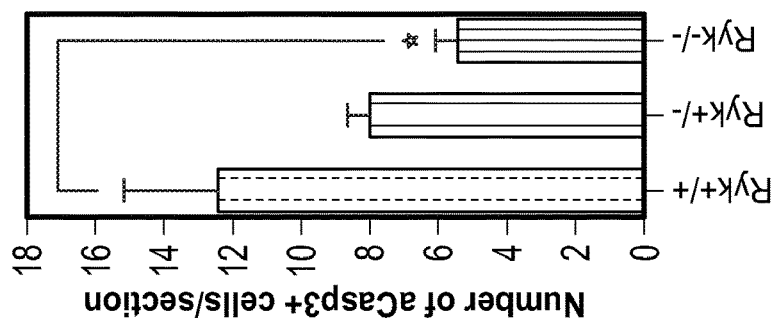

Neuronal Cell Death is Reduced in the Retrosplenial Cortex of Developing Ryk KO Mice The in vitro results suggest that Ryk may be involved in neuronal cell death. Previous studies showed that Ryk is expressed in the developing rodent forebrain including the isocortex, hippocampus and striatum (24, 48, 49). Apoptosis was examined in several regions of the forebrain in E18.5 Ryk deficient embryos, using aCasp3 immunostaining. Ryk KO mice exhibit craniofacial abnormalities including cleft palate and die at birth (50), so all analyses were performed prenatally during late gestation on E18.5 embryos. At E18.5, the overall architecture of $Ryk^{-/-}$ brain appears roughly normal and undistinguishable from $Ryk^{-/-}$ and $Ryk^{+/-}$ embryos (27). The number of aCasp3+ cells, although low in WT embryos was decreased by 45% in E18.5 RykKO mice in a restricted area of the cortex, the RSP, which corresponds to the posterior part of the cingulate cortex (FIGS. 6A-6C). However, apoptosis was not changed in the dorsolateral cortex, hippocampus and striatum in Ryk KO embyos, suggesting that Ryk might regulate cell death in specific regions of the developing cortex.

EXAMPLE 7

Ryk Heterozygosity Attenuates Neuronal Cell Death in the Retrosplenial Cortex of Frizzled3 KO Embryos Previous studies showed extensive cell death in the striatum of mouse embryos deficient for the Wnt receptor Frizzled3 and that Frizzled3 was strongly expressed in the developing striatum and isocortex (51). Cell death was examined in Frizzled3 KO mice, in the striatum and other regions of the forebrain including the RSP. These observations confirmed that apoptosis was strongly increased in the striatum. Interestingly, it was found that apoptosis was increased by 5 fold in the RSP of E18.5 $Frizzled3^{-/-}$ embryos, compared to $Frizzled3^{+/+}$ and $Frizzled3^{+/-}$ mice (FIGS. 6D and 6E). Double immunolabelings with neural precursor marker nestin and early neuronal marker βIII-tubulin showed that $aCasp3^+$ immunolabeling was localized in βIII-tubulin+ neurons. More precisely, aCasp3 co-localized with CTIP2 which is expressed in neurons of cortical layer V during embryonic development. However, apoptosis was not significantly different in E18.5 $Frizzled3^{-/-}$ compared to $Frizzled3^{+/+}$ embryos in the dorsolateral part of the cortex and hippocampus.

Since cell death was regulated in an opposite manner in the RSP of Frizzled3 KO and Ryk KO embryos, $Frizzled3^{+/-}$ mice were crossed with $Ryk^{+/-}$ mice. Double heterozygous mice resulting from these crossings were crossed with $Frizzled3^{+/-}$ mice for 6 generations to get the Frizzled3/Ryk mouse line into the Frizzled3 strain (Black6). Then, $Frizzled3^{+/-}$ $Ryk^{+/-}$ females were crossed with $Frizzled3^{+/-}$ $Ryk^{+/-}$ males. Over 52 embryos from 7 litters did not produce any embryos double knock-out for Frizzled3 and Ryk at E18.5, suggesting that $Frizzled3^{-/-}$ $Ryk^{-/-}$ embryos might not be viable at this developing stage. The analyses were therefore performed in $Frizzled3^{-/-}$ $Ryk^{+/-}$ embryos and it was found that knocking down Ryk expression by 50% attenuated apoptosis in the RSP of Frizzled3 KO embryos at E18.5, as shown by a 30% reduction of the number of activated Caspase $3^+$ cells in the RSP of $Frizzled3^{-/-}$ $Ryk^{+/-}$ embryos compared to $Frizzled3^{+/+}$ Ryk animals (FIGS. 6D and 6E).

EXAMPLE 8

Additional Methods

Animals were housed on a 12 hr light/dark cycle and behavioral analyses were done at consistent morning hours during the light cycle. Both mice and rats were group housed, except for mice with cranial windows which were singly housed after window implantation. Group sample sizes were chosen based upon previous studies and power analysis (25% effect size, a=0.05, 639~=0.2, power of 80%). One mouse was excluded from the study due to evidence of incomplete CS lesion with labeled corticospinal axons present at and below the level of the injury and one mouse was excluded as it did not attempt to perform the behavioral task after injury. All procedures and methods (surgical procedures, behavioral assays, tissue processing, immunostaining, image analysis, COS-7 transfection, and cortical mapping) were performed by investigators blinded to genotype or treatment group.

Generation of transgenic mice—The target vector containing loxP-flanked exons 3-6 as well as the PKG-neo selection cassette was transfected into ES cells. Cells were screened by Southern blot and PCR for integration of the targeting vector. Chimeric mice were then generated. Ryk cKO mice were crossed with Ai14 B6.Cg mice containing a loxP-flanked stop cassette preventing tdTomato expression (The Jackson Laboratory, Bar Harbor, Me., RRID:IMSR_JAX:007914) and backcrossed into C57BL/6J for 6 generations. For cortical mapping experiments, Ryk cKOAdTomato Ai14 mice were crossed with mice expressing channelrhodopsin (Chr2) behind the Thy1 promoter (B6.Cg-Tg(Thy1-COP4/EYFP)18Gfng/J) (The Jackson Laboratory).

Surgical Procedures—Cortical AAV injection: Adult female C57BL/6J mice (6.1±0.1 weeks old) were deeply anaesthetized with isoflurane until unresponsive to toe and tail pinch and the area over the skull was shaved and cleaned with povidone-iodine before incision. The skull was thinned bilaterally over the motor cortex and self-complementary AAV2/6 Cre-HA (Salk Institute for Biological Studies Gene Transfer, Targeting and Therapeutics Core, La Jolla, Calif.) ($1.49 \times 10^{11}$ genome copies/ml) was injected into 10 sites per hemisphere (250 nl/site) with a 36ga NanoFil needle (World Precision Instruments Inc., Sarasota, Fla.).

Cranial window: Adult female C57BL/6J mice (7.4±0.2 weeks old) were deeply anaesthetized with isoflurane. The skin over the skull was removed, the skull surrounding the motor cortex contralateral to the dominant forelimb was thinned, the skull over the motor cortex was removed, and self-complementary AAV2/6 Cre-HA was injected to 10 sites, as above. The exposed cortex was covered with a 5 mm #1 round glass coverslip (Warner Instruments, Hamden, Conn.) secured with VetBond (3M, St. Paul, Minn.). The exposed skull was covered with dental grip cement (Dentsply, York, Pa.).

CS and C3 dorsal column lesion (mice): Mice were deeply anaesthetized with isoflurane, spinal level CS (or C3) was exposed by laminectomy and the dorsal columns were lesioned at a depth of 1 mm with Vannas spring scissors (Fine Science Tools, Foster City, Calif.). The dorsal musculature was sutured with 4-0 silk sutures and the skin was closed with wound clips. Mice were randomly selected for C3 lesion or C3 sham (laminectomy only) groups.

Pyramidotomy: Mice were deeply anesthetized with ketamine (120 mg/kg) and xylazine (12 mg/kg), an incision was made and the ventral musculature was pushed aside to expose the pyramids. The dura was opened and the pyramid ipsilateral to the craniotomy was lesioned by 15° microscalpel (Electron Microscopy Sciences, Hatfield, Pa.) as previously described.

CS dorsal column lesion (rats): Adult female Fischer 344 rats (120-135 g) were deeply anaesthetized with 2 ml/kg of ketamine cocktail (25 mg per ml ketamine, 1.3 mg per ml xylazine and 0.25 mg per ml acepromazine). Spinal level CS was exposed by laminectomy, the dura was punctured over the dorsal horn, and the dorsal columns were lesioned with 2 passes of a Scouten wire-knife (David Kopf Instruments, Tujunga, Calif.). The dorsal musculature was sutured with 4-0 silk sutures and the skin was closed with wound clips. Polyethylene intrathecal catheters (Durect Corp., Cupertino, Calif.) were pre-filled with either mouse IgG or Ryk monoclonal IgG (clone 25.5.5 generated against the ectodomain of Ryk, amino acid range 90-183, by Johns Hopkins Monoclonal Antibody Core, Baltimore, Md.) (1 mg/ml) in artificial cerebrospinal fluid, threaded through magna cisterna to the cervical spinal cord, secured with 4-0 silk sutures, and attached to model 2004 osmotic minipumps (Durect Corp.) filled with 200 µl mouse IgG or Ryk IgG. Rats were randomly selected for mouse IgG or Ryk monoclonal IgG treatment. Osmotic minipumps were removed after 28 days. At 16 weeks after CS spinal cord injury, rats were injected bilaterally with 10% wt/vol 10,000 MW biotinylated dextran amine (BDA) in sterile phosphate buffered saline at 20 sites per hemisphere (250 nl/site); animals were sacrificed 2 weeks later.

Cortical mapping: Mice were lightly anaesthetized with ketamine (100 mg/kg) xylazine (10 mg/kg) mixture, still responsive to toe and tail pinch, and maintained during the course of stimulation with ketamine/xylazine mixture. Mice were fixed in a stereotaxic frame (David Kopf Instruments) and a fiber optic cable and cannulae (200 µm diameter) affixed to the stereotax arm were used to stimulate motor cortex locations relative to bregma that were unobstructed by skull or dental cement (maximum of 165 sites). Stimulation was 3 pulses of 470 nm light, 250 ms duration at 1 Hz from a single channel LED driver (Thorlabs, Newton, N.J.). The intensity of stimulation was increased from 50 mA up to 1000 mA until movement was detected in 3 consecutive pulses. Sites with no evoked movements at 1000 mA were scored as unresponsive. Only contralateral forelimb movements were scored; occasional, weaker, ipsilateral movements were observed as previously described in rats.

Ryk knockout in postnatal day 0 pups: Pups were injected with 0.50 AAV2/1-synapsin-Cre (Penn Vector Core, Philadelphia, Pa.) ($1.99 \times 10^{13}$ genome copies/ml) was injected into 2 sites in the motor cortex unilaterally with a 36ga NanoFil needle (World Precision Instruments Inc.). Mice were sacrificed 7 days later and the motor cortex was isolated and homogenized in lysis buffer (20 mM Tris HCl, pH 7.5, 150 mM NaCl, 1 mM EDTA, 1 mM EGTA, 10 mM NaF, 10 mM β-glycerophosphate, 1 mM $Na_3VO_4$, 0.5% wt/vol sodium dodecyl sulfate, 1% vol/vol TritonX-100, and complete protease inhibitor cocktail (Roche, Indianapolis, Ind.). Protein was analyzed by Western blot (40 µg/well). Antibodies used for Western mouse anti-Ryk (20 µg/ml) (Johns Hopkins Monoclonal Antibody Core), GAP DH (1:1000) (EMO Millipore, Billerica, Mass., catalog #MAB374, RRID:AB_2107445).

Sacrifice and Tissue Processing: Animals were deeply anaesthetized with ketamine cocktail, transcardially perfused with ice-cold PBS followed by 4% wt/vol paraformaldehyde in PBS, and brains and spinal columns were post-fixed overnight at 4° C. in 4% wt/vol paraformaldehyde. Tissue was cryoprotected in 30% wt/vol sucrose in PBS. Mouse spinal cords and brainstems, and rat brainstems were sectioned on a cryostat (Leica, Buffalo Grove, Ill.) at 20 µm (saggital spinal cords, transverse brainstems) and mounted directly on Superfrost Plus slides (Fisher Scientific, Pittsburgh, Pa.). Rat spinal cords were sectioned sagittally at 40 μm thick and collected as free-floating sections. Sections were washed three times with PBS, blocked for one hour in PBS with 0.25% triton-X100 (PBST) and 5% donkey serum, then incubated overnight at 4° C. with primary antibodies in PBST plus 5% donkey serum. The next day, sections were washed three times, incubated with Alexa Fluor conjugated secondary antibodies (Life Technologies, Grand Island, N.Y.; Jackson ImmunoResearch, West Grove, Pa.) for 2.5 hours at room temperature, counterstained with DAPI (1 μg/ml) (Sigma-Aldrich, St. Louis, Mo.) and washed three final times in PBS. Antibodies used for fluorescent immunohistochemistry were: rabbit anti-dsRed (1:1000) (Clontech Laboratories Inc., Mountain View, Calif., catalog #632496, RRID:AB_10013483), monoclonal G-A-5 anti-GFAP (1:200) (Sigma-Aldrich, catalog #G3893, RRID: AB_2314539), guinea pig anti-vGlut1 (1:1000) (EMO Millipore, catalog #AB5905, RRID:AB_2301751), and rabbit anti-GFAP (1:750) (Dako, Carpinteria, Calif., catalog #Z0334, RRID:AB_10013382).

COS-7 Cell Transfection: COS-7 cells were transfected with pcDNA4-Ryk using FuGene6 (Roche) to express full length Ryk. Cells were either fixed for 30 min with ice-cold 4% wt/vol paraformaldehyde in PBS for immunocytochemistry, or lysed with lysis buffer for Western blot.

Image acquisition and analysis: Images were acquired on an inverted Zeiss LSM510 confocal microscope with LSM acquisition software (Carl Zeiss Microscopy, LLC, Thornwood, N.Y.). Image density quantification was done on thresholded images using ImageJ (NIH, Bethesda, Md.). An investigator blinded to the experimental group performed all analyses. Axon index is the total thresholded pixels at every 0.411 μm in 8 total serial sagittal spinal cord cryosections spaced 140 μm apart for mice, or 0.741 μm in 6 total serial sagittal spinal cord cryosections spaced 280 μm apart for rats, divided by thresholded pixels in transverse sections of the pyramid at the level of the obex. Lesion volume was calculated using the Cavalieri estimator tool in StereoInvestigator (MBF Bioscience, Williston, Vt.) on every seventh 40 μm sagittal section. For tdTomato and vGlut1 colocalization, all axons within the gray matter were quantified over a region 210 μm wide at a distance of 600 μm rostral to the CS lesion in the 8 total serial sagittal cryosections used for tdTomato quantification. The location of 600 μm was chosen as it was observed that the highest density of axon collaterals in this region in both groups of animals (FIG. 8G) and it was located between the original CS and secondary C3 lesions.

Behavioral testing: All animals were trained on skilled forelimb reach over a period of two weeks prior to bilateral spinal cord injury. Animals were food restricted during training and then for 24 hours prior to weekly training after injury. Animals reached through a vertical slot in the front of an acrylic chamber and over a small gap to retrieve a reward pellet. Mice performed 25 reaches per session for 20 mg sucrose reward tablets (TestDiet, St. Louis, Mo.). Rats performed 50 reaches per session for 45 mg sugar pellets (Bio-Serv, Flemington, N.J.). Successful retrieval rate was calculated as the number of pellets that were retrieved and eaten divided by the number contacted by the forepaw. Forelimb reach was trained twice weekly by two independent investigators blind to genotype or experimental treatment; the two independent scores were averaged. Mice in the group without weekly training during recovery were only tested twice, at 8 weeks after injury. In addition to forelimb reach, rats were tested once weekly on a grid crossing task, where forelimb footfalls were calculated as a percentage of total forelimb steps in 3 passages over a 60 inch span of 1 inch equidistant wire grid.

Figure 15A:
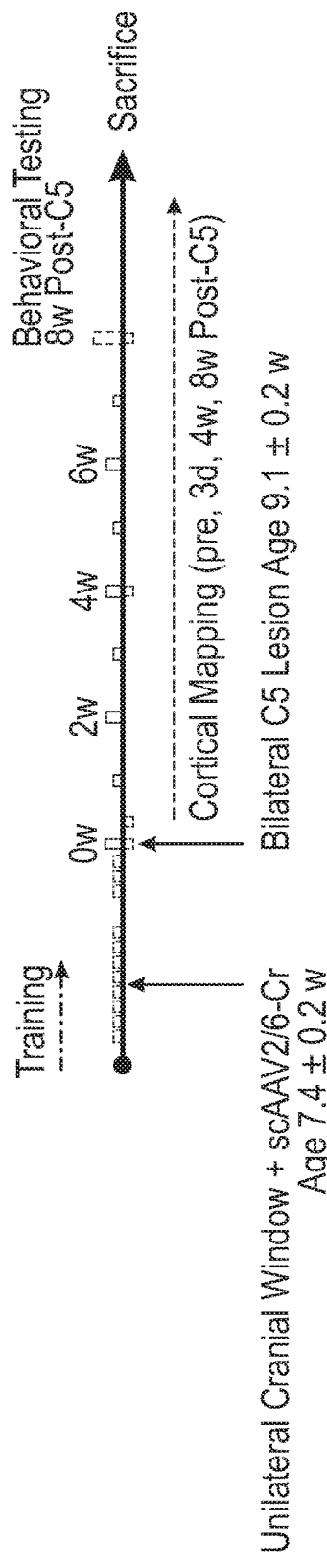
FIGS. 15A-15D are graphical diagrams showing that cortical map re-organization and functional recovery from spinal cord injury are dependent upon rehabilitative training.
Figure 15B:
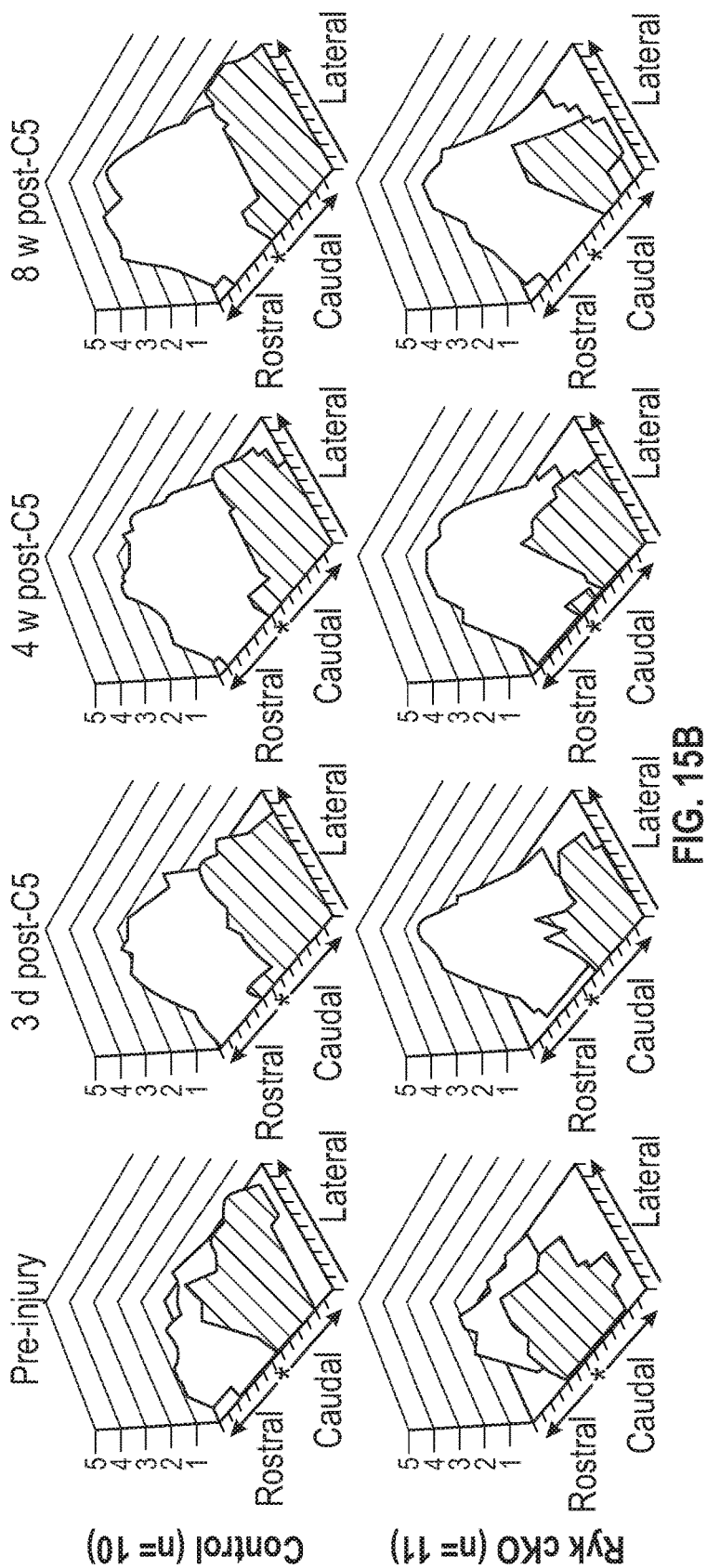
Figures 15C, 15D:
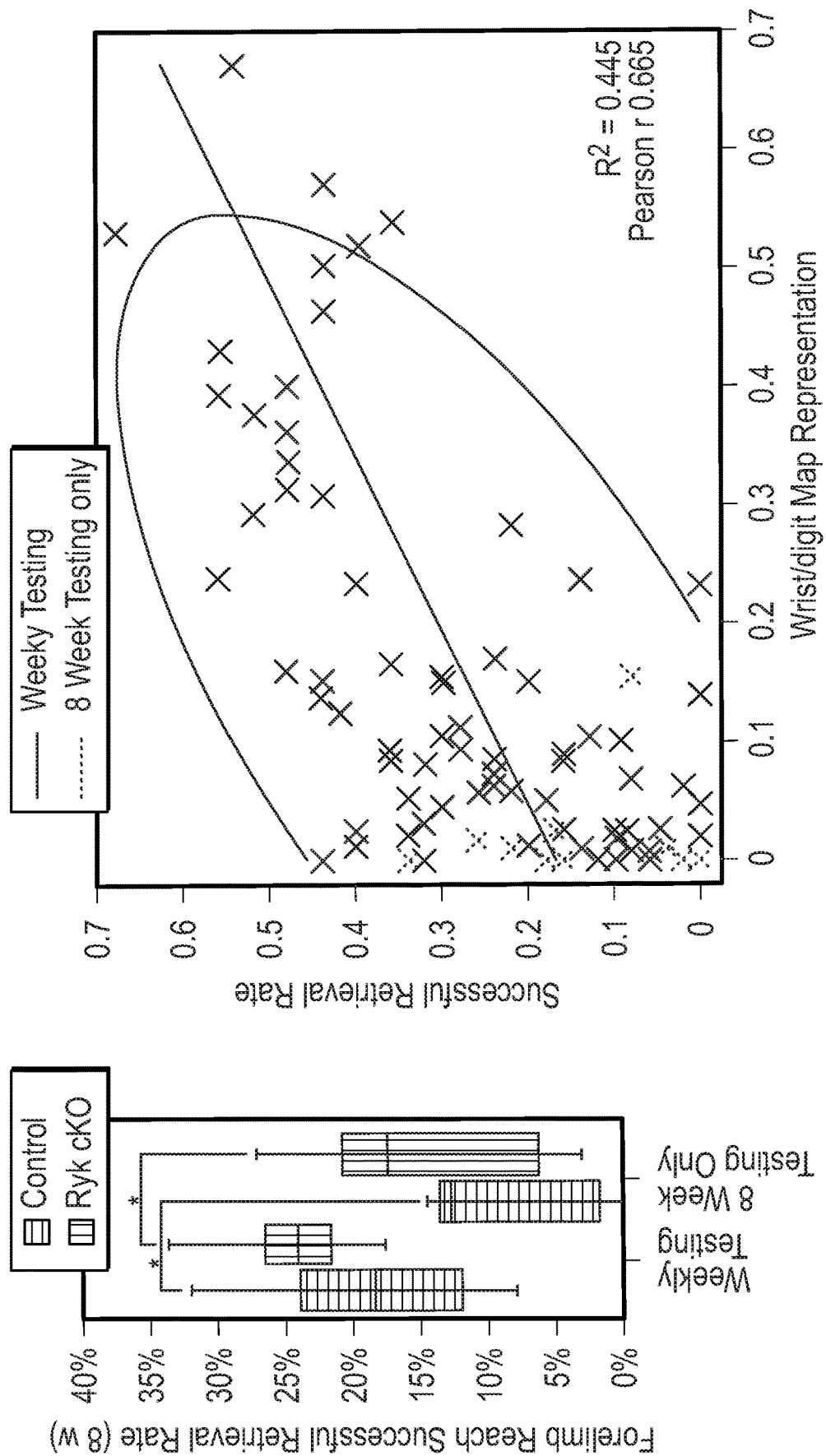
Figure 21:
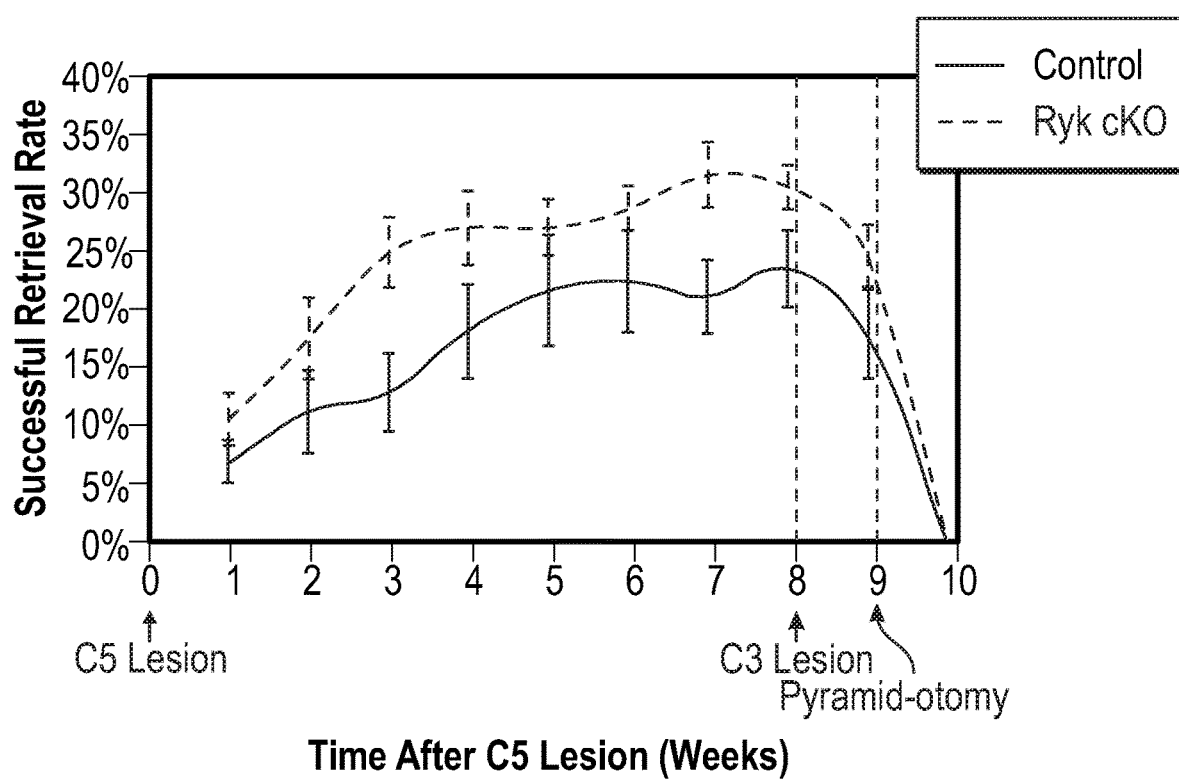
FIG. 21 is a graphical diagram showing recovery of skilled forelimb reach for mice used in cortical mapping experiments. Behavioral performance on skilled forelimb reach task shows enhanced recovery after Ryk conditional deletion in contralateral motor cortex (weeks 1-8 after C5 lesion, n=10 (control) 11 (Ryk cKO) mice, repeated measures ANOVA P=0.0304 F(1,19)=5.472). Secondary C3 eliminates enhanced recovery after Ryk conditional deletion (n=9 (control) 8 (Ryk cKO)), while unilateral pyramidotomy (n=8 (control) 7 (Ryk cKO)) completely ablates the ability of mice to perform the task. Data presented as mean±s.e.m.

Statistics: Statistical tests indicated in main text were performed using JMP 9 software (SAS Institute, Cary, N.C.). It was previously demonstrated that inhibition of repulsive Wnt signaling results in sprouting and plasticity of descending corticospinal and ascending dorsal column sensory axons after spinal cord injury. In addressing the hypothesis that Ryk cKO or Ryk monoclonal antibody enhanced axon sprouting, the increases were tested by one-tailed t-test (FIGS. 8E, 10B, 12I, and 18). In order to test longitudinal behavioral studies with multiple, equally spaced measurements, repeated measures ANOVA were utilized (FIGS. 8F, 12B, and 21). In testing multiple groups with continuous, parametric data, ANOVA with post-hoc Bonferroni correction was utilized on appropriate post-hoc comparisons (FIGS. 11C and 15C). Bivariate correlation was performed to determine the relationship between forelimb function and cortical maps (FIG. 15D). Continuous data was tested with parametric tests and data was assumed to be normally distributed, but this was not formally tested.

EXAMPLE 9

Ryk cKO Enhances Recovery of Fine Motor Control After SCI

Figure 8A:
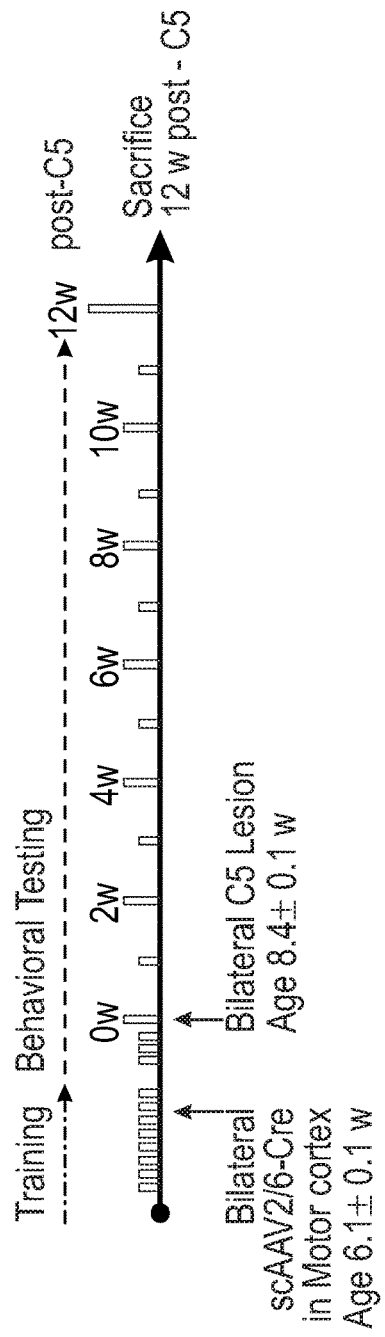
FIGS. 8A-8F are pictorial and graphical diagrams showing that Ryk conditional deletion enhances motor function recovery from spinal cord injury.
Figure 8C:
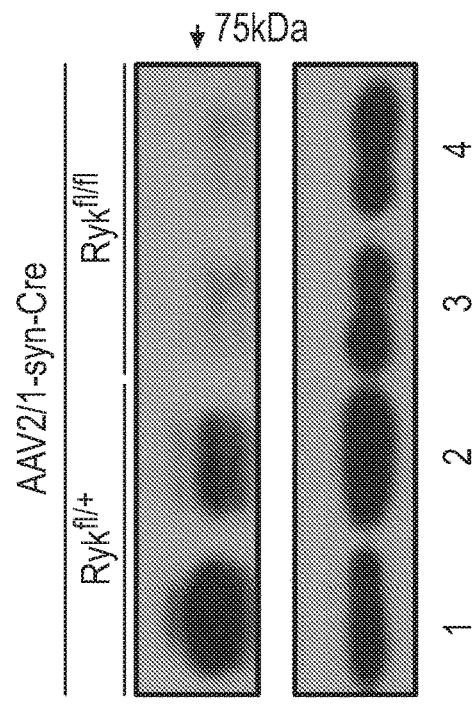
Figure 8B:
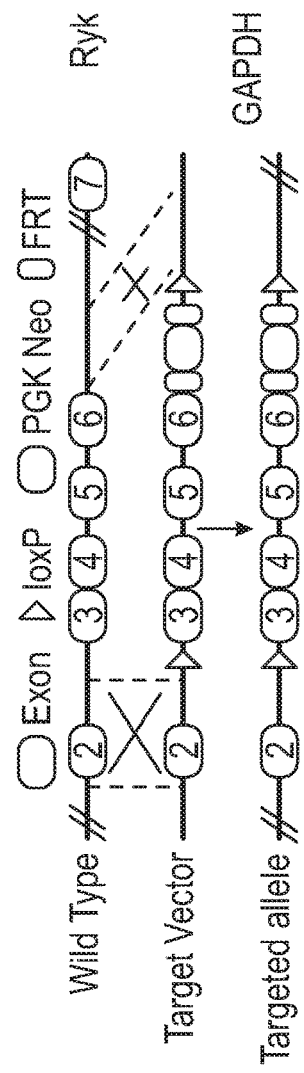
Figure 8D:
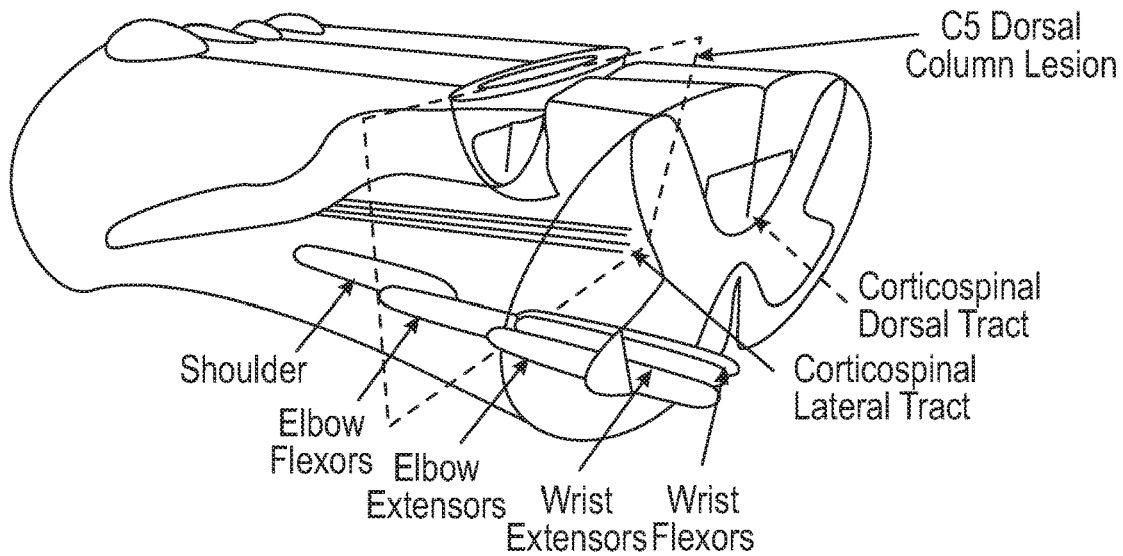
Figure 8E:
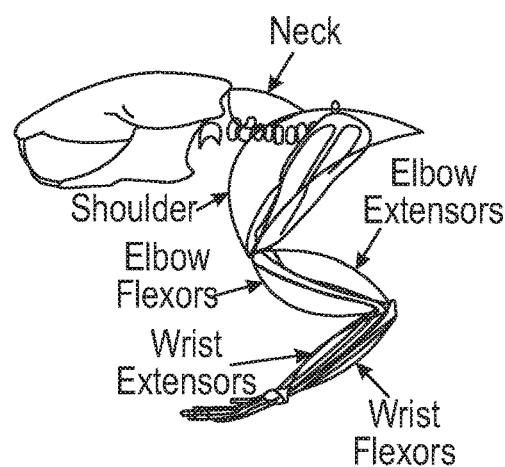
Figure 8F:
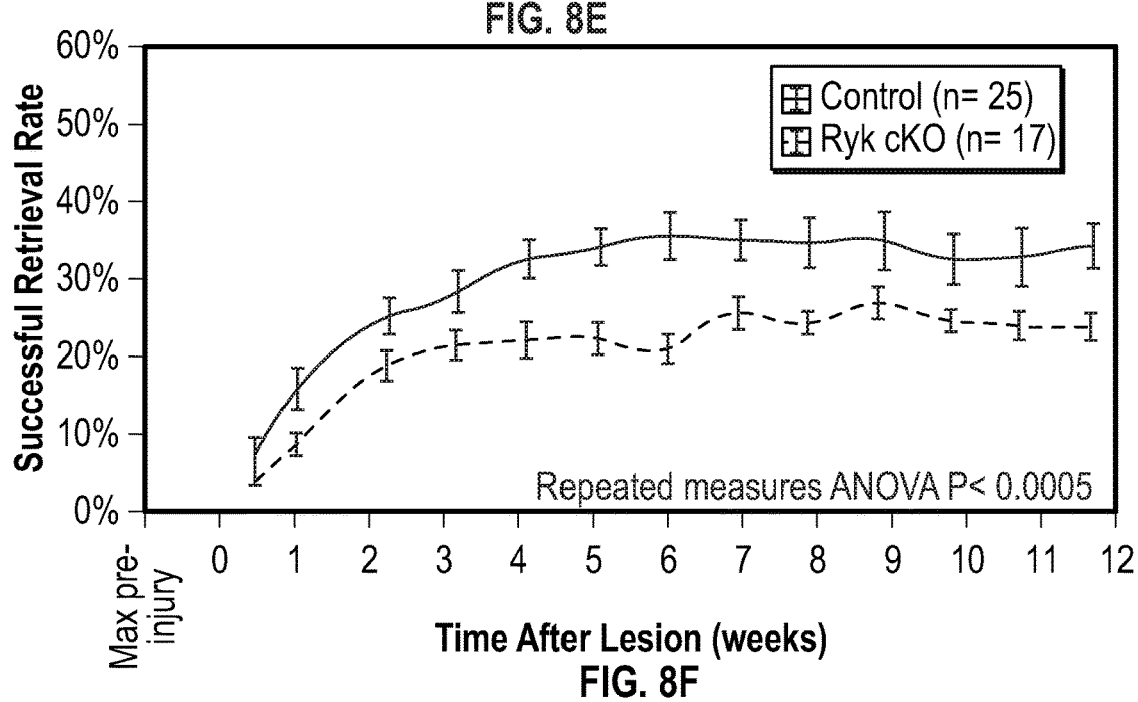

Mice underwent two weeks of training for the reaching and grasping task, followed by a CS dorsal column spinal cord lesion: a partial spinal cord injury model leaving the dorsal gray matter, lateral white matter and the entire ventral spinal cord intact (FIGS. 8A and 8D). Immediately after dorsal column lesion, forelimb reaching and grasping function is lost (FIG. 8F). With continued training, the success rate of sugar pellet retrieval recovers due to reconfiguration of neural circuits. It has been shown that the CST undergoes robust collateral sprouting after injury and some of the new sprouts are thought be responsible for new functional circuits. However, axon sprouting is inhibited by molecular cues that limit axon plasticity.

Members of the Wnt glycoprotein family are phylogenetically conserved axon guidance molecules that direct the growth along the rostro-caudal axis of both ascending sensory axons and descending CST axons during development. The repulsive Wnt receptor, Ryk, which mediates Wnt repulsion of the developing CST neurons is either not expressed in normal adult motor cortex and the CST neurons or expressed at extremely low levels to be detected by in situ hybridization or immunobistochemistry. Spinal cord injury re-induces expression of Ryk mRNA and protein in the injured CST. By injecting function-blocking antibodies to Ryk and diffusible Wnt inhibitors, it was found that inhibiting Wnt-Ryk signaling enhanced the plasticity of both sensory and motor axons following injury. However, Ryk antibodies or Wnt inhibitors may exert the effects by impacting on the environment, such as the glial cells around the lesion, rather than CST axons per se.

Figure 16:
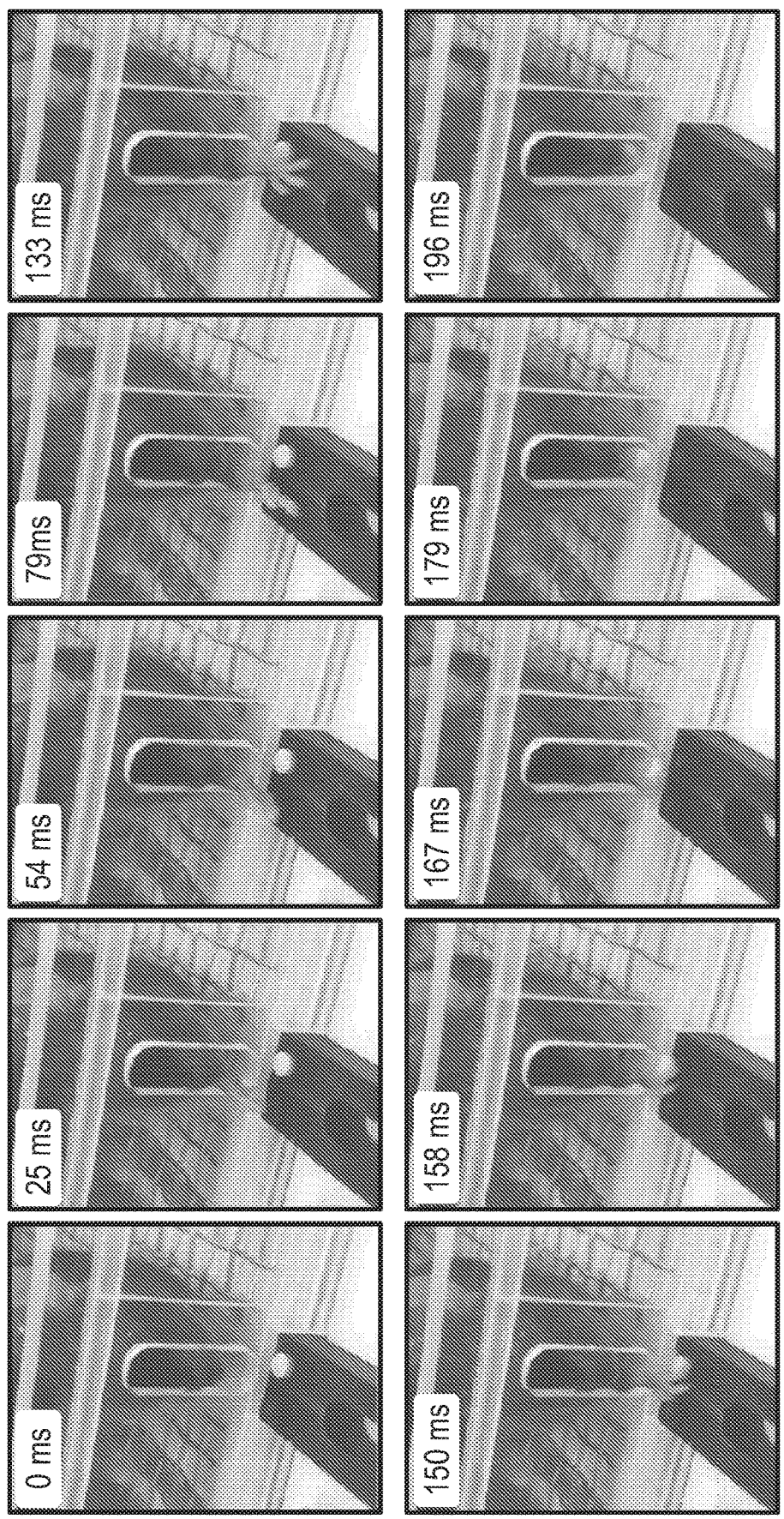
FIG. 16 is a pictorial diagram showing a series of sample frames from a forelimb read video. This example at 13 weeks after C5 dorsal column lesion (1 week after C3 sham operation) demonstrates the recovery of skilled forelimb grasp. Successful reach requires the use of a grasping motion as a sweeping motion would result in the pellet being dropped in either the gap between the food pellet platform (black) and the main enclosure, or through the wire-frame floor of the enclosure.

To specifically test the role of Ryk in neurons, a Ryk conditional allele (cKO) was created and these mice were crossed with Ai14 86.Cg mice containing a loxP-flanked stop cassette preventing tdTomato expression, in order to specifically label recombined corticospinal axons after viral transduction (FIGS. 8B and 8C). Ryk cKOAdTomato Ai14 mice were injected with an adeno-associated virus (AAV) that expresses Cre recombinase under the control of the cytomegalovirus (CMV) into the primary motor cortex and the enhancement of corticospinal circuit remodeling was assessed (FIG. 8A). AAV-Cre was injected to adult motor cortex an average of 2.3 weeks prior to CS dorsal column lesion in order to ensure sufficient time for Cre expression, so that injury would not lead to Ryk expression. It was found that Ryk deletion in the CST significantly enhanced recovery of skilled forelimb function as assessed by forelimb reach over a period of 12 weeks (Repeated measures ANOVA P<0.005, FIGS. 8F and 16). The effects of Ryk deletion were observed early on, with a trend towards better performance at early testing sessions. This was consistently observed and may be due to reduced retraction of axons and collaterals as previously demonstrated at 5 weeks post-injury in animals infused with Ryk antibodies. Following Ryk conditional deletion, mice recovered to 81±7% of peak pre-injury success rates, compared to only 60±5% in control mice.

EXAMPLE 10

Ryk cKO Enhances CST Collateral Sprouting after SCI

Figure 9A:
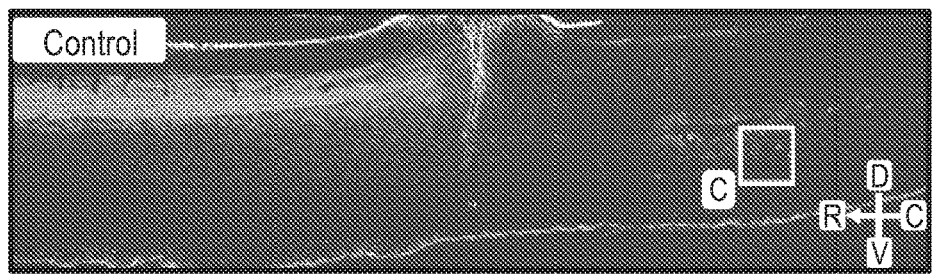
FIGS. 9A-9H are pictorial and graphical diagrams showing Ryk conditional deletion enhances corticospinal axon sprouting after spinal cord injury.
Figure 9B:
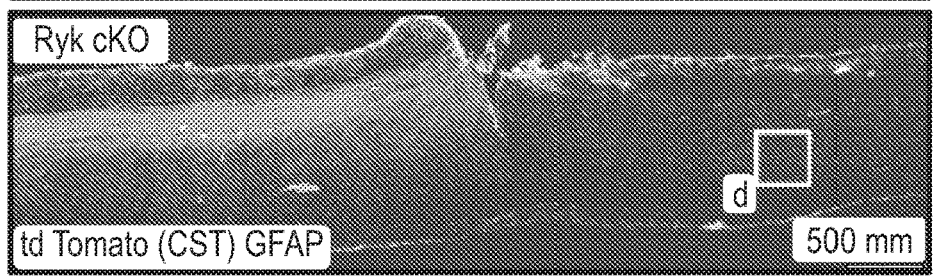
Figure 9C:
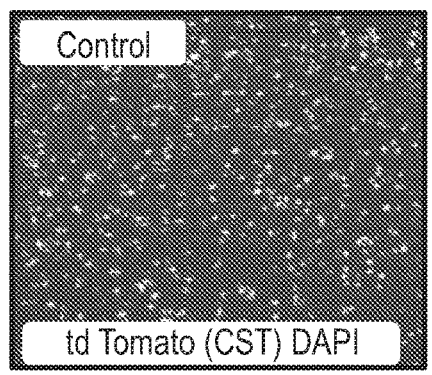
Figure 9D:
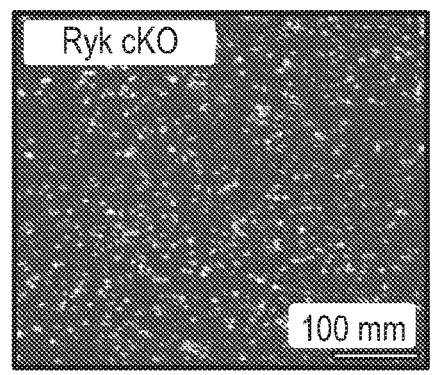
Figure 9E:
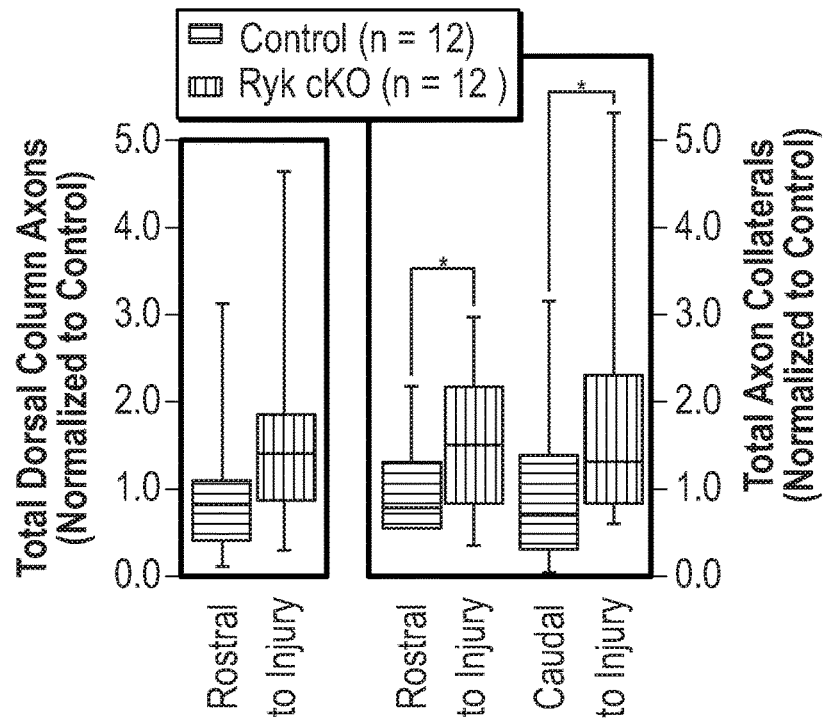
Figure 9F:
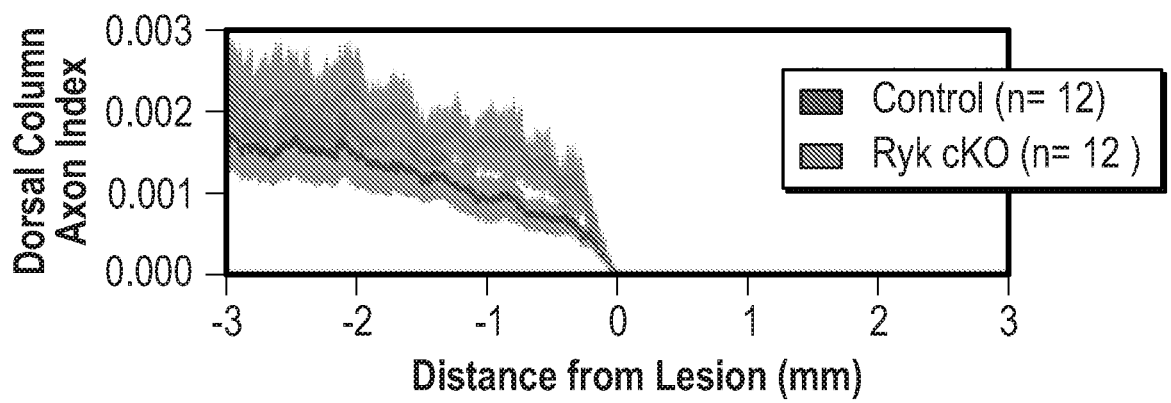
Figure 9G:
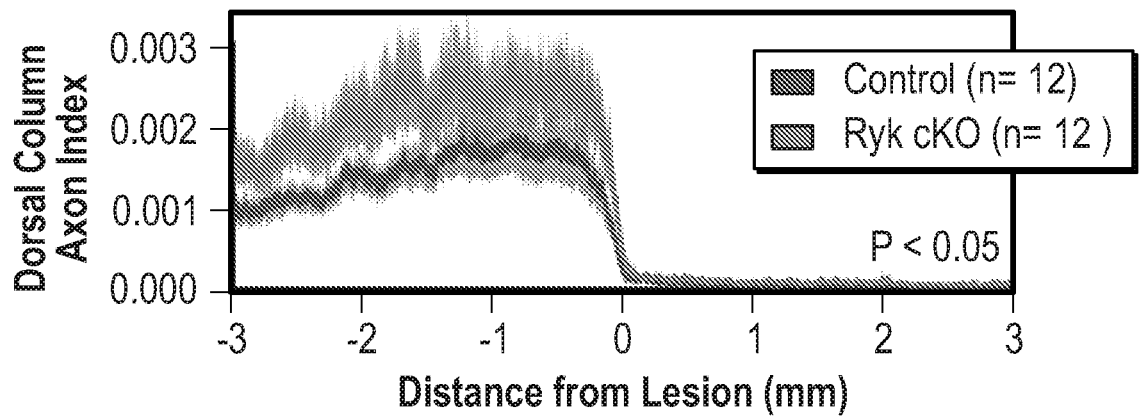
Figure 9H:
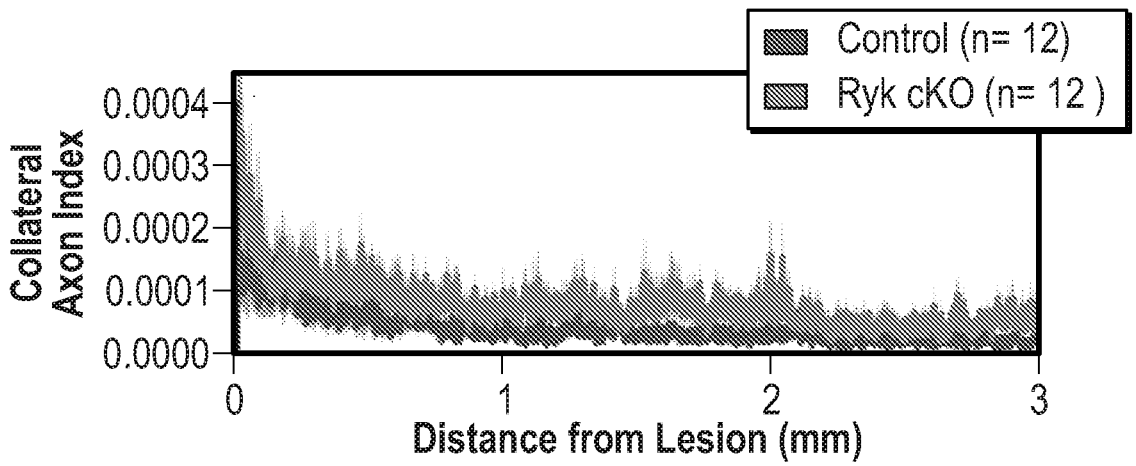
Figure 10A:
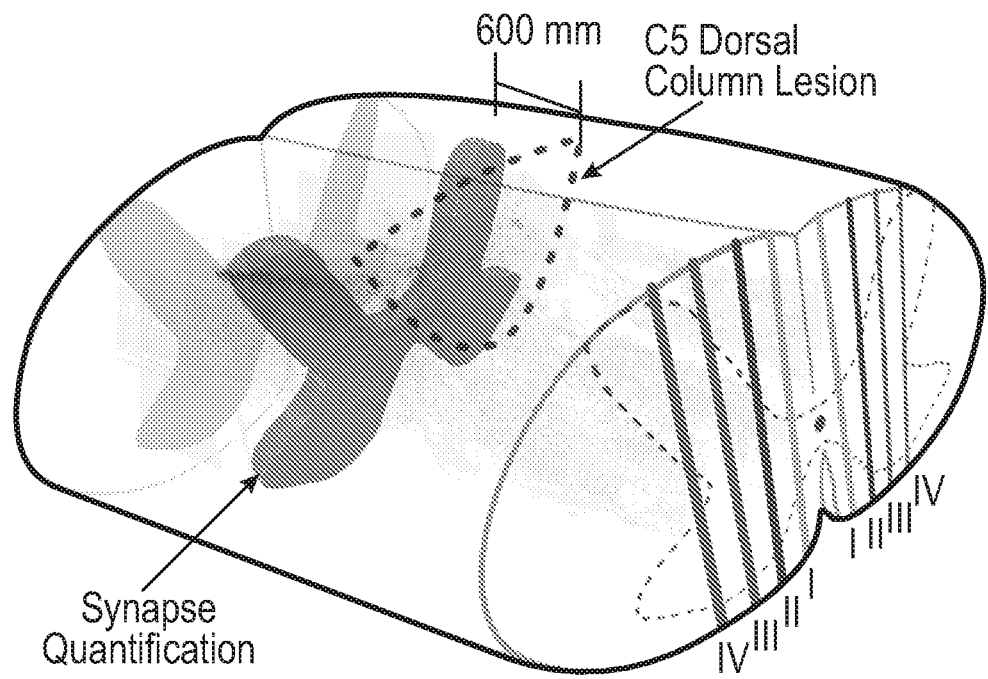
FIGS. 10A-10D are pictorial and graphical diagrams showing changes of corticospinal connectivity after CS dorsal column lesion.
Figure 10B:
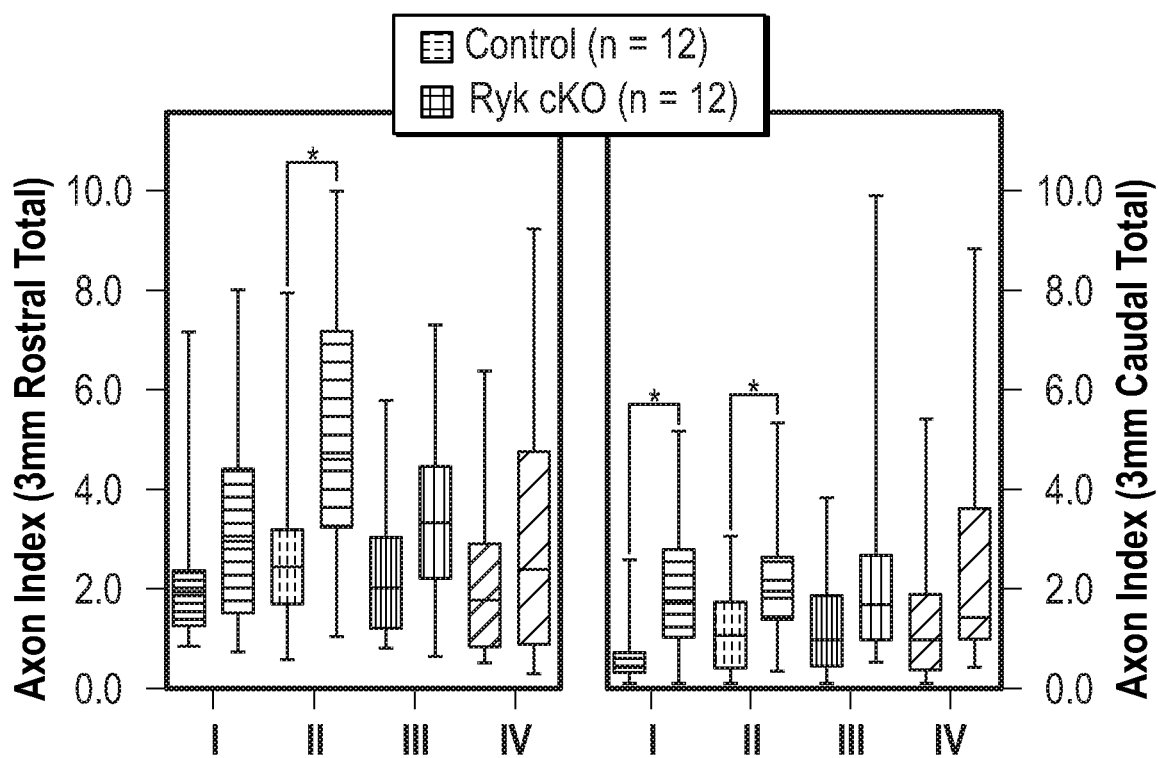
Figure 10C:
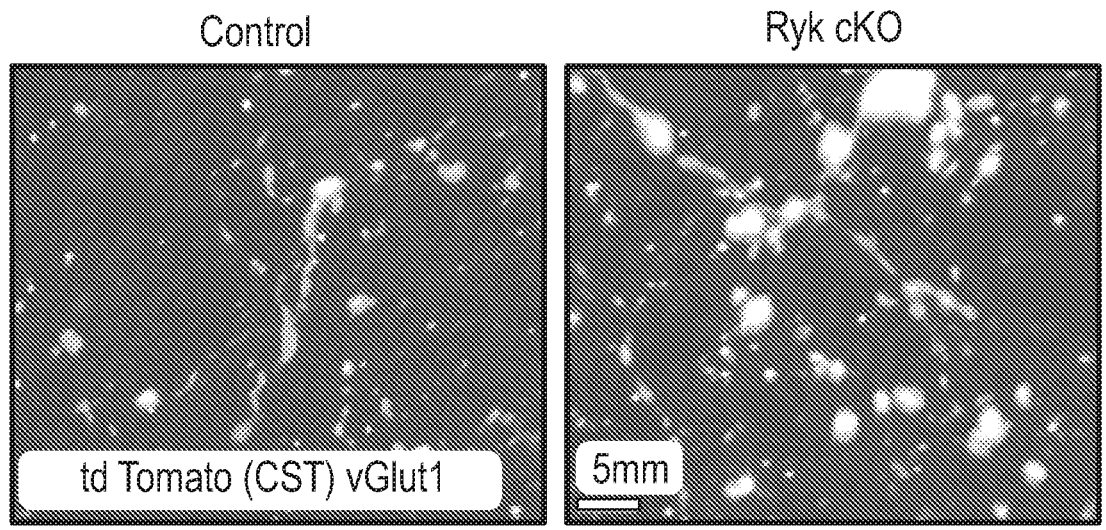
Figure 10D:
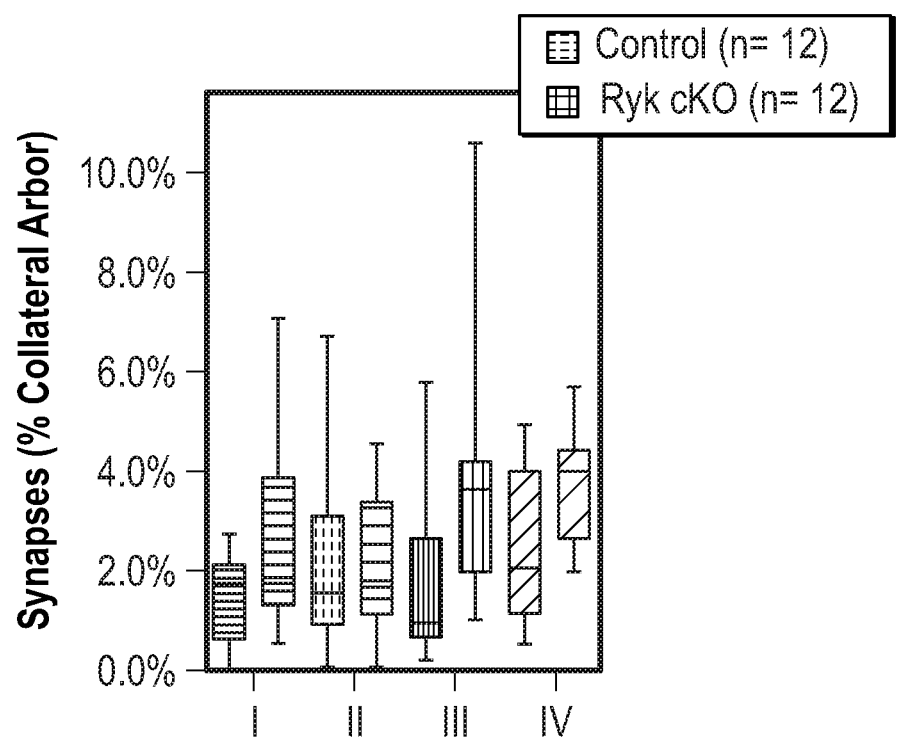

To begin to address the mechanisms underlying improved functional recovery in Ryk cKO mice, CST collaterals and synapse density were analyzed along collateral sprouts in the cervical spinal cord. It was found that conditional Ryk deletion did not significantly reduce axonal die-back of the injured CST (one-tailed t-test P=0.12), but did lead to significantly increased numbers of CST collaterals within the spinal gray matter, both rostral and caudal to the site of CS injury, at 12 weeks post-injury (one-tailed t-test P<0.05, FIG. 9E). In addition to a greater number of axon collaterals, mice with Ryk conditionally deleted from cortical pyramidal neurons exhibited pre-synaptic vesicular glutamate transporter 1 (vGlut1)-labeled puncta on identified corticospinal axon collaterals at 600 μm rostral to the injury site, suggesting enhanced functional connectivity following Ryk conditional deletion (FIGS. 10C and 10D).

The majority of CST axons reside within the dorsal columns and are lesioned by the CS dorsal column injury. A sparse, minor, component of CST axons descend down the spinal cord within the lateral columns (lateral CST), which remained intact in the CS lesion paradigm and may contribute to functional recovery (FIG. 8D). To test this, the distribution of axon collaterals were first characterized in the spinal cord both rostral and caudal to the CS lesion. It was observed that an increase in axon collateral density in Ryk conditional deleted mice throughout the gray matter, with the highest density more medial, in close proximity to the principal dorsal column corticospinal tract (FIGS. 10A and 10B), suggesting that increased branches may come from the dorsal column CST following Ryk deletion. No axons were present within the dorsal column CST caudal to CS lesion in any of the mice studied.

Figure 11A:
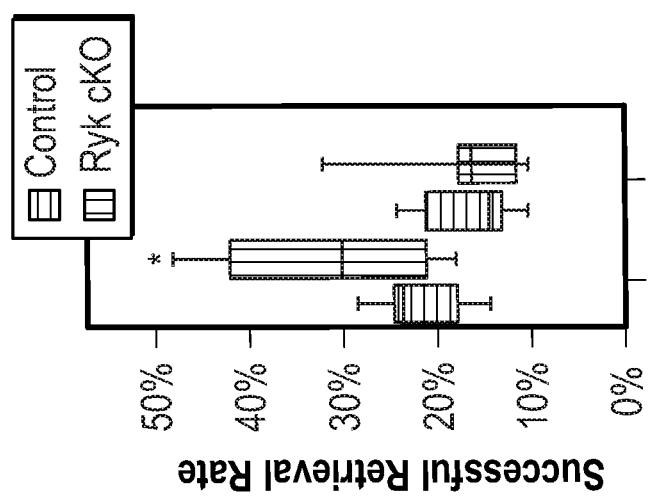
FIGS. 11A-11F are pictorial and graphical diagrams showing that secondary injury at cervical level 3 eliminates enhanced recovery.
Figure 11C:
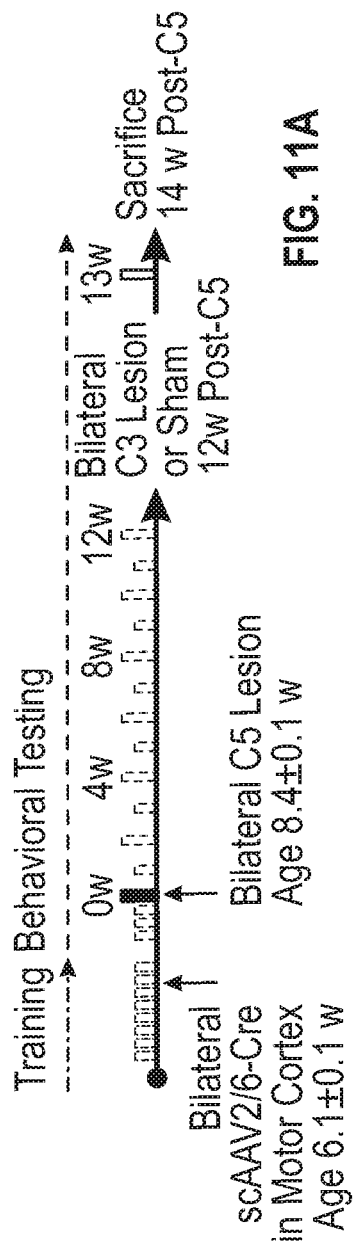
Figure 11B:
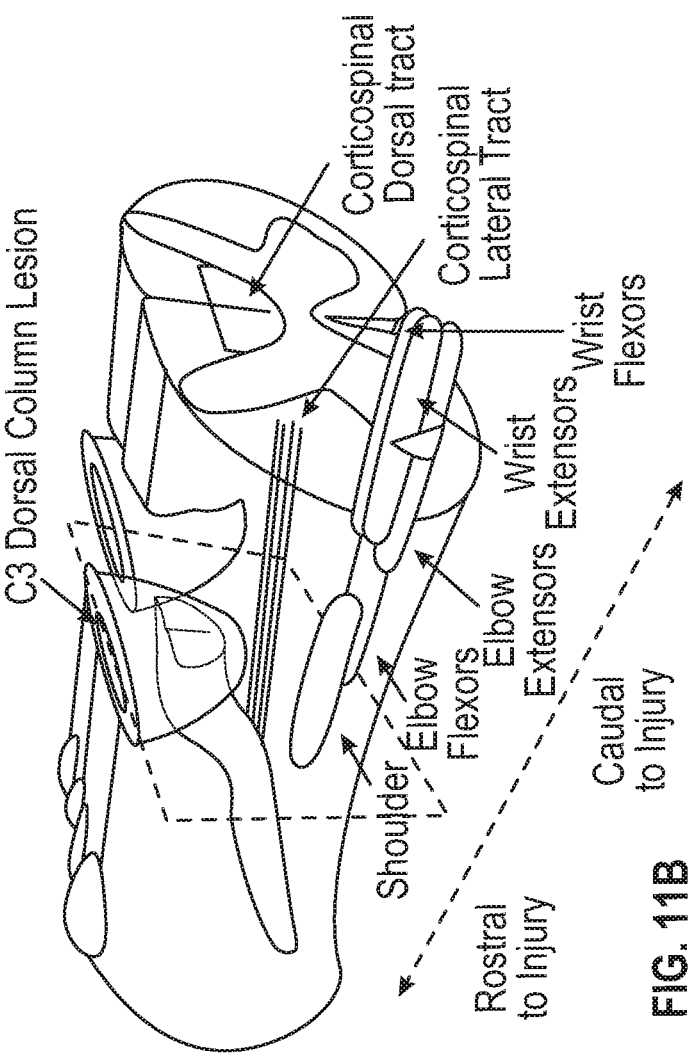
Figure 11D:
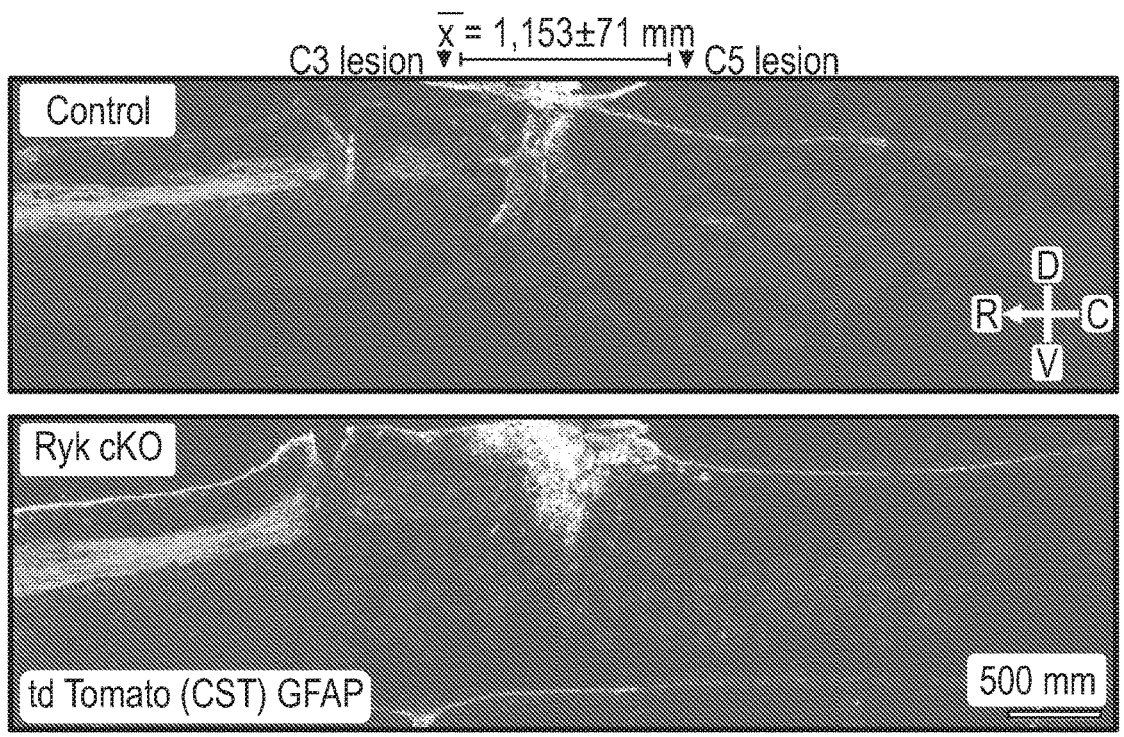
Figure 11E:
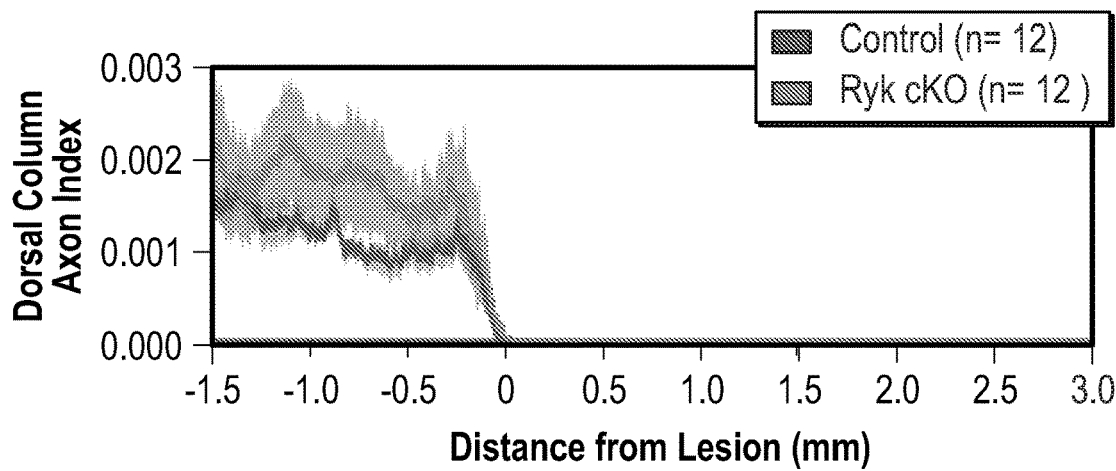
Figure 11F:
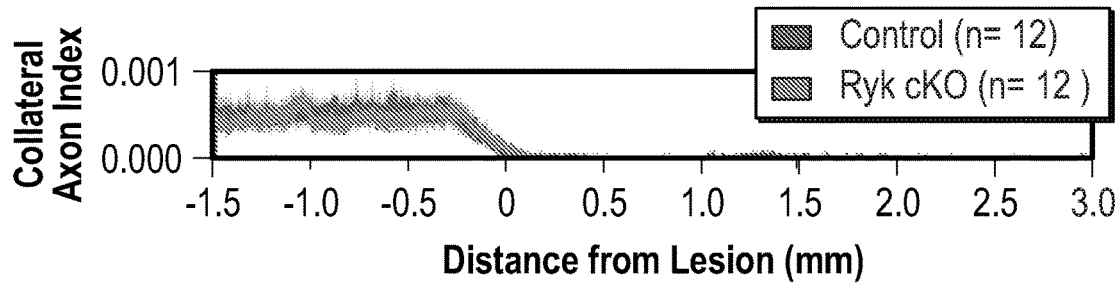

To further assess the contribution of the dorsal column CST to behavioral recovery, a second dorsal column lesion was performed in these animals 12 weeks after CS injury at the C3 level, 1.15±0.07 mm rostral to the original CS injury (FIGS. 11A and 11B). The lateral CST is again spared in this lesion. After a one-week delay to allow the mice to recover from the immediate hyporeflexic stage of spinal shock, behavioral testing began. The secondary injury at C3 ablated the enhanced functional recovery that was observed in the Ryk conditional deletion mice, leaving only the modest levels of partial recovery achieved by control mice (FIG. 11C). This suggests that the axon sprouts from the dorsal column CST are indeed responsible for the enhanced functional recovery in the Ryk conditional knockout. This also suggests that the spared lateral CST axons may provide only a minor contribution to a basal level functional recovery independent of the dorsal column corticospinal tract. Quantification of axon distribution at 2 weeks after C3 lesion confirmed that the secondary C3 injury eliminated a majority of axon collaterals between the two injury sites, thereby disrupting the remodeled corticospinal circuit (FIGS. 11D-11F).

EXAMPLE 11

Monoclonal Ryk Antibody Promotes Functional Recovery

Figure 12A:
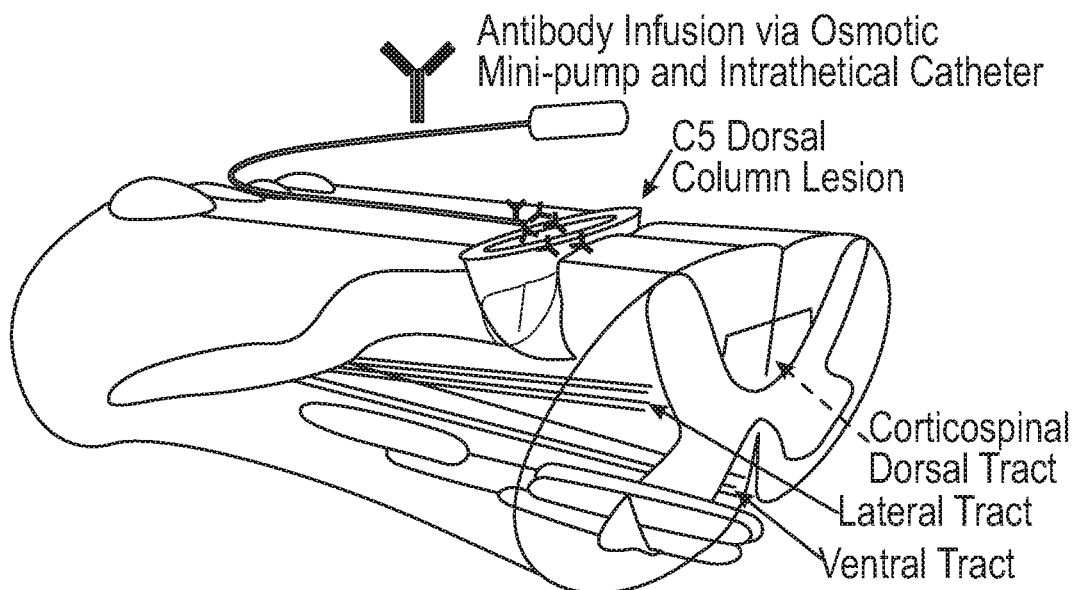
FIGS. 12A-12I are pictorial and graphical diagrams showing that monoclonal Ryk antibody infusion promotes functional recovery from spinal cord injury.
Figure 12B:
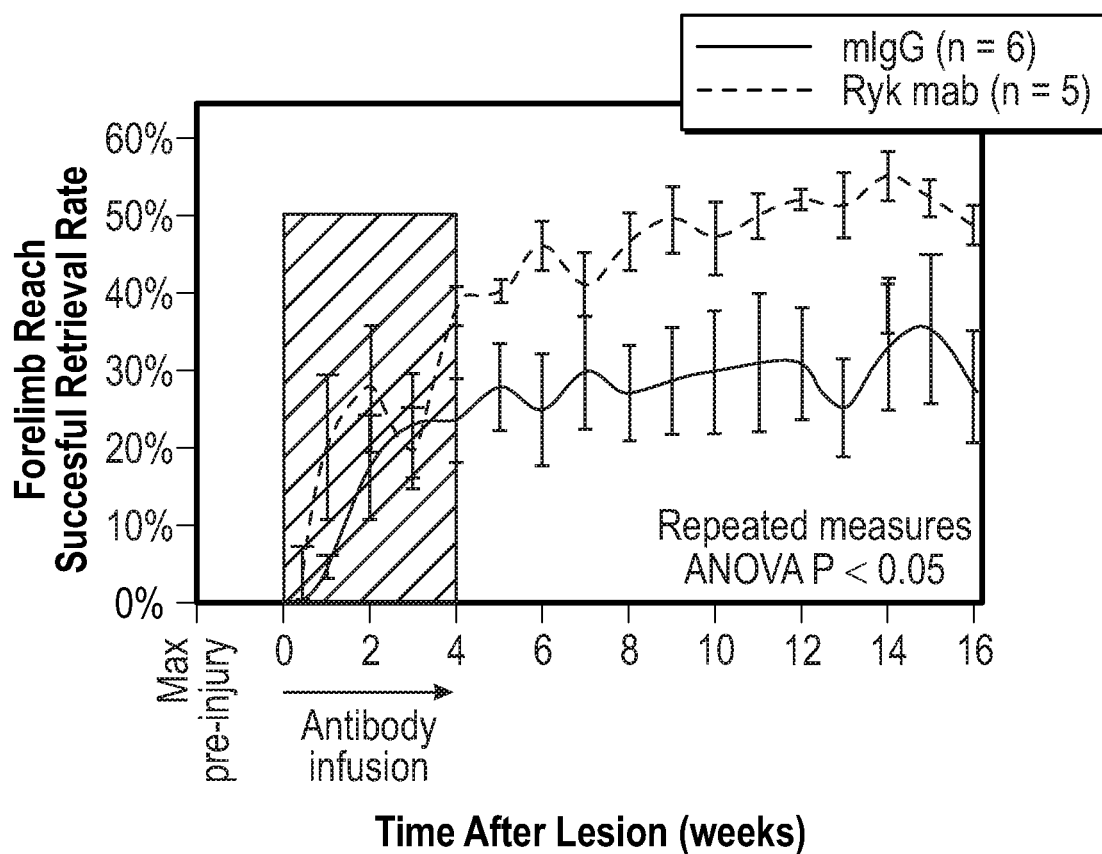
Figure 12C:
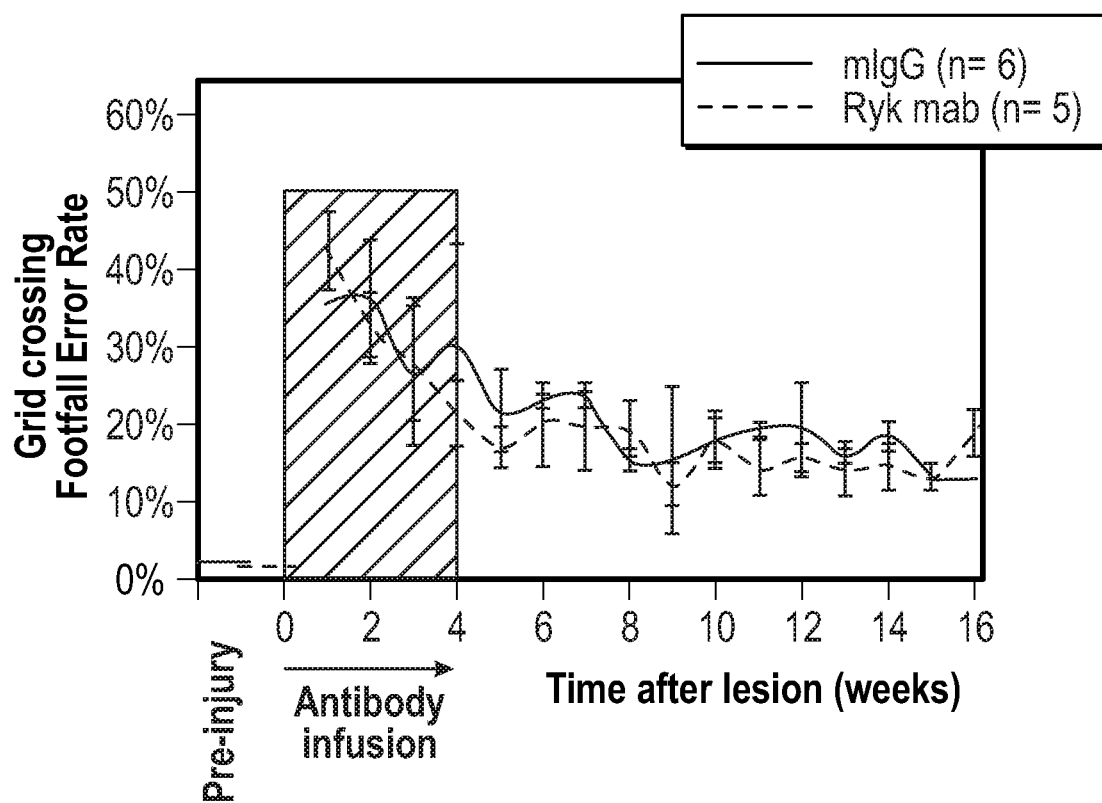
Figure 12D:
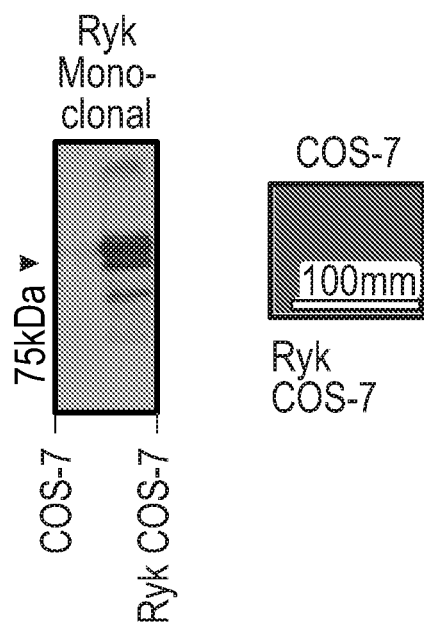
Figure 12E:
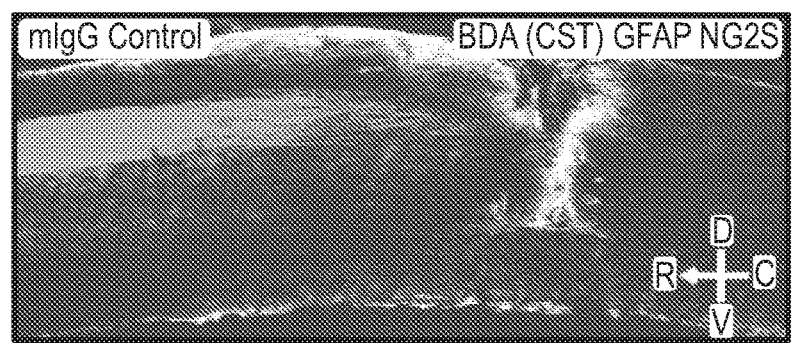
Figure 12F:
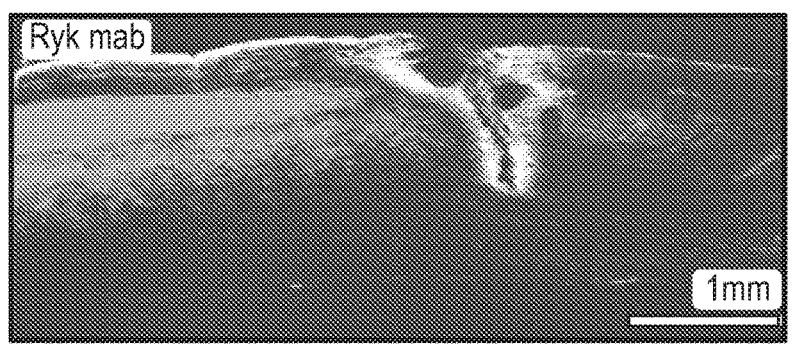
Figure 12G:
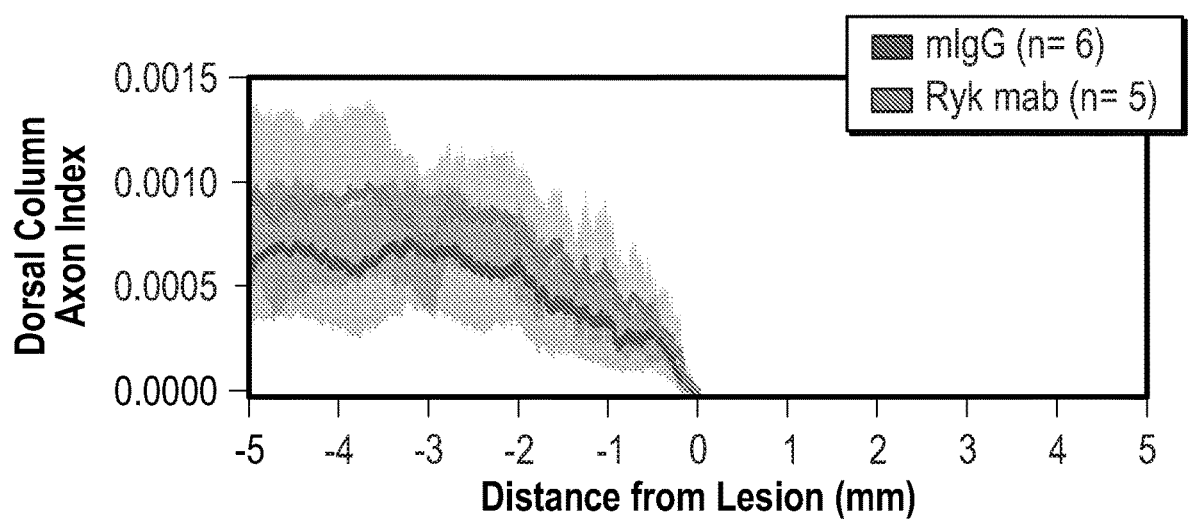
Figure 12H:
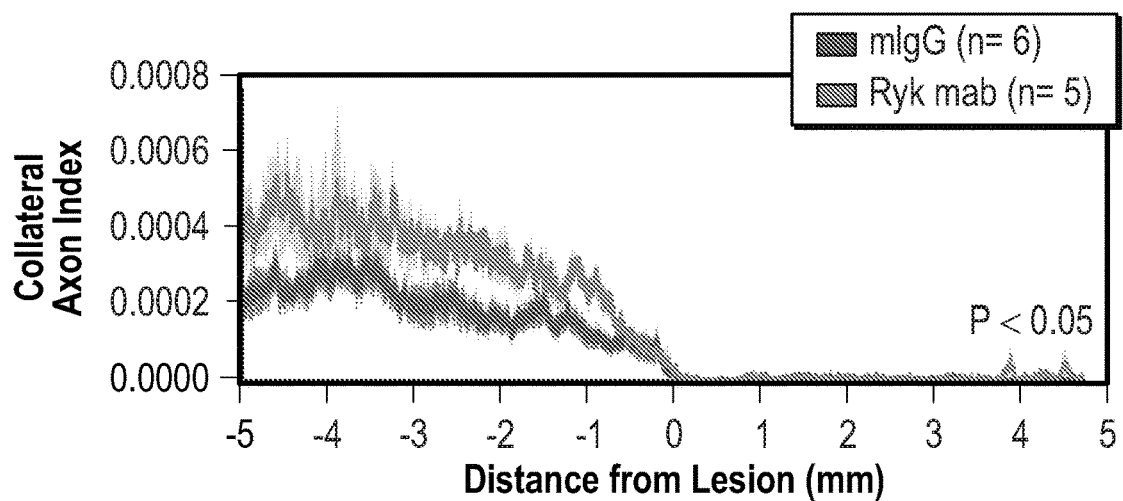
Figure 12I:
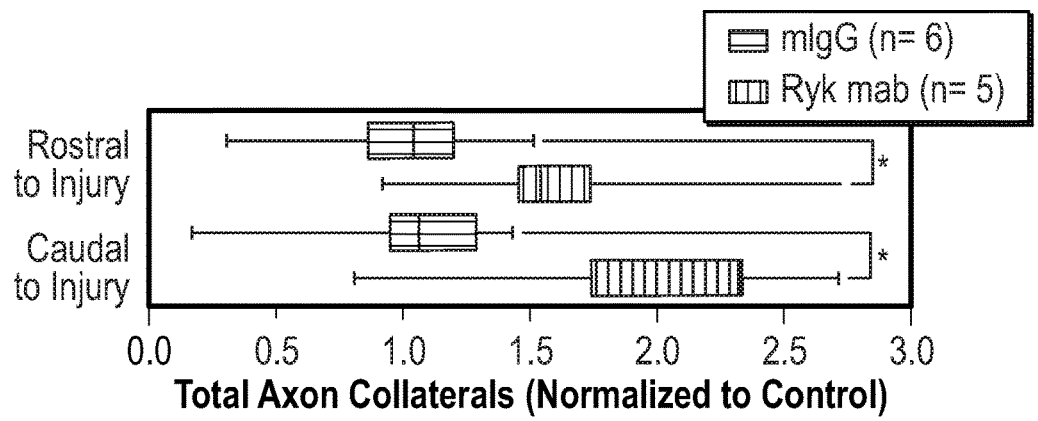
Figure 17A:
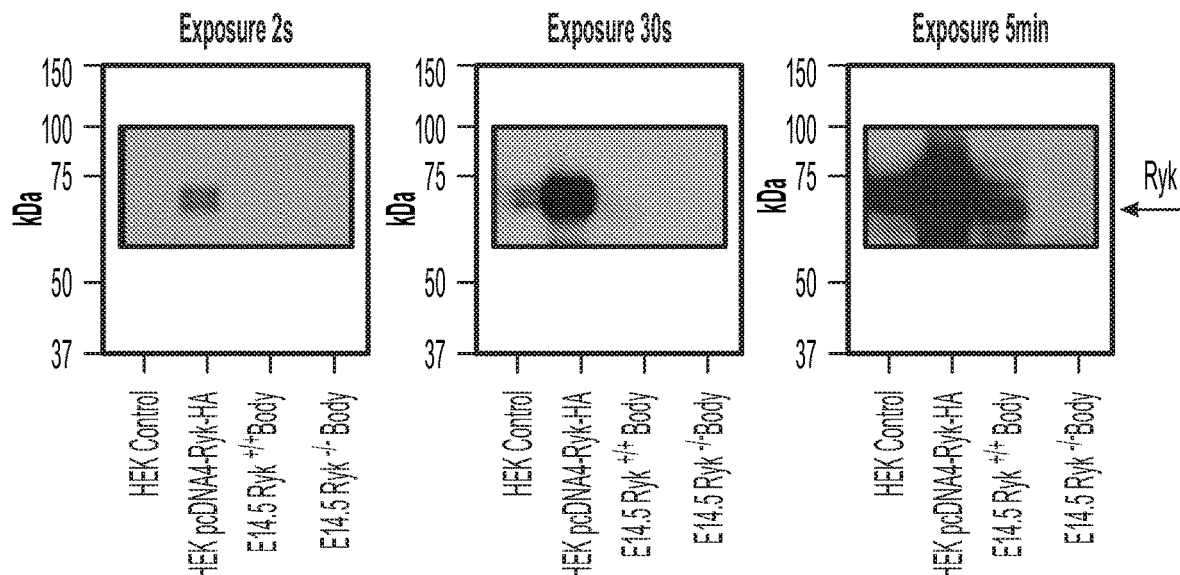
FIGS. 17A and 17B are pictorial diagrams showing Ryk monoclonal antibody infusion in rats.
Figure 17B:
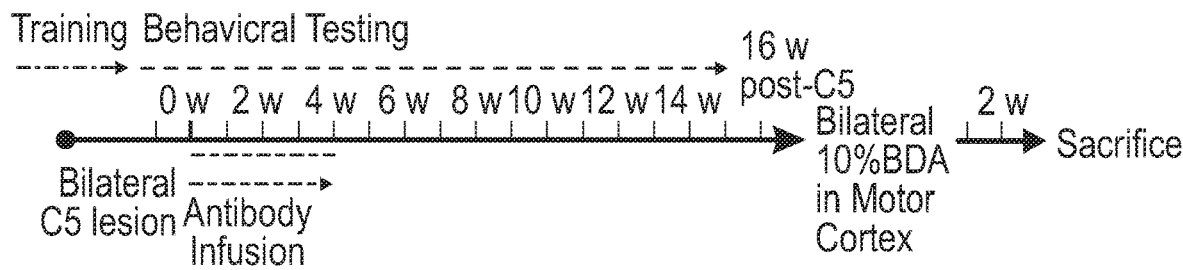
Figure 18:
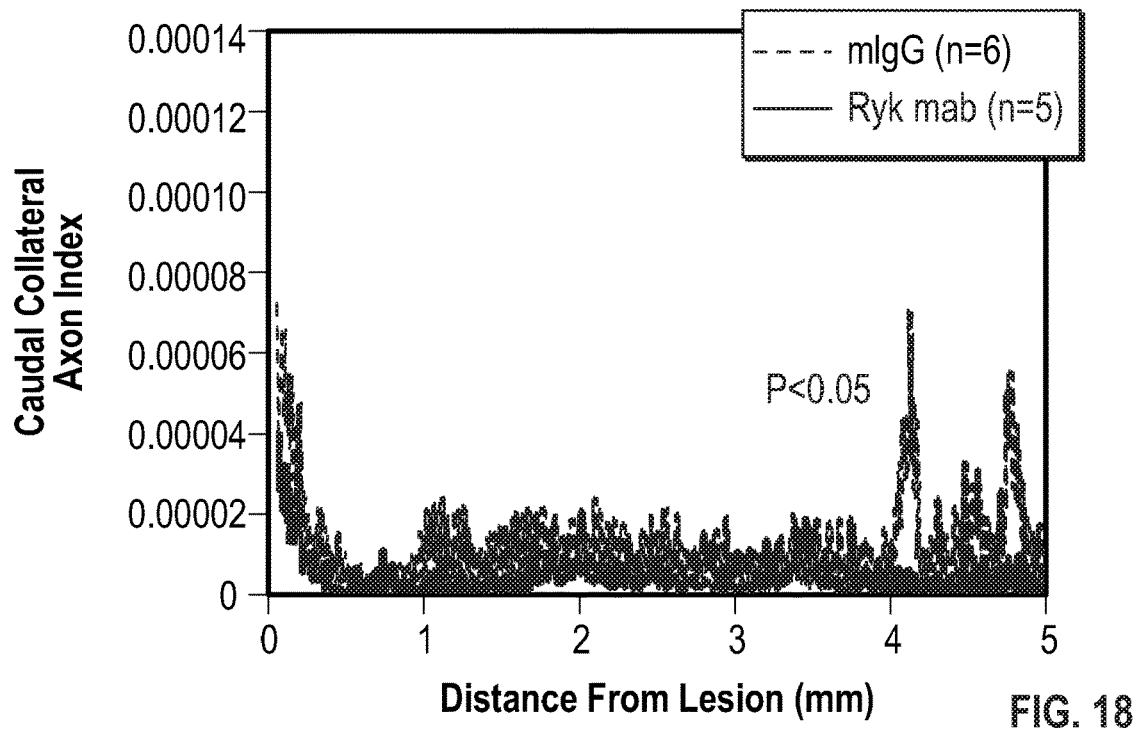
FIG. 18 is a graphical diagram showing that axon collateralization increased after Ryk monoclonal antibody infusion caudal to the injury. Rats infused for 28 days with Ryk monoclonal antibody had greater levels of collateralization caudal to the lesion than control IgG infused rats (n=6 (IgG control) 5 (Ryk monoclonal) rats, one-tailed t-test *P=0.0196 P=0.0196 t(6)=2.594, data presented as mean±s.e.m.). Injury site is at 0 μm, caudal is represented with positive numbers. Axon index is thresholded pixels in sagittal spinal cord divided by thresholded pixels in transverse pyramids.

To test whether inhibition of the Wnt-Ryk signaling axis in the injured spinal cord after spinal cord injury is sufficient to increase CST remodeling and enhance behavioral recovery, a new monoclonal Ryk antibody was generated using half of the Wnt binding domain (amino acid range 90-183) as the antigen and infused into adult rats immediately following spinal cord injury (FIGS. 12A, 17A and 17B). Function-blocking polyclonal antibodies were previously generated using the same region. Following a CS dorsal column wire-knife lesion, Ryk antibody infusion via osmotic minipump for 4 weeks promoted recovery of skilled forelimb function in the forelimb reach task with all rats recovering to peak pre-injury levels, as compared to only half of rats infused with IgG control (FIG. 12B). Ryk antibody did not enhance recovery in the grid crossing locomotor task since rats exhibited similar levels of forelimb stepping impairment irrespective of treatment group (FIG. 12C). Corticospinal axons were labeled with biotinylated dextran amine (BDA) injections into motor cortex. Consistent with the conditional Ryk deletion prior to injury, it was found that the Ryk monoclonal antibody infusion at the time of injury resulted in an increase in corticospinal axon collaterals both rostral and caudal to the level of injury (one-tailed t-test P<0.05, FIGS. 12E-12I and 18). The extent of increase of collateral sprouts after Ryk antibody infusion in rats was similar to that observed in CST axons lacking Ryk expression in mice (FIGS. 9E and 12I). These results also suggest that Ryk signaling is a feasible therapeutic target, since functional recovery can be promoted by blocking its function after spinal cord injury.

EXAMPLE 12

Cortical Map Re-Organization During Recovery

Figure 19:
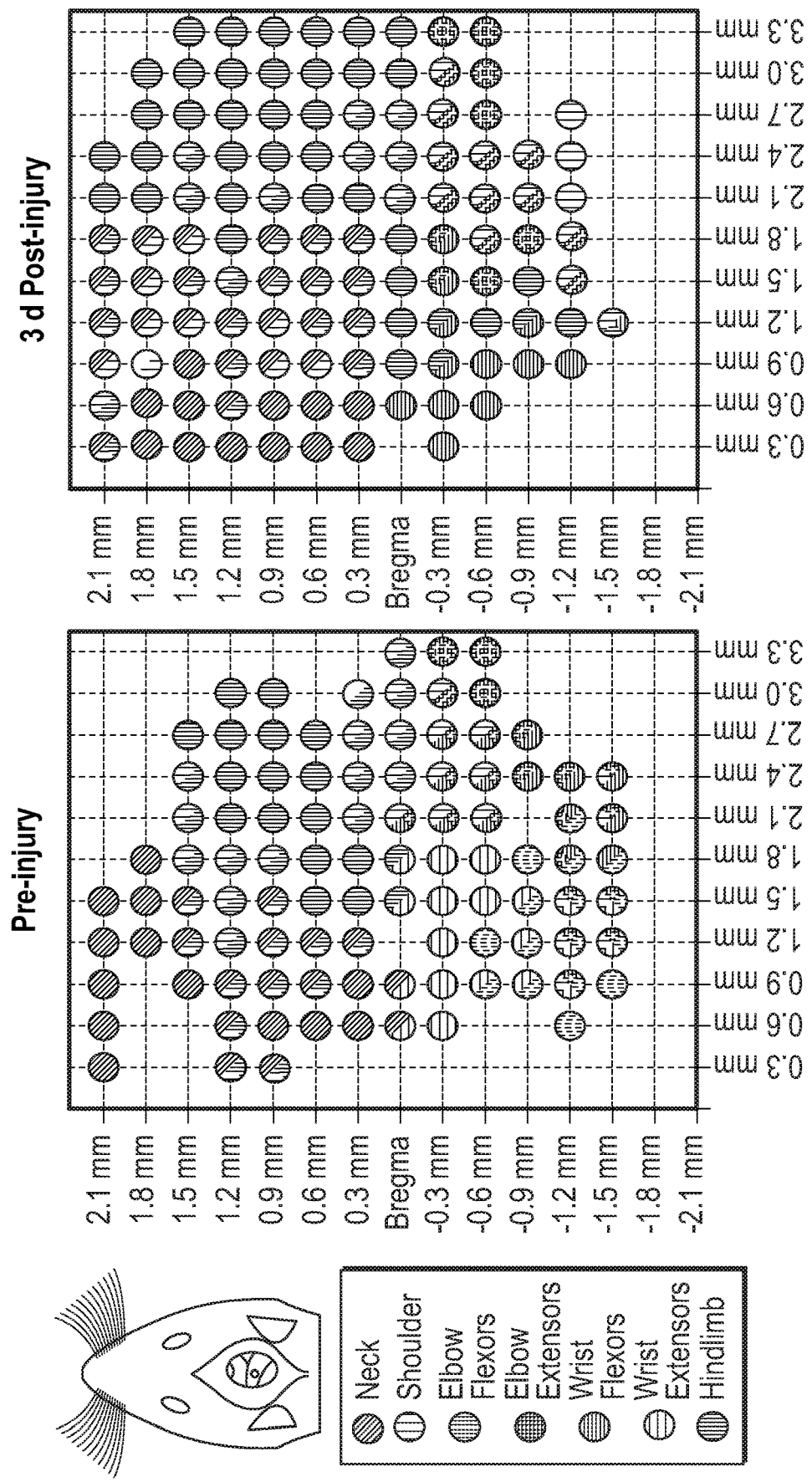
FIG. 19 is a pictorial diagram showing an optogenetic mapping example. Sedated mice with unilateral cranial windows were stimulated with 470 nm LED by fiber optic cable to evoke muscle movements. Two examples of motor maps from one animal, pre- and 3 days post-CS dorsal column lesion are shown.

In order to address the circuit mechanisms with which the primary motor cortex regains control over the remodeled spinal cord, an optogenetics approach was used to monitor cortical output. Cortical motor maps have been studied using intracortical electrical stimulation in rodents and primates, as well as transcranial magnetic stimulation in humans. Recent advances in optogenetic tools allow for the stimulation of specific neural populations in a minimally invasive manner. Specifically, the expression of the light-activated, non-selective, cation channel channelrhodopsin-2 (ChR2) under control of the Thy1 promoter (Thy1-ChR2) allows for selective activation of layer V projection neurons within the motor cortex. Unilateral craniotomies were performed on Thy1-ChR2 mice contralateral to the dominant forelimb in order to investigate motor map changes through repeated optogenetic mapping of evoked motor output after injury (FIG. 19). Following craniotomy, AAV-Cre was injected unilaterally into the motor cortex contralateral to the dominant forelimb as contralateral cortex exhibits motor plasticity in response to forelimb training; and CST collateral plasticity, which supports functional recovery, was specifically induced in CST axons with Ryk deletion. Motor map output was assessed by observing evoked, contralateral motor outputs in sedated mice.

Figure 14A:
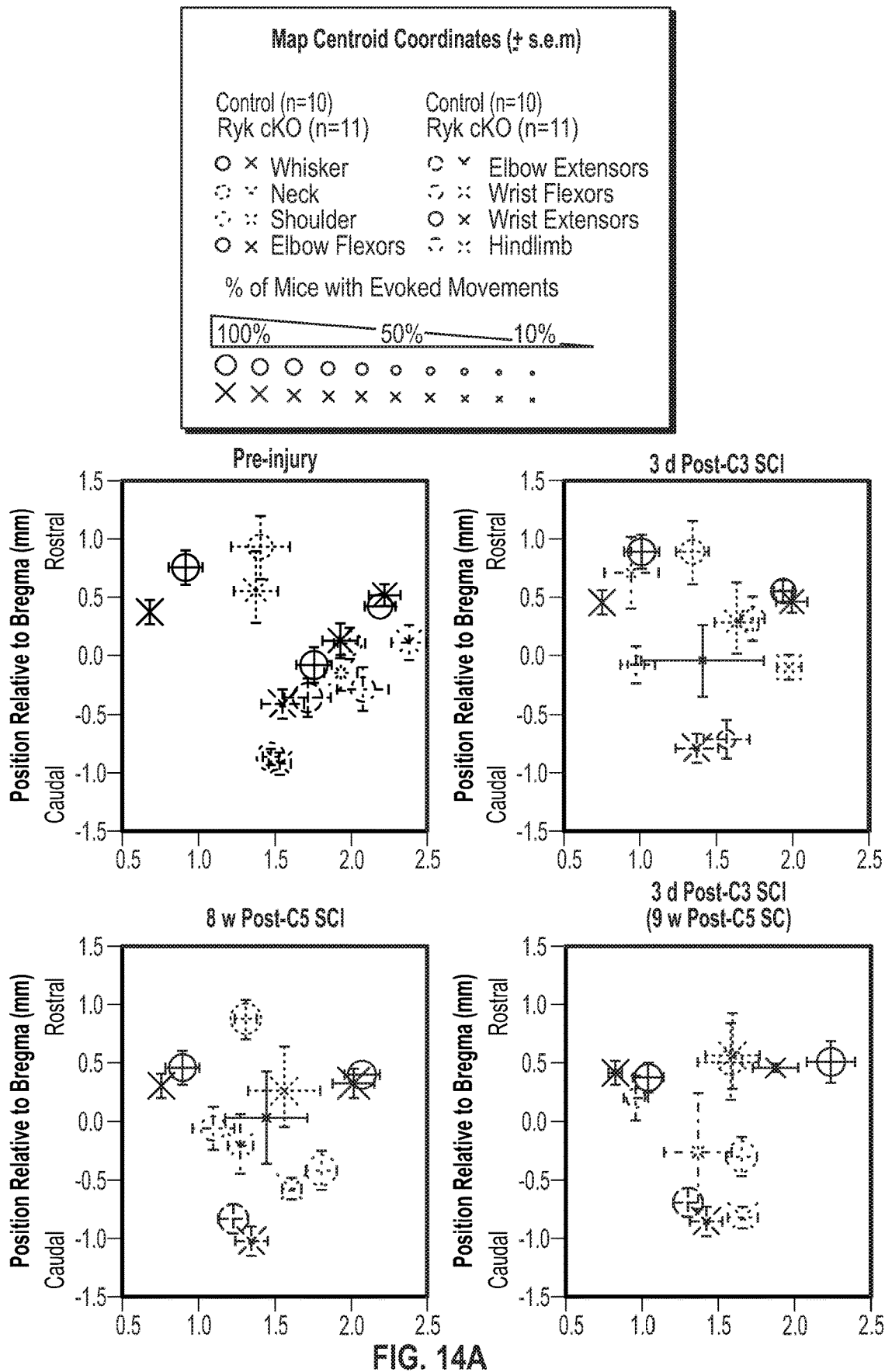
FIGS. 14A-14F are graphical and pictorial diagrams showing forelimb motor map representations infiltrate quiescent former hindlimb cortical areas.
Figure 14B:
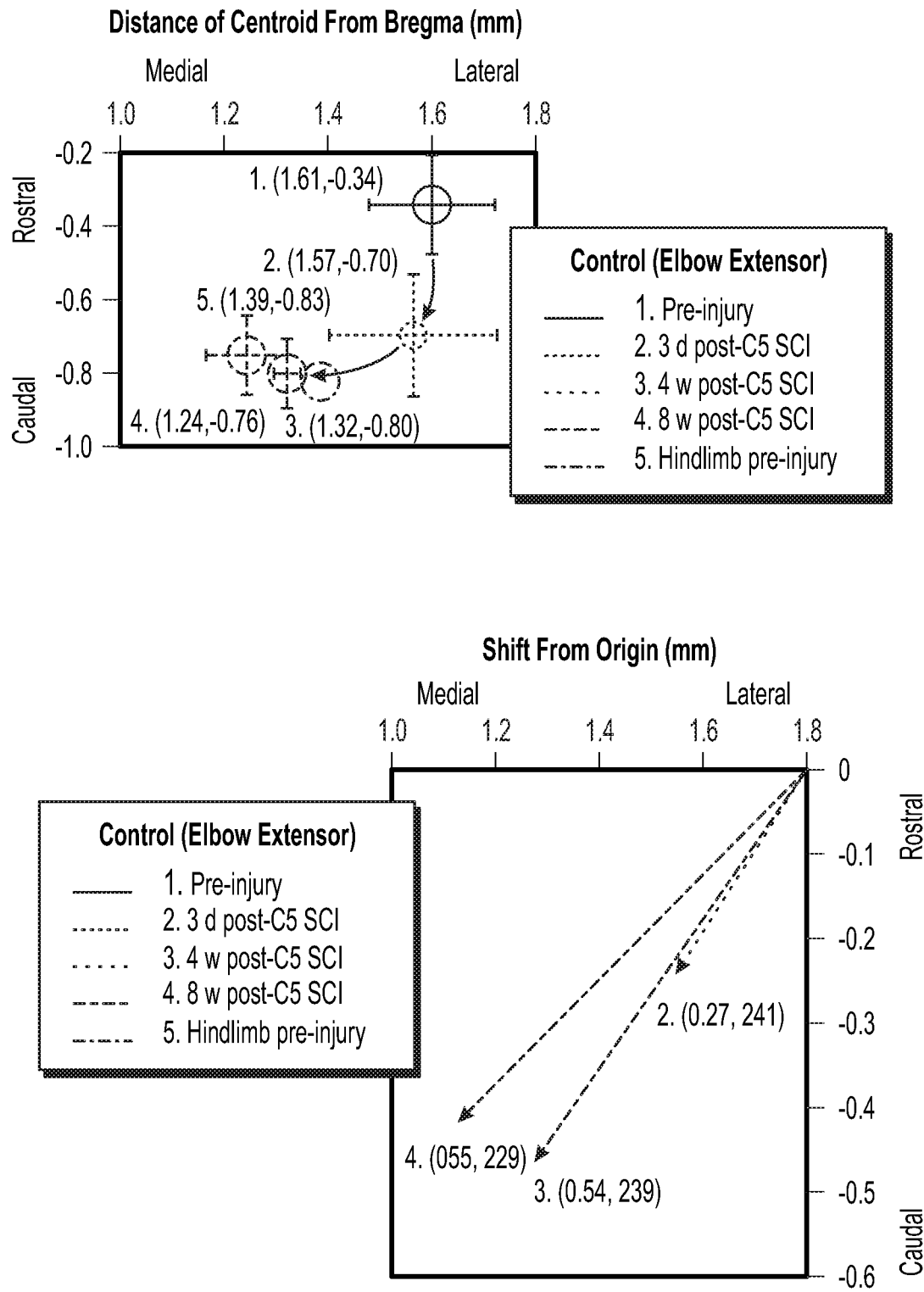
Figure 14C:
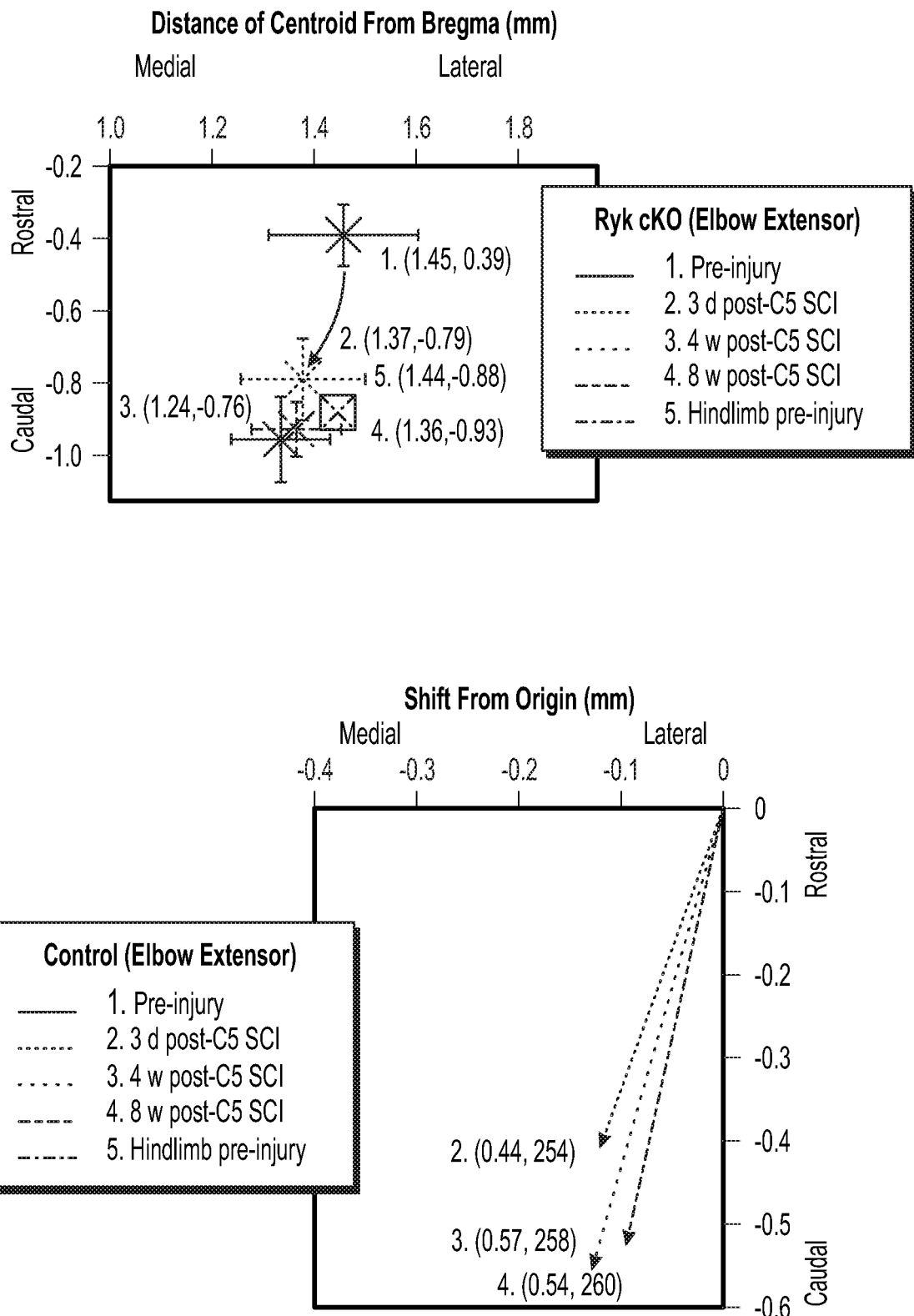
Figure 14D:
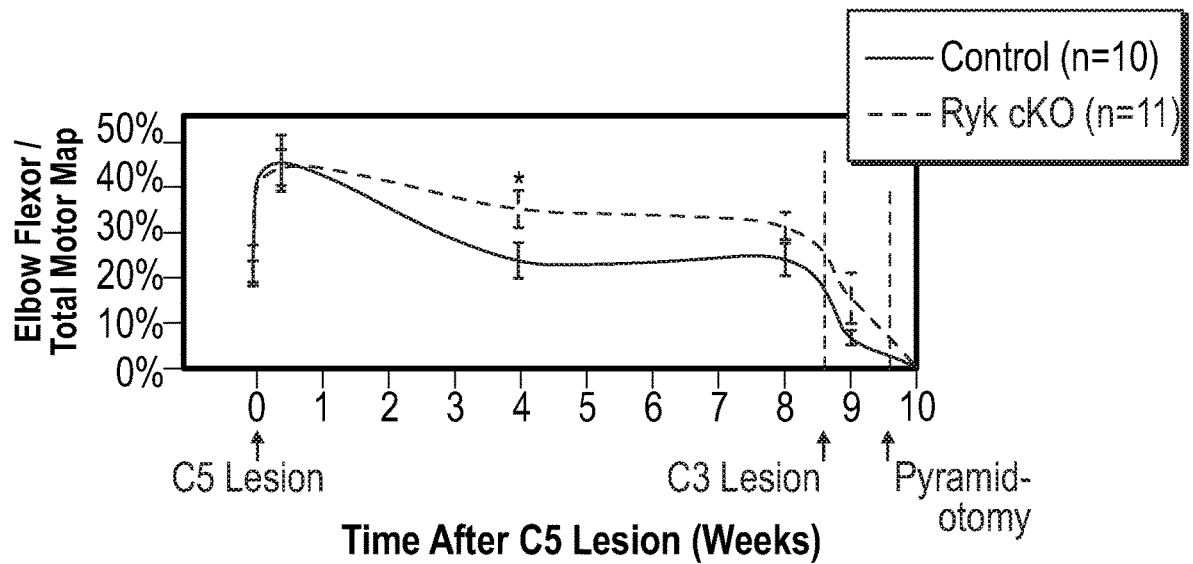
Figure 14E:
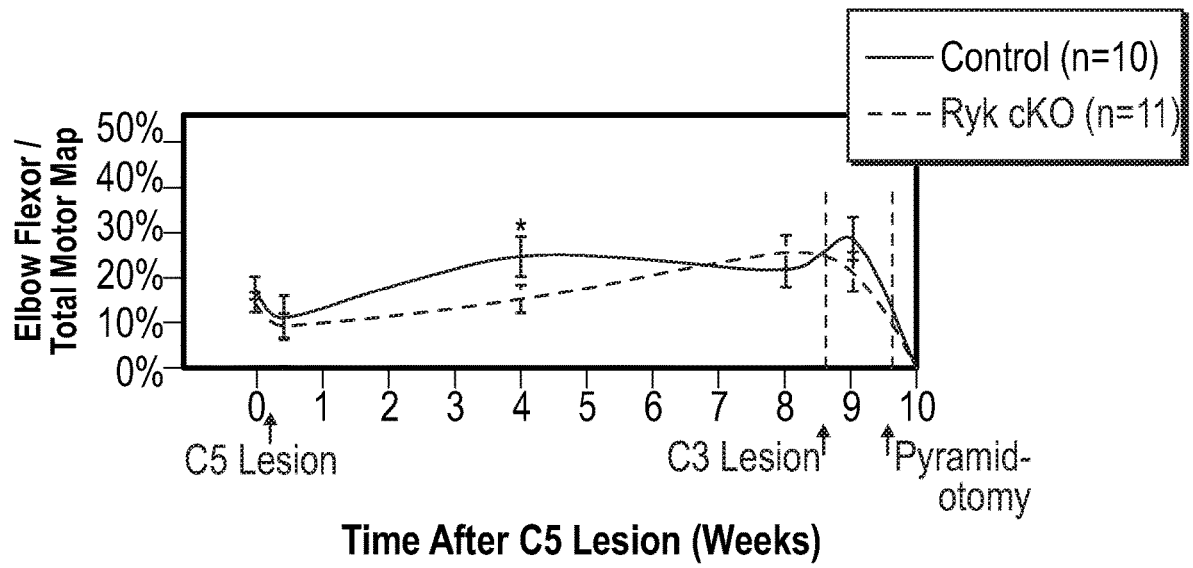
Figure 14F:
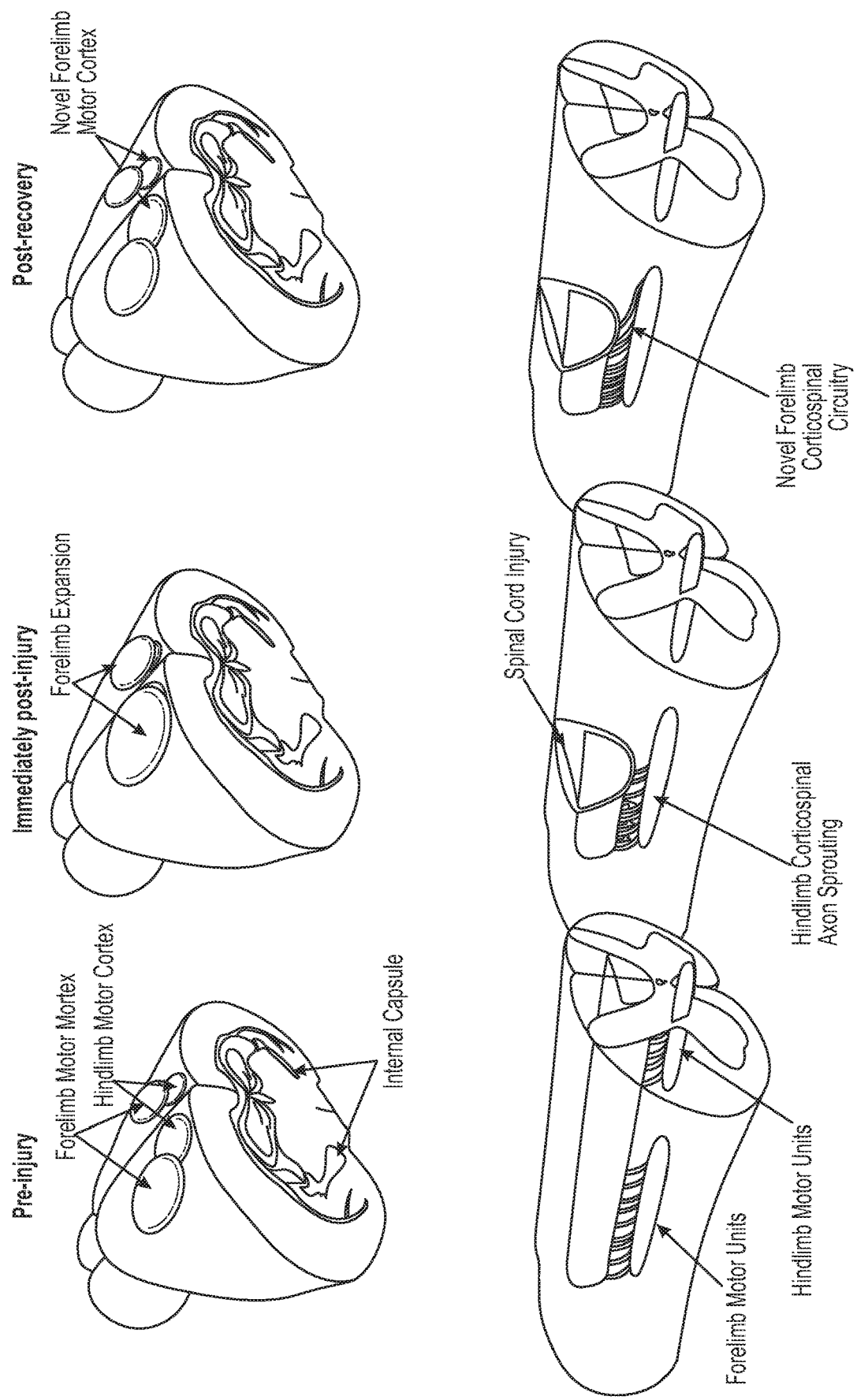
Figure 20:
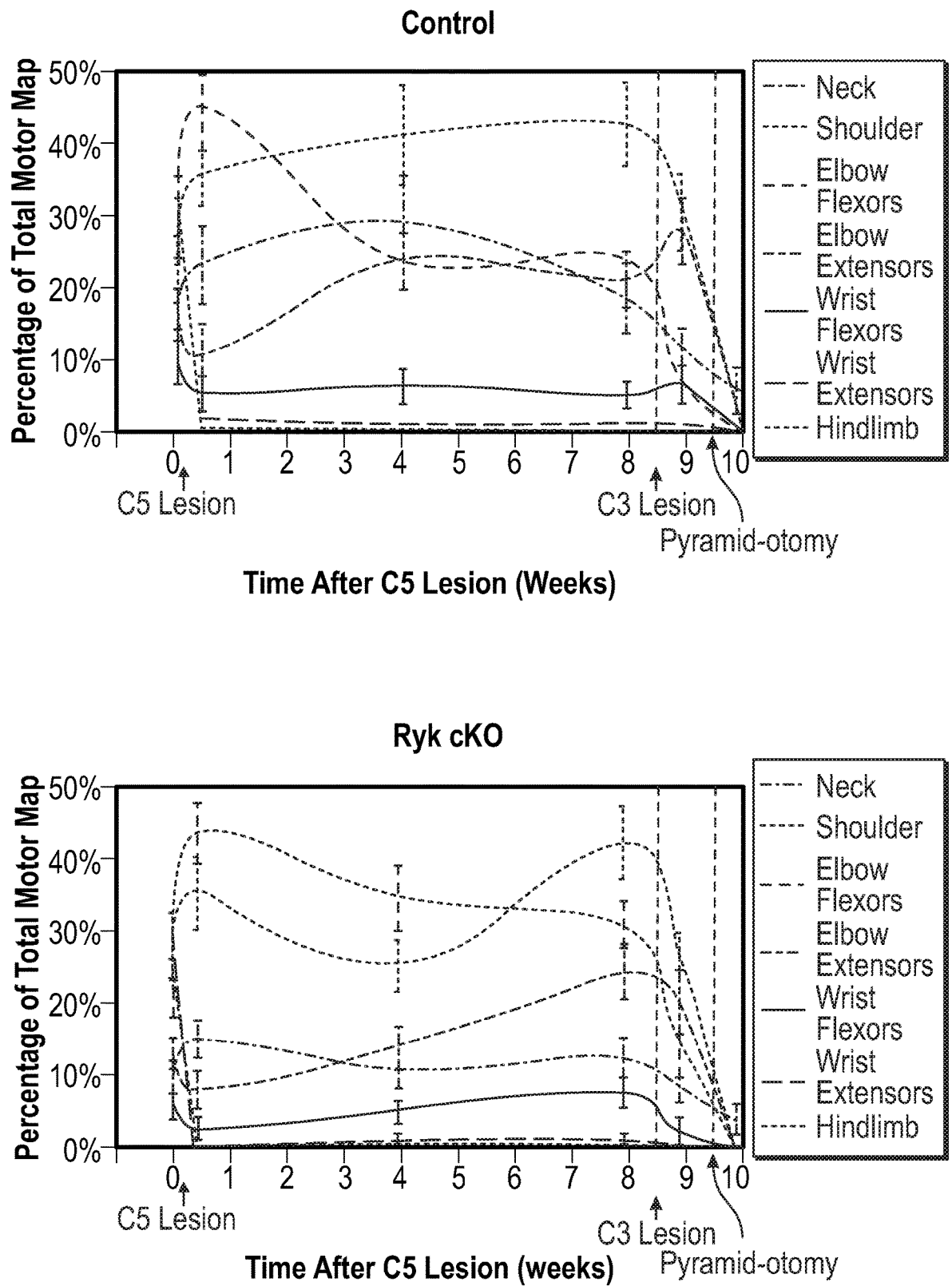
FIG. 20 is a graphical diagram showing the proportion of motor cortex occupied by characterized motor output changes over time in response to weekly training and Ryk conditional deletion

Massive remapping of cortical motor output was observed immediately after spinal cord injury in the mouse. Acutely (3 days) after CS injury, the total area of motor representations for limb muscles at or below the level of lesion was reduced or eliminated (FIG. 12C). Conversely, motor maps expanded for muscle groups with motor neurons above the injury site, most notably elbow flexion mediated by biceps brachii and brachialis (FIGS. 13B, 14E, and 20C). Over the next two months following spinal cord lesion, cortical maps underwent gradual changes with continued forelimb reaching and grasping training (FIG. 20). Behavioral recovery after CS spinal cord injury plateaued between 4 and 8 weeks post-injury (FIGS. 8F and 2I), with a median time to reach 90% of peak, post-injury, performance of either 6 weeks in control mice or 5 weeks in Ryk conditional deletion. Therefore, cortical motor maps were examined before and after peak recovery at 4 weeks and 8 weeks, respectively, post-injury. At 4 weeks post-injury, significant differences were observed in the proportion of motor cortex allocated to forelimb extensor (biceps) or forelimb flexor (triceps) activation, with Ryk deleted mice exhibiting larger flexor motor maps at the expense of reduced extensor maps ($P<0.05$ one-tailed t-test, FIGS. 14E and 14F). Expansion of elbow extensor areas at 4 weeks into regions originally occupied by the flexor was inversely correlated with behavioral recovery (n=21 mice: 10 (control), 11 (Ryk cKO), Spearman's p=−0.5766, P=0.0062). By 8 weeks post-injury, Ryk deleted mice exhibited a similar pattern of extensor and flexor motor maps as controls, however the total area occupied by all elbow movements (flexor and extensor) was significantly larger in Ryk deleted mice (one-tailed t-test, P=0.0480 t(14)=1.79). Additionally, at 8 weeks post-injury, wrist flexor representations returned to (or exceeded) maximal pre-injury size in 64% of Ryk deleted mice compared to 10% of control mice (Wilcoxon rank sum P=0.0136 $\chi^2$=6.086, FIG. 20C). Recovery of wrist flexor control correlated with improvement of forelimb reach performance at 8 weeks post-injury (Spearman's p=0.4555, P=0.0380). Over the course of the experiment, there was a strong correlation of wrist movement and skilled forelimb reach performance, regardless of injury or genotype (Pearson's p=0.665, P<0.0001, FIG. 15D).

In order to further characterize the remapped cortical output, mice were subjected to a second dorsal column lesion at C3, rostral to the level of extensor motor units, at 8 weeks after CS injury (FIG. 11B). It was found that the C3 injury significantly reduced flexor motor maps in all mice but, surprisingly, had little effect on the recovered extensor motor maps, suggesting the flexor control is routed from connections rostral to C3 or from the lateral corticospinal tract (FIG. 13D). Importantly, a subsequent unilateral pyramidotomy abolished unilateral forelimb responses to cortical stimulation and also the ability of mice to perform the forelimb reach task (FIGS. 13D and 21). Although plasticity of other supraspinal pathways, such as the rubrospinal tract or reticulospinal tract may also contribute to functional recovery, the effects of unilateral pyramidotomy suggest that a direct connection between the primary motor cortex with the cervical spinal cord is essential for the recovery of voluntary skilled forelimb movement.

EXAMPLE 13

Cortical Re-organization Requires Rehabilitative Training

Figure 22:
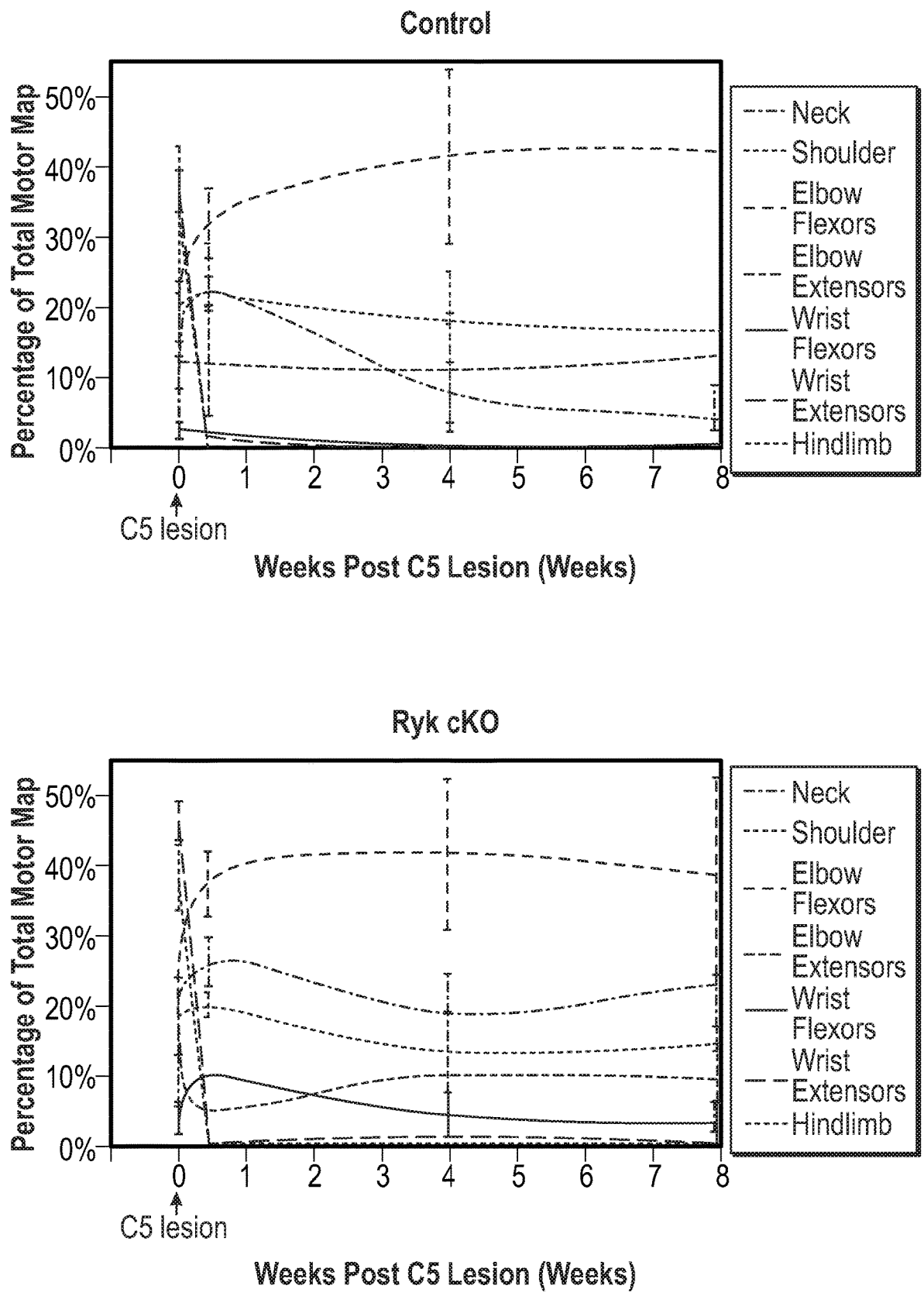
FIG. 22 is a graphical diagram showing that proportions of motor cortex occupied by characterized motor output are relatively stable in the absence of training after injury.
Figure 23A:
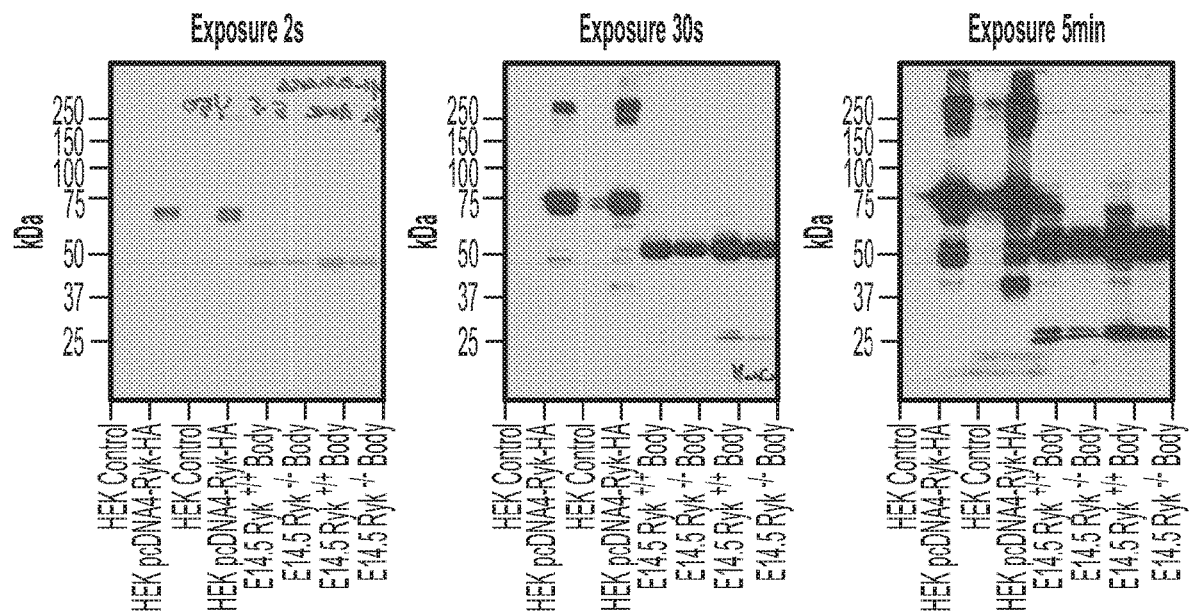
FIGS. 23A and 23B are pictorial diagrams showing the results of full Western blots from FIG. 8C and FIG. 17A.
Figure 23B:
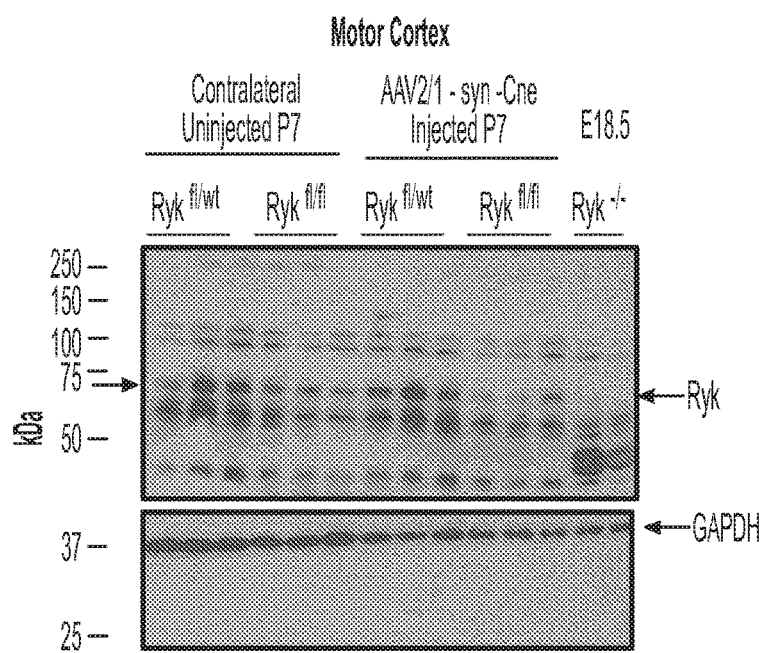

The repeated testing of skilled forelimb reach over the course of the experiment essentially constitutes a rehabilitative training paradigm that can promote motor recovery from spinal cord injury and cortical reorganization. In order to determine if the induced axonal plasticity mediated by Ryk deletion alone was required to promote functional recovery, the recovery of skilled forelimb reach was tested at 8 weeks after CS injury in another cohort of mice that did not undergo weekly behavioral testing after injury (FIG. 15A). Mice that did not undergo weekly behavioral testing displayed only limited skilled forelimb recovery with performance similar to that of mice tested at one week after injury (FIGS. 15C and 8F). In the absence of weekly testing, refinement of cortical motor maps was also impaired, irrespective of Ryk conditional deletion (FIGS. 15B and 22).

REFERENCES

1. Saxena, et al. (2007) Mechanisms of axon degeneration: from development to disease. (Translated from eng) Progress in neurobiology 83(3):174-191 (in eng).
2. Wang, et al. (2012) Axon degeneration: molecular mechanisms of a self-destruction pathway. (Translated from eng) The Journal of cell biology 196(1):7-18 (in eng).
3. Yan, et al. (2010) Axon degeneration: Mechanisms and implications of a distinct program from cell death. (Translated from eng) Neurochemistry international 56(4):529-534 (in eng).
4. Schmidt, et al. (2009) Axon guidance proteins: novel therapeutic targets for ALS? (Translated from eng) Prog Neurobiol 88(4):286-301 (in eng).
5. Van Hoecke, et al. (EPHA4 is a disease modifier of amyotrophic lateral sclerosis in animal models and in humans. (Translated from eng) Nat Med 18(9):1418-1422 (in eng).
6. Tury, et al. (Altered expression of atypical PKC and Ryk in the spinal cord of a mouse model of amyotrophic lateral sclerosis. (Translated from Eng) Dev Neurobiol (in Eng).
7. Shi, et al. (2003) Hippocampal neuronal polarity specified by spatially localized mPar3/mPar6 and PI 3-kinase activity. (Translated from eng) Cell 112(1):63-75 (in eng).
8. Nishimura, et al. (2004) Role of the PAR-3-KIF3 complex in the establishment of neuronal polarity. (Translated from eng) Nature cell biology 6(4):328-334 (in eng).
9. Chen, et al. (2006) Microtubule affinity-regulating kinase 2 functions downstream of the PAR-3/PAR-6/atypical PKC complex in regulating hippocampal neuronal polarity. (Translated from eng) Proceedings of the National Academy of Sciences of the United States of America 103(22):8534-8539 (in eng).
10. Parker, et al. (2013) Competing molecular interactions of aPKC isoforms regulate neuronal polarity. (Translated from eng) Proceedings of the National Academy of Sciences of the United States of America 110(35):14450-14455 (in eng).
11. Zhang, et al. (2007) Dishevelled promotes axon differentiation by regulating atypical protein kinase C. (Translated from eng) Nature cell biology 9(7):743-754 (in eng).
12. Mori, et al. (2009) An essential role of the aPKC-Aurora A-NDEL1 pathway in neurite elongation by modulation of microtubule dynamics. (Translated from eng) Nature cell biology 11(9):1057-1068 (in eng).

13. Parker, et al. (Competing molecular interactions of aPKC isoforms regulate neuronal polarity. (Translated from eng) Proc Natl Acad Sci USA 110(35):14450-14455 (in eng).
14. Wolf, et al. (2008) Phosphatidylinositol-3-kinase-atypical protein kinase C signaling is required for Wnt attraction and anterior-posterior axon guidance. (Translated from eng) The Journal of neuroscience: the official journal of the Society for Neuroscience 28(13):3456-3467 (in eng).
15. Onishi, et al. (Antagonistic Functions of Dishevelleds Regulate Frizzled3 Endocytosis via Filopodia Tips in Wnt-Mediated Growth Cone Guidance. (Translated from eng) J Neurosci 33(49):19071-19085 (in eng).
16. Wang, et al. (1999) Atypical PKC zeta is activated by ceramide, resulting in coactivation of NF-kappaB/JNK kinase and cell survival. (Translated from eng) Journal of neuroscience research 55(3):293-302 (in eng).
17. Wooten, et al. (1999) Overexpression of atypical PKC in PC12 cells enhances NGF-responsiveness and survival through an NFkappaB dependent pathway. (Translated from eng) Cell death and differentiation 6(8):753-764 (in eng).
18. Xie, et al. (2000) Protein kinase C iota protects neural cells against apoptosis induced by amyloid beta-peptide. (Translated from eng) Brain research. Molecular brain research 82(1-2):107-113 (in eng).
19. Huang, et al. (2001) Activation of protein kinase A and atypical protein kinase C by A(2A) adenosine receptors antagonizes apoptosis due to serum deprivation in PC12 cells. (Translated from eng) The Journal of biological chemistry 276(17):13838-13846 (in eng).
20. Kim, et al. (2007) Polarity proteins PAR6 and aPKC regulate cell death through GSK-3beta in 3D epithelial morphogenesis. (Translated from eng) Journal of cell science 120(Pt 14):2309-2317 (in eng).
21. Joung, et al. (2005) p62 modulates Akt activity via association with PKCzeta in neuronal survival and differentiation. (Translated from eng) Biochemical and biophysical research communications 334(2):654-660 (in eng).
22. Xin, et al. (2007) Protein kinase Czeta abrogates the proapoptotic function of Bax through phosphorylation. (Translated from eng) The Journal of biological chemistry 282(29):21268-21277 (in eng).
23. Reyland M E (2009) Protein kinase C isoforms: Multifunctional regulators of cell life and death. (Translated from eng) Front Biosci (Landmark Ed) 14:2386-2399 (in eng).
24. Liu, et al. (2005) Ryk-mediated Wnt repulsion regulates posterior-directed growth of corticospinal tract. (Translated from eng) Nature neuroscience 8(9):1151-1159 (in eng).
25. Schmitt, et al. (2006) Wnt-Ryk signalling mediates medial-lateral retinotectal topographic mapping. (Translated from eng) Nature 439(7072):31-37 (in eng).
26. Keeble, et al. (2006) Ryk: a novel Wnt receptor regulating axon pathfinding. (Translated from eng) The international journal of biochemistry & cell biology 38(12): 2011-2017 (in eng).
27. Keeble, et al. (2006) The Wnt receptor Ryk is required for Wnt5a-mediated axon guidance on the contralateral side of the corpus callosum. (Translated from eng) The Journal of neuroscience: the official journal of the Society for Neuroscience 26(21):5840-5848 (in eng).
28. Gonzalez, et al. (2013) The ryk receptor is expressed in glial and fibronectin-expressing cells after spinal cord injury. (Translated from eng) Journal of neurotrauma 30(10):806-817 (in eng).
29. Hollis E R, 2nd & Zou Y (2012) Reinduced Wnt signaling limits regenerative potential of sensory axons in the spinal cord following conditioning lesion. (Translated from eng) Proceedings of the National Academy of Sciences of the United States of America 109(36):14663-14668 (in eng).
30. Hollis E R, 2nd & Zou Y (2012) Expression of the Wnt signaling system in central nervous system axon guidance and regeneration. (Translated from eng) Frontiers in molecular neuroscience 5:5 (in eng).
31. Fradkin, et al. (2010) Ryks: new partners for Wnts in the developing and regenerating nervous system. (Translated from eng) Trends in neurosciences 33(2):84-92 (in eng).
32. Liu, et al. (2008) Repulsive Wnt signaling inhibits axon regeneration after CNS injury. (Translated from eng) The Journal of neuroscience: the official journal of the Society for Neuroscience 28(33):8376-8382 (in eng).
33. Miyashita, et al. (2009) Wnt-Ryk signaling mediates axon growth inhibition and limits functional recovery after spinal cord injury. (Translated from eng) Journal of neurotrauma 26(7):955-964 (in eng).
34. Guenther, et al. (2012) Increased atypical PKC expression and activity in the phrenic motor nucleus following cervical spinal injury. (Translated from eng) Experimental neurology 234(2):513-520 (in eng).
35. Luo L & O'Leary D D (2005) Axon retraction and degeneration in development and disease. (Translated from eng) Annual review of neuroscience 28:127-156 (in eng).
36. Watts, et al. (2003) Axon pruning during *Drosophila* metamorphosis: evidence for local degeneration and requirement of the ubiquitin-proteasome system. (Translated from eng) Neuron 38(6):871-885 (in eng).
37. Zhai, et al. (2003) Involvement of the ubiquitin-proteasome system in the early stages of wallerian degeneration. (Translated from eng) Neuron 39(2):217-225 (in eng).
38. Xiao, et al. (2006) Insights into the mechanism of microtubule stabilization by Taxol. (Translated from eng) Proceedings of the National Academy of Sciences of the United States of America 103(27):10166-10173 (in eng).
39. Drewes, et al. (1997) MARK, a novel family of protein kinases that phosphorylate microtubule-associated proteins and trigger microtubule disruption. (Translated from eng) Cell 89(2):297-308 (in eng).
40. Hurov, et al. (2004) Atypical PKC phosphorylates PAR-1 kinases to regulate localization and activity. (Translated from eng) Current biology: CB 14(8):736-741 (in eng).
41. Matenia D & Mandelkow E M (2009) The tau of MARK: a polarized view of the cytoskeleton. (Translated from eng) Trends in biochemical sciences 34(7):332-342 (in eng).
42. Shen H M & Liu Z G (2006) JNK signaling pathway is a key modulator in cell death mediated by reactive oxygen and nitrogen species. (Translated from eng) Free radical biology & medicine 40(6):928-939 (in eng).
43. Manning A M & Davis R J (2003) Targeting JNK for therapeutic benefit: from junk to gold? (Translated from eng) Nature reviews. Drug discovery 2(7):554-565 (in eng).
44. Yoshimura K, et al. (2011) c-Jun N-terminal kinase induces axonal degeneration and limits motor recovery 45. Li, et al. (2004) JNK-dependent phosphorylation of c-Jun on serine 63 mediates nitric oxide-induced apoptosis of neuroblastoma cells. (Translated from eng) The Journal of biological chemistry 279(6):4058-4065 (in eng).
46. Onishi K, et al. (2013) Antagonistic Functions of Dishevelleds Regulate Frizzled3 Endocytosis via Filopodia Tips in Wnt-Mediated Growth Cone Guidance. (Translated from eng) The Journal of neuroscience: the official journal of the Society for Neuroscience 33(49): 19071-19085 (in eng).
47. Tury, et al. (2013) Altered expression of atypical PKC and Ryk in the spinal cord of a mouse model of amyotrophic lateral sclerosis. (Translated from Eng) Developmental neurobiology (in Eng).
48. Kamitori. Et al. (1999) Expression of receptor tyrosine kinase RYK in developing rat central nervous system. (Translated from eng) Brain research. Developmental brain research 114(1):149-160 (in eng).
49. Lyu, et al. (2008) Cleavage of the Wnt receptor Ryk regulates neuronal differentiation during cortical neurogenesis. (Translated from eng) Developmental cell 15(5): 773-780 (in eng).
50. Halford M M, et al. (2000) Ryk-deficient mice exhibit craniofacial defects associated with perturbed Eph receptor crosstalk. (Translated from eng) Nature genetics 25(4): 414-418 (in eng).
51. Wang, et al. (2002) Frizzled-3 is required for the development of major fiber tracts in the rostral CNS. (Translated from eng) The Journal of neuroscience: the official journal of the Society for Neuroscience 22(19): 8563-8573 (in eng).
52. Hua, et al. (Frizzled3 controls axonal development in distinct populations of cranial and spinal motor neurons. (Translated from eng) Elife 2(0):e01482 (in eng).
53. Shafer, et al. (Vangl2 promotes Wnt/planar cell polarity-like signaling by antagonizing Dvl1-mediated feedback inhibition in growth cone guidance. (Translated from eng) Dev Cell 20(2):177-191 (in eng).
54. Macheda M L, et al. (The Wnt Receptor Ryk Plays a Role in Mammalian Planar Cell Polarity Signaling. (Translated from Eng) J Biol Chem (in Eng).
55. Andre P, et al. (The Wnt coreceptor Ryk regulates Wnt/planar cell polarity by modulating the degradation of the core planar cell polarity component Vangl2. (Translated from Eng) J Biol Chem (in Eng).
56. Romanelli, et al. (1999) p70 S6 kinase is regulated by protein kinase Czeta and participates in a phosphoinositide 3-kinase-regulated signalling complex. (Translated from eng) Molecular and cellular biology 19(4):2921-2928 (in eng).
57. Mairet-Coello G, et al. (2013) The CAMKK2-AMPK kinase pathway mediates the synaptotoxic effects of Abeta oligomers through Tau phosphorylation. (Translated from eng) Neuron 78(1):94-108 (in eng).

Although the invention has been described with reference to the above examples, it will be understood that modifications and variations are encompassed within the spirit and scope of the invention. Accordingly, the invention is limited only by the following claims.

What is claimed is:

1. A method of treating a neurological injury in a subject having the neurological injury comprising administering to the subject an effective amount of an isolated anti-Ryk antibody or antibody fragment that specifically binds to a binding domain of Wnt on Ryk or specifically binds to an epitope within a region of the ectodomain of Ryk, amino-acids 90-183 of Ryk, and inhibits Wnt-Ryk interaction, wherein the isolated anti-Ryk antibody or antibody fragment comprises a heavy chain variable region comprising the amino acid sequence set forth in SEQ ID NO: 8 and a light chain variable region comprising the amino acid sequence set forth in SEQ ID NO: 4, thereby treating the neurological injury in the subject.

2. The method of claim 1, wherein the isolated anti-Ryk antibody or antibody fragment specifically binds to an epitope within amino acid residues 90-183 of Ryk.

3. The method of claim 1, wherein the isolated anti-Ryk antibody or antibody fragment specifically binds to a binding domain of Wnt on Ryk.

4. The method of claim 1, wherein the subject is a mammal.

5. The method of claim 4, wherein the mammal is a human.

6. The method of claim 1, wherein the neurological injury is spinal cord injury (SCI).

7. A method of treating a neurological injury in a subject having the neurological injury comprising administering to the subject an effective amount of an isolated anti-Ryk antibody or antibody fragment, wherein the isolated anti-Ryk antibody or antibody fragment comprises a heavy chain variable region comprising the CDR sequences set forth in SEQ ID NOs: 5-7; and a light chain variable region comprising the CDR sequences set forth in SEQ ID NOs: 1-3, thereby treating the neurological injury in the subject.

8. The method of claim 7, wherein the isolated anti-Ryk antibody or antibody fragment comprises a heavy chain variable region comprising the amino acid sequence set forth in SEQ ID NO: 8 and a light chain variable region comprising the amino acid sequence set forth in SEQ ID NO: 4.

9. The method of claim 7, wherein the isolated anti-Ryk antibody or antibody fragment:
   (a) specifically binds to a binding domain of Wnt on Ryk; or p1 (b) specifically binds to an epitope within a region of the ectodomain of Ryk; or
   (c) specifically binds to an epitope within amino-acids 90-183 of Ryk; and/or
   (d) inhibits Wnt-Ryk interaction.

* * * * *